US012070495B2

(12) United States Patent
Lusso et al.

(10) Patent No.: US 12,070,495 B2
(45) Date of Patent: Aug. 27, 2024

(54) HIV RNA VACCINES

(71) Applicants: ModernaTX, Inc., Cambridge, MA (US); The United States of America, as represented by the Department of Health and Human Services, Rockville, MD (US)

(72) Inventors: Paolo Lusso, Rockville, MD (US); Peng Zhang, Rockville, MD (US); Elisabeth Narayanan, Cambridge, MA (US); Sayda Mahgoub Elbashir, Cambridge, MA (US)

(73) Assignees: ModernaTX, Inc., Cambridge, MA (US); The United States of America, as represented by the Department of Health and Human Services, Rockville, MD (US)

(*) Notice: Subject to any disclaimer, the term of this patent is extended or adjusted under 35 U.S.C. 154(b) by 104 days.

(21) Appl. No.: 17/439,198

(22) PCT Filed: Mar. 13, 2020

(86) PCT No.: PCT/US2020/022710
§ 371 (c)(1),
(2) Date: Sep. 14, 2021

(87) PCT Pub. No.: WO2020/190750
PCT Pub. Date: Sep. 24, 2020

(65) Prior Publication Data
US 2022/0241399 A1 Aug. 4, 2022

Related U.S. Application Data

(60) Provisional application No. 62/819,394, filed on Mar. 15, 2019.

(51) Int. Cl.
*A61K 39/21* (2006.01)
*A61K 39/39* (2006.01)
*A61K 39/00* (2006.01)

(52) U.S. Cl.
CPC .............. *A61K 39/21* (2013.01); *A61K 39/39* (2013.01); *A61K 2039/53* (2013.01); *A61K 2039/55516* (2013.01); *A61K 2039/6018* (2013.01)

(58) Field of Classification Search
CPC .. A61K 2039/55555; A61K 2039/6018; A61K 39/21; A61K 2039/53; A61K 2039/70; A61K 9/1271; A61P 31/14; A61P 31/18; C12N 2740/15034; C12N 2740/16022; C12N 2740/16023; C12N 2740/16034
See application file for complete search history.

(56) References Cited

U.S. PATENT DOCUMENTS

| | | | |
|---|---|---|---|
| 3,906,092 | A | 9/1975 | Hilleman et al. |
| 5,589,466 | A | 12/1996 | Felgner et al. |
| 5,686,601 | A | 11/1997 | Weber |
| 5,750,114 | A | 5/1998 | Burke et al. |
| 5,955,088 | A | 9/1999 | Ghiasi et al. |
| 5,965,726 | A | 10/1999 | Pavlakis et al. |
| 6,214,804 | B1 | 4/2001 | Feigner et al. |
| 6,413,518 | B1 | 7/2002 | Koelle et al. |
| 6,500,419 | B1 | 12/2002 | Hone et al. |
| 6,514,948 | B1 | 2/2003 | Raz et al. |
| 6,534,312 | B1 | 3/2003 | Shiver et al. |
| 6,610,044 | B2 | 8/2003 | Mathiesen |
| 7,001,890 | B1 | 2/2006 | Wagner et al. |
| 8,158,601 | B2 | 4/2012 | Chen et al. |
| 8,183,352 | B2 | 5/2012 | Ayyavoo et al. |
| 8,217,016 | B2 | 7/2012 | Hoerr et al. |
| 8,242,087 | B2 | 8/2012 | Adelfinskaya et al. |
| 8,569,256 | B2 | 10/2013 | Heyes et al. |
| 8,609,142 | B2 | 12/2013 | Troiano et al. |
| 8,613,954 | B2 | 12/2013 | Zale et al. |
| 8,617,608 | B2 | 12/2013 | Zale et al. |
| 8,673,316 | B2 | 3/2014 | Kinney et al. |
| 8,691,961 | B1 | 4/2014 | Puffer et al. |
| 8,710,200 | B2 | 4/2014 | Schrum et al. |
| 8,734,832 | B2 | 5/2014 | O'Hagan et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,877,206 | B2 | 11/2014 | Chen et al. |
| 8,980,864 | B2 | 3/2015 | Hoge et al. |
| 8,999,380 | B2 | 4/2015 | Bancel et al. |
| 9,000,141 | B2 | 4/2015 | Chang et al. |
| 9,149,543 | B2 | 10/2015 | Hecker et al. |
| 9,221,891 | B2 | 12/2015 | Bancel et al. |
| 9,243,041 | B2 | 1/2016 | Weiner et al. |

(Continued)

FOREIGN PATENT DOCUMENTS

| | | | |
|---|---|---|---|
| AU | 652831 | B2 | 9/1994 |
| AU | 2015210364 | A1 | 3/2017 |

(Continued)

OTHER PUBLICATIONS

International Search Report and Written Opinion for Application No. PCT/US2020/022710, mailed Jun. 3, 2020.

(Continued)

*Primary Examiner* — Bao Q Li

(74) *Attorney, Agent, or Firm* — Wolf, Greenfield & Sacks, P.C.

(57) ABSTRACT

Provided herein are methods and compositions for inducing in a subject abroad neutralizing antibody response to human immunodeficiency virus (HIV) infection.

21 Claims, 12 Drawing Sheets

Specification includes a Sequence Listing.

(56) References Cited

U.S. PATENT DOCUMENTS

| | | | |
|---|---|---|---|
| 9,255,126 | B2 | 2/2016 | Polo et al. |
| 9,267,114 | B2 | 2/2016 | Yamshchikov et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,512,456 | B2 | 12/2016 | Wang et al. |
| 9,533,047 | B2 | 1/2017 | de Fougerolles et al. |
| 9,572,896 | B2 | 2/2017 | Bancel et al. |
| 9,597,380 | B2 | 3/2017 | Chakraborty et al. |
| 9,669,089 | B2 | 6/2017 | Thess et al. |
| 9,675,668 | B2 | 6/2017 | Bancel et al. |
| 9,868,691 | B2 | 1/2018 | Benenato et al. |
| 9,868,692 | B2 | 1/2018 | Benenato et al. |
| 9,872,900 | B2 | 1/2018 | Ciaramella et al. |
| 9,950,068 | B2 | 4/2018 | de Fougerolles et al. |
| 10,022,435 | B2 | 7/2018 | Ciaramella et al. |
| 10,023,626 | B2 | 7/2018 | Bolen et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,232,055 | B2 | 3/2019 | Kariko et al. |
| 10,273,269 | B2 | 4/2019 | Ciaramella |
| 10,286,086 | B2 | 5/2019 | Roy et al. |
| 10,323,076 | B2 | 6/2019 | Ellsworth et al. |
| 10,385,088 | B2 | 8/2019 | Fraley et al. |
| 10,442,756 | B2 | 10/2019 | Benenato et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,653,712 | B2 | 5/2020 | Hoge |
| 10,653,767 | B2 | 5/2020 | Ciaramella et al. |
| 10,695,419 | B2 | 6/2020 | Ciaramella et al. |
| 10,709,779 | B2 | 7/2020 | Ciaramella et al. |
| 10,857,105 | B2 | 12/2020 | Benenato et al. |
| 10,898,574 | B2 | 1/2021 | de Fougerolles et al. |
| 10,925,958 | B2 | 2/2021 | Ciaramella |
| 11,027,025 | B2 | 6/2021 | Hoge et al. |
| 11,045,540 | B2 | 6/2021 | Ciaramella |
| 11,103,578 | B2 | 8/2021 | Ciaramella et al. |
| 11,351,242 | B1 | 6/2022 | Lori et al. |
| 11,384,352 | B2 | 7/2022 | Miracco |
| 11,406,703 | B2 | 8/2022 | Kramarczyk et al. |
| 11,464,848 | B2 | 10/2022 | Ciaramella et al. |
| 11,485,960 | B2 | 11/2022 | Dousis et al. |
| 11,497,807 | B2 | 11/2022 | Ciaramella et al. |
| 11,564,893 | B2 | 1/2023 | Smith |
| 11,576,961 | B2 | 2/2023 | Ciaramella et al. |
| 11,643,441 | B1 | 5/2023 | Ciaramella et al. |
| 11,696,946 | B2 | 7/2023 | Ciaramella |
| 2001/0001066 | A1 | 5/2001 | Cezayirli et al. |
| 2002/0147167 | A1 | 10/2002 | Armstrong et al. |
| 2003/0032615 | A1 | 2/2003 | Felgner et al. |
| 2003/0050468 | A1 | 3/2003 | Shiver et al. |
| 2003/0092653 | A1 | 5/2003 | Kisich et al. |
| 2004/0005667 | A1 | 1/2004 | Ratti et al. |
| 2004/0132683 | A1 | 7/2004 | Felgner et al. |
| 2005/0032730 | A1 | 2/2005 | Von Der Mulbe et al. |
| 2005/0059624 | A1 | 3/2005 | Hoerr et al. |
| 2005/0170508 | A1 | 8/2005 | Huang et al. |
| 2005/0250723 | A1 | 11/2005 | Hoerr et al. |
| 2006/0172003 | A1 | 8/2006 | Meers et al. |
| 2006/0172966 | A1 | 8/2006 | Lipford et al. |
| 2007/0280929 | A1 | 12/2007 | Hoerr et al. |
| 2007/0292453 | A1 | 12/2007 | Floyd et al. |
| 2008/0025944 | A1 | 1/2008 | Hoerr et al. |
| 2008/0171079 | A1 | 7/2008 | Hanon et al. |
| 2008/0171711 | A1 | 7/2008 | Hoerr et al. |
| 2009/0098162 | A1 | 4/2009 | Freiman et al. |
| 2009/0148467 | A1 | 6/2009 | Friedman et al. |
| 2009/0305324 | A1 | 12/2009 | Kuzushima et al. |
| 2010/0112042 | A1 | 5/2010 | Polisky et al. |
| 2010/0130588 | A1 | 5/2010 | Yaworski et al. |
| 2010/0189729 | A1 | 7/2010 | Hoerr et al. |
| 2010/0203076 | A1 | 8/2010 | Fotin-Mleczek et al. |
| 2010/0239608 | A1 | 9/2010 | Von Der Mulbe et al. |
| 2010/0249208 | A1 | 9/2010 | Hecker et al. |
| 2010/0291156 | A1 | 11/2010 | Barner et al. |
| 2010/0303851 | A1 | 12/2010 | Hoerr et al. |
| 2010/0305196 | A1 | 12/2010 | Probst et al. |
| 2010/0330122 | A1 | 12/2010 | Smith et al. |
| 2011/0117125 | A1 | 5/2011 | Hope et al. |
| 2011/0250225 | A1 | 10/2011 | Fotin-Mleczek et al. |
| 2011/0269950 | A1 | 11/2011 | Von Der Mulbe et al. |
| 2011/0311472 | A1 | 12/2011 | Hoerr et al. |
| 2012/0009221 | A1 | 1/2012 | Hoerr et al. |
| 2012/0101148 | A1 | 4/2012 | Aking et al. |
| 2012/0189700 | A1 | 7/2012 | Aguilar et al. |
| 2012/0219573 | A1 | 8/2012 | Baumhof et al. |
| 2012/0232133 | A1 | 9/2012 | Balazs et al. |
| 2012/0258046 | A1 | 10/2012 | Mutske |
| 2012/0328655 | A1 | 12/2012 | Dubensky et al. |
| 2013/0022538 | A1 | 1/2013 | Rossi |
| 2013/0028925 | A1 | 1/2013 | Friedman et al. |
| 2013/0102034 | A1 | 4/2013 | Schrum et al. |
| 2013/0121988 | A1 | 5/2013 | Hoerr et al. |
| 2013/0142818 | A1 | 6/2013 | Baumhof et al. |
| 2013/0156849 | A1 | 6/2013 | De Fougerolles et al. |
| 2013/0171234 | A1 | 7/2013 | Fairman et al. |
| 2013/0171241 | A1 | 7/2013 | Geall |
| 2013/0183355 | A1 | 7/2013 | Jain et al. |
| 2013/0189351 | A1 | 7/2013 | Geall |
| 2013/0195867 | A1 | 8/2013 | Hoerr et al. |
| 2013/0195967 | A1 | 8/2013 | Guild et al. |
| 2013/0195968 | A1 | 8/2013 | Geall et al. |
| 2013/0195969 | A1 | 8/2013 | Geall et al. |
| 2013/0202684 | A1 | 8/2013 | Geall et al. |
| 2013/0209454 | A1 | 8/2013 | Diskin et al. |
| 2013/0236533 | A1 | 9/2013 | Von Andrian et al. |
| 2013/0236974 | A1 | 9/2013 | De Fougerolles |
| 2013/0243848 | A1 | 9/2013 | Lobovkina et al. |
| 2013/0245103 | A1 | 9/2013 | de Fougerolles et al. |
| 2013/0245107 | A1 | 9/2013 | de Fougerolles et al. |
| 2013/0259923 | A1 | 10/2013 | Bancel et al. |
| 2013/0266640 | A1 | 10/2013 | De Fougerolles et al. |
| 2013/0295043 | A1 | 11/2013 | Kallen et al. |
| 2013/0336998 | A1 | 12/2013 | Kallen et al. |
| 2014/0037660 | A1 | 2/2014 | Folin-Mleczek et al. |
| 2014/0065228 | A1 | 3/2014 | Yarowoski et al. |
| 2014/0127247 | A1 | 5/2014 | Dubensky et al. |
| 2014/0134201 | A1 | 5/2014 | Tureci et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0206753 | A1 | 7/2014 | Guild et al. |
| 2014/0271829 | A1 | 9/2014 | Lilja et al. |
| 2014/0308304 | A1 | 10/2014 | Manoharan et al. |
| 2014/0378538 | A1 | 12/2014 | Bancel |
| 2015/0051268 | A1 | 2/2015 | Bancel et al. |
| 2015/0056253 | A1 | 2/2015 | Bancel et al. |
| 2015/0064242 | A1 | 3/2015 | Heyes et al. |
| 2015/0118183 | A1 | 4/2015 | Baumhof et al. |
| 2015/0141499 | A1 | 5/2015 | Bancel et al. |
| 2015/0307542 | A1 | 10/2015 | Roy et al. |
| 2015/0315541 | A1 | 11/2015 | Bancel et al. |
| 2015/0376115 | A1 | 12/2015 | Ansell et al. |
| 2016/0024140 | A1 | 1/2016 | Issa et al. |
| 2016/0024141 | A1 | 1/2016 | Issa et al. |
| 2016/0151284 | A1 | 1/2016 | Heyes et al. |
| 2016/0032273 | A1 | 2/2016 | Shahrokh et al. |
| 2016/0038612 | A1 | 2/2016 | Hoge et al. |
| 2016/0130308 | A1 | 5/2016 | Weiner et al. |
| 2016/0194368 | A1 | 7/2016 | Hoge et al. |
| 2016/0243221 | A1 | 8/2016 | Hoge et al. |
| 2016/0271272 | A1 | 9/2016 | Bancel et al. |
| 2016/0303224 | A1 | 10/2016 | Kanekiyo et al. |
| 2016/0317647 | A1 | 11/2016 | Ciaramella et al. |
| 2016/0331828 | A1 | 11/2016 | Ciaramella et al. |
| 2016/0367658 | A1 | 12/2016 | Kinney et al. |
| 2017/0043037 | A1 | 2/2017 | Kariko et al. |
| 2017/0065675 | A1 | 3/2017 | Bancel et al. |
| 2017/0202979 | A1 | 7/2017 | Chakraborty et al. |

(56) References Cited

U.S. PATENT DOCUMENTS

| | | | |
|---|---|---|---|
| 2017/0204152 | A1 | 7/2017 | Nelson et al. |
| 2017/0210698 | A1 | 7/2017 | Benenato et al. |
| 2017/0239371 | A1 | 8/2017 | Guild et al. |
| 2017/0130255 | A1 | 10/2017 | Wang et al. |
| 2017/0340724 | A1 | 11/2017 | Ciaramella et al. |
| 2017/0340725 | A1 | 11/2017 | Ciaramella et al. |
| 2018/0000953 | A1 | 1/2018 | Almarsson et al. |
| 2018/0002393 | A1 | 1/2018 | Bancel et al. |
| 2018/0008700 | A1 | 1/2018 | Heineman et al. |
| 2018/0028645 | A1 | 2/2018 | Ciaramella et al. |
| 2018/0028664 | A1 | 2/2018 | Besin et al. |
| 2018/0078634 | A1 | 3/2018 | Ogembo et al. |
| 2018/0147298 | A1 | 5/2018 | Besin et al. |
| 2018/0214537 | A1 | 8/2018 | Mutzke et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273977 | A1 | 9/2018 | Mousavi et al. |
| 2018/0274009 | A1 | 9/2018 | Marquardt et al. |
| 2018/0280496 | A1 | 10/2018 | Ciaramella et al. |
| 2018/0289792 | A1 | 10/2018 | Ciaramella et al. |
| 2018/0296663 | A1 | 10/2018 | Hipp et al. |
| 2018/0303925 | A1 | 10/2018 | Weissman et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0312549 | A1 | 11/2018 | Ciaramella |
| 2018/0318409 | A1 | 11/2018 | Valiante et al. |
| 2018/0363019 | A1 | 12/2018 | Hoge |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0008948 | A1 | 1/2019 | Ciaramella et al. |
| 2019/0015501 | A1 | 1/2019 | Ciaramella et al. |
| 2019/0085368 | A1 | 3/2019 | Bancel et al. |
| 2019/0099481 | A1 | 4/2019 | Ciaramella et al. |
| 2019/0125839 | A1 | 5/2019 | Frederick et al. |
| 2019/0167811 | A1 | 6/2019 | Benenato et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0274968 | A1 | 9/2019 | Weissman et al. |
| 2019/0275170 | A1 | 9/2019 | Benenato et al. |
| 2019/0298657 | A1 | 10/2019 | Martini et al. |
| 2019/0298658 | A1 | 10/2019 | Benenato |
| 2019/0300906 | A1 | 10/2019 | Martini et al. |
| 2019/0314292 | A1 | 10/2019 | Benenato et al. |
| 2019/0314493 | A1 | 10/2019 | Ciaramella et al. |
| 2019/0336452 | A1 | 11/2019 | Brader |
| 2019/0336595 | A1 | 11/2019 | Ciaramella |
| 2019/0351040 | A1 | 11/2019 | Valiante et al. |
| 2019/0367561 | A1 | 12/2019 | Cui et al. |
| 2019/0382774 | A1 | 12/2019 | Hoge et al. |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1 | 3/2020 | Smith et al. |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129445 | A1 | 4/2020 | Patel et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0164059 | A1 | 5/2020 | Mcguire et al. |
| 2020/0172928 | A1 | 6/2020 | Yao |
| 2020/0239869 | A1 | 7/2020 | Issa et al. |
| 2020/0254086 | A1 | 8/2020 | Hoge et al. |
| 2020/0276295 | A1 | 9/2020 | Ogembo et al. |
| 2020/0282047 | A1 | 9/2020 | Ciaramella et al. |
| 2020/0306191 | A1 | 10/2020 | Schariter et al. |
| 2020/0338004 | A1 | 10/2020 | Hansson et al. |
| 2020/0338190 | A1 | 10/2020 | Ciaramella et al. |
| 2020/0368162 | A1 | 11/2020 | Martini |
| 2021/0046173 | A1 | 2/2021 | Ciaramella et al. |
| 2021/0087135 | A1 | 3/2021 | Benenato et al. |
| 2021/0163919 | A1 | 6/2021 | Issa et al. |
| 2021/0187097 | A1 | 6/2021 | Ciaramella et al. |
| 2021/0206818 | A1 | 7/2021 | Huang et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0309976 | A1 | 10/2021 | Dousis et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0062408 | A1 | 3/2022 | Kramarczyk et al. |
| 2022/0125899 | A1 | 4/2022 | Ashburn et al. |
| 2022/0145381 | A1 | 5/2022 | Elich et al. |
| 2022/0236253 | A1 | 7/2022 | Hopson |
| 2022/0241399 | A1 | 8/2022 | Lusso et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2023/0000970 | A1 | 1/2023 | Nachbagauer et al. |
| 2023/0142529 | A1 | 5/2023 | White et al. |
| 2023/0181481 | A1 | 6/2023 | White et al. |
| 2023/0190761 | A1 | 6/2023 | Brader et al. |
| 2023/0212645 | A1 | 7/2023 | Marquardt et al. |

FOREIGN PATENT DOCUMENTS

| | | | |
|---|---|---|---|
| CA | 2473135 | A1 | 6/2003 |
| DE | 10 2004 035227 | A1 | 2/2006 |
| EP | 0969862 | B2 | 1/2000 |
| EP | 1083232 | B1 | 2/2005 |
| EP | 1301614 | B1 | 11/2006 |
| EP | 1383556 | B1 | 10/2007 |
| EP | 1905844 | A2 | 2/2008 |
| EP | 1026253 | B2 | 12/2012 |
| EP | 2188379 | B1 | 1/2013 |
| EP | 2548960 | A1 | 1/2013 |
| WO | WO 1987/005326 | A1 | 9/1987 |
| WO | WO 1990/011092 | A1 | 10/1990 |
| WO | WO 1991/007425 | A1 | 5/1991 |
| WO | WO 1992/019752 | A1 | 11/1992 |
| WO | WO 1993/014778 | A1 | 8/1993 |
| WO | WO 1993/015749 | A1 | 8/1993 |
| WO | WO 1995/027069 | A1 | 3/1995 |
| WO | WO 1995/024485 | A2 | 9/1995 |
| WO | WO 1995/026204 | A1 | 10/1995 |
| WO | WO 1995/033835 | A1 | 12/1995 |
| WO | WO 1997/48370 | A1 | 12/1997 |
| WO | WO 1998/020016 | A1 | 5/1998 |
| WO | WO 1998/34640 | A1 | 8/1998 |
| WO | WO 1998/47913 | A2 | 10/1998 |
| WO | WO 1999/033982 | A2 | 7/1999 |
| WO | WO 1999/052503 | A2 | 10/1999 |
| WO | WO 2000/029561 | A1 | 5/2000 |
| WO | WO 2000/063364 | A2 | 10/2000 |
| WO | WO 2001/021810 | A1 | 3/2001 |
| WO | WO 2001/093836 | A2 | 12/2001 |
| WO | WO 2004/058166 | A2 | 7/2004 |
| WO | WO 2004/076645 | A1 | 9/2004 |
| WO | WO 2005/007689 | A1 | 1/2005 |
| WO | WO 2005/009346 | A1 | 2/2005 |
| WO | WO 2005/034992 | A2 | 4/2005 |
| WO | WO 2005/120152 | A1 | 12/2005 |
| WO | WO 2006/020071 | A2 | 2/2006 |
| WO | WO 2006/056027 | A1 | 6/2006 |
| WO | WO 2006/071903 | A1 | 7/2006 |
| WO | WO 2006/095259 | A1 | 9/2006 |
| WO | WO 2007/095976 | A2 | 8/2007 |

(56) References Cited

FOREIGN PATENT DOCUMENTS

| | | | |
|---|---|---|---|
| WO | WO 2008/011609 | A1 | 1/2008 |
| WO | WO 2008/014979 | A3 | 2/2008 |
| WO | WO 2008/052770 | A2 | 5/2008 |
| WO | WO 2008/083949 | A2 | 7/2008 |
| WO | WO 2009/030254 | A1 | 3/2009 |
| WO | WO 2009/030481 | A1 | 3/2009 |
| WO | WO 2009/095226 | A1 | 8/2009 |
| WO | WO 2009/127230 | A1 | 10/2009 |
| WO | WO 2010/037408 | A1 | 4/2010 |
| WO | WO 2010/037539 | A1 | 4/2010 |
| WO | WO 2010/042877 | A1 | 4/2010 |
| WO | WO 2010/054406 | A1 | 5/2010 |
| WO | WO 2010/088927 | A1 | 8/2010 |
| WO | WO 2010/115046 | A2 | 10/2010 |
| WO | WO 2011/005799 | A2 | 1/2011 |
| WO | WO 2011/106607 | A1 | 2/2011 |
| WO | WO 2011/026641 | A9 | 3/2011 |
| WO | WO 2011/068810 | A1 | 6/2011 |
| WO | WO 2011/069529 | A1 | 6/2011 |
| WO | WO 2011/069586 | A1 | 6/2011 |
| WO | WO 2012/024629 | A1 | 8/2011 |
| WO | WO 2011/144358 | A1 | 11/2011 |
| WO | WO 2018/232357 | A1 | 12/2011 |
| WO | WO 2012/006369 | A2 | 1/2012 |
| WO | WO 2012/006376 | A2 | 1/2012 |
| WO | WO 2012/006380 | A2 | 1/2012 |
| WO | WO 2012/019630 | A1 | 2/2012 |
| WO | WO 2012/019780 | A1 | 2/2012 |
| WO | WO 2012/030904 | A2 | 3/2012 |
| WO | WO 2012/051211 | A1 | 4/2012 |
| WO | WO 2012/075040 | A2 | 6/2012 |
| WO | WO 2012/089225 | A1 | 7/2012 |
| WO | WO 2012/106377 | A3 | 8/2012 |
| WO | WO 2012/113513 | A1 | 8/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2012/149376 | A2 | 11/2012 |
| WO | WO 2013/006825 | A1 | 1/2013 |
| WO | WO 2013/006834 | A1 | 1/2013 |
| WO | WO 2013/006837 | A1 | 1/2013 |
| WO | WO 2013/006838 | A1 | 1/2013 |
| WO | WO 2013/006842 | A2 | 1/2013 |
| WO | WO 2013/019669 | A2 | 2/2013 |
| WO | WO 2013/030778 | A2 | 3/2013 |
| WO | WO 2013/052167 | A2 | 4/2013 |
| WO | WO 2013/055905 | A1 | 4/2013 |
| WO | WO 2013/056132 | A2 | 4/2013 |
| WO | WO 2013/059496 | A1 | 4/2013 |
| WO | WO 2013/074696 | A1 | 5/2013 |
| WO | WO 2013/086373 | A1 | 6/2013 |
| WO | WO 2013/090186 | A1 | 6/2013 |
| WO | WO 2013/090648 | A1 | 6/2013 |
| WO | WO 2013/102203 | A1 | 7/2013 |
| WO | WO 2013/109604 | A1 | 7/2013 |
| WO | WO 2013/112778 | A1 | 8/2013 |
| WO | WO 2013/113502 | A1 | 8/2013 |
| WO | WO 2013/120497 | A1 | 8/2013 |
| WO | WO 2013/120628 | A1 | 8/2013 |
| WO | WO 2013/120629 | A1 | 8/2013 |
| WO | WO 2013/143555 | A1 | 10/2013 |
| WO | WO 2013/174409 | A1 | 11/2013 |
| WO | WO 2013/185069 | A1 | 12/2013 |
| WO | WO 2014/039185 | A1 | 3/2014 |
| WO | WO 2014/063059 | A1 | 4/2014 |
| WO | WO 2014/071963 | A1 | 5/2014 |
| WO | WO 2014/072061 | A1 | 5/2014 |
| WO | WO 2014/089239 | A1 | 6/2014 |
| WO | WO 2014/089486 | A1 | 6/2014 |
| WO | WO 2014/093924 | A1 | 6/2014 |
| WO | WO 2014/127917 | A1 | 8/2014 |
| WO | WO 2014/136086 | A1 | 9/2014 |
| WO | WO 2014/144196 | A1 | 9/2014 |
| WO | WO 2014/152027 | A1 | 9/2014 |
| WO | WO 2014/152774 | A1 | 9/2014 |
| WO | WO 2014/152940 | A1 | 9/2014 |
| WO | WO 2014/159813 | A1 | 10/2014 |
| WO | WO 2014/160243 | A1 | 10/2014 |
| WO | WO 2015/005253 | A1 | 1/2015 |
| WO | WO 2015/013551 | A1 | 1/2015 |
| WO | WO 2015/024667 | A1 | 2/2015 |
| WO | WO 2015/024668 | A2 | 2/2015 |
| WO | WO 2015/054639 | A1 | 4/2015 |
| WO | WO 2015/164674 | A1 | 4/2015 |
| WO | WO 2015/110659 | A1 | 7/2015 |
| WO | WO 2015/130584 | A2 | 9/2015 |
| WO | WO 2015/134332 | A2 | 9/2015 |
| WO | WO 2015/143193 | A1 | 9/2015 |
| WO | WO 2015/189425 | A1 | 12/2015 |
| WO | WO 2015/199952 | A1 | 12/2015 |
| WO | WO 2016/044023 | A1 | 3/2016 |
| WO | WO 2016/057912 | A1 | 4/2016 |
| WO | WO 2016/092460 | A2 | 6/2016 |
| WO | WO 2016/116904 | A1 | 7/2016 |
| WO | WO 2016/149384 | A1 | 9/2016 |
| WO | WO 2016/164762 | A1 | 10/2016 |
| WO | WO 2016/176330 | A1 | 11/2016 |
| WO | WO 2016/184822 | A1 | 11/2016 |
| WO | WO 2016/201377 | A1 | 12/2016 |
| WO | WO 2016/203025 | A1 | 12/2016 |
| WO | WO 2017/011773 | A2 | 1/2017 |
| WO | WO 2017/015457 | A1 | 1/2017 |
| WO | WO 2017/015463 | A1 | 1/2017 |
| WO | WO 2017/019935 | A1 | 2/2017 |
| WO | WO 2017/020026 | A1 | 2/2017 |
| WO | WO 2017/021546 | A1 | 2/2017 |
| WO | WO 2017/031232 | A1 | 2/2017 |
| WO | WO 2017/031241 | A1 | 2/2017 |
| WO | WO 2017/049245 | A2 | 3/2017 |
| WO | WO 2017/062513 | A1 | 4/2017 |
| WO | WO 2017/066789 | A1 | 4/2017 |
| WO | WO 2017/070601 | A1 | 4/2017 |
| WO | WO 2017/070616 | A1 | 4/2017 |
| WO | WO 2017/070618 | A1 | 4/2017 |
| WO | WO 2017/070620 | A1 | 4/2017 |
| WO | WO 2017/070622 | A1 | 4/2017 |
| WO | WO 2017/070623 | A1 | 4/2017 |
| WO | WO 2017/070624 | A1 | 4/2017 |
| WO | WO 2017/075531 | A1 | 5/2017 |
| WO | WO 2017/109222 | A1 | 6/2017 |
| WO | WO 2017/112865 | A1 | 6/2017 |
| WO | WO 2017/127750 | A1 | 7/2017 |
| WO | WO 2017/140905 | A1 | 8/2017 |
| WO | WO 2017/147458 | A1 | 8/2017 |
| WO | WO 2017/162265 | A1 | 9/2017 |
| WO | WO 2017/165317 | A1 | 9/2017 |
| WO | WO 2017/201333 | A1 | 11/2017 |
| WO | WO 2017/201340 | A1 | 11/2017 |
| WO | WO 2017/201342 | A1 | 11/2017 |
| WO | WO 2017/201347 | A1 | 11/2017 |
| WO | WO 2017/201349 | A1 | 11/2017 |
| WO | WO 2017/208191 | A1 | 12/2017 |
| WO | WO 2017/210215 | A1 | 12/2017 |
| WO | WO 2017/210364 | A1 | 12/2017 |
| WO | WO 2016/091391 | A1 | 2/2018 |
| WO | WO 2018/020271 | A1 | 2/2018 |
| WO | WO 2018/052549 | A1 | 3/2018 |
| WO | WO 2018/053209 | A1 | 3/2018 |
| WO | WO 2018/075980 | A1 | 4/2018 |
| WO | WO 2018/078053 | A1 | 5/2018 |
| WO | WO 2018/081459 | A1 | 5/2018 |
| WO | WO 2018/081462 | A1 | 5/2018 |
| WO | WO 2018/081638 | A1 | 5/2018 |
| WO | WO 2018/089851 | A1 | 5/2018 |
| WO | WO 2018/091540 | A1 | 5/2018 |
| WO | WO 2018/107088 | A1 | 6/2018 |
| WO | WO 2018/111967 | A1 | 6/2018 |
| WO | WO 2018/132537 | A1 | 7/2018 |
| WO | WO 2018/140733 | A1 | 8/2018 |
| WO | WO 2018/144082 | A1 | 8/2018 |
| WO | WO 2018/144778 | A1 | 8/2018 |
| WO | WO 2018/151816 | A1 | 8/2018 |
| WO | WO 2018/157009 | A1 | 8/2018 |

(56) References Cited

FOREIGN PATENT DOCUMENTS

| | | | |
|---|---|---|---|
| WO | WO 2018/170245 | A1 | 9/2018 |
| WO | WO 2018/170256 | A1 | 9/2018 |
| WO | WO 2018/170260 | A1 | 9/2018 |
| WO | WO 2018/170270 | A1 | 9/2018 |
| WO | WO 2018/170347 | A1 | 9/2018 |
| WO | WO 2018/175783 | A1 | 9/2018 |
| WO | WO 2018/187590 | A2 | 10/2018 |
| WO | WO 2018/200737 | A1 | 11/2018 |
| WO | WO 2018/232355 | A1 | 12/2018 |
| WO | WO 2019/036670 | A1 | 2/2019 |
| WO | WO 2019/036682 | A1 | 2/2019 |
| WO | WO 2019/036683 | A1 | 2/2019 |
| WO | WO 2019/036685 | A1 | 2/2019 |
| WO | WO 2019/055807 | A1 | 3/2019 |
| WO | WO 2019/055887 | A1 | 3/2019 |
| WO | WO 2019/103993 | A1 | 5/2019 |
| WO | WO 2019/148101 | A1 | 8/2019 |
| WO | WO 2019/195314 | A2 | 10/2019 |
| WO | WO 2020/006242 | A1 | 1/2020 |
| WO | WO 2020/056370 | A1 | 3/2020 |
| WO | WO 2020/061284 | A1 | 3/2020 |
| WO | WO 2020/061295 | A1 | 3/2020 |
| WO | WO 2020/061367 | A1 | 3/2020 |
| WO | WO 2020/097291 | A1 | 5/2020 |
| WO | WO 2020/172239 | A1 | 8/2020 |
| WO | WO 2020/185811 | A1 | 9/2020 |
| WO | WO 2020/190750 | A1 | 9/2020 |
| WO | WO 2020/243561 | A1 | 12/2020 |
| WO | WO 2021/030533 | A1 | 2/2021 |
| WO | WO 2021/050864 | A1 | 3/2021 |
| WO | WO 2021/055811 | A1 | 3/2021 |
| WO | WO 2021/155243 | A1 | 8/2021 |
| WO | WO 2021/155274 | A1 | 8/2021 |
| WO | WO 2021/159040 | A2 | 8/2021 |
| WO | WO 2021/159130 | A2 | 8/2021 |
| WO | WO 2021/211343 | A1 | 10/2021 |
| WO | WO 2021/222304 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/247817 | A1 | 12/2021 |
| WO | WO 2022/032154 | A2 | 2/2022 |
| WO | WO 2022/067010 | A1 | 3/2022 |
| WO | WO 2022/150717 | A1 | 7/2022 |
| WO | WO 2022/155524 | A1 | 7/2022 |
| WO | WO 2022/155530 | A1 | 7/2022 |
| WO | WO 2022/187698 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A2 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/232585 | A1 | 11/2022 |
| WO | WO 2022/241103 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A2 | 1/2023 |
| WO | WO 2023/283645 | A1 | 1/2023 |
| WO | WO 2023/283651 | A1 | 1/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |
| WO | WO 2023/092069 | A1 | 5/2023 |
| WO | WO 2023/107999 | A2 | 6/2023 |
| WO | WO 2023/114307 | A1 | 6/2023 |
| WO | WO 2023/132885 | A1 | 7/2023 |
| WO | WO 2023/137149 | A1 | 7/2023 |

OTHER PUBLICATIONS

[No Author Listed], "Messenger RNA", Internet: Wikipedia. Jun. 19, 2013, XP002699196, Retrieved from the Internet: URL: http://en.wikipedia.org/wiki/Messenger RNA.

Adamiak, et al. glycoprotein E [Human alphaherpesvirus 2]. GenBank: ABU45436.1. Pub. Nov. 29, 2007. 1 page.

Ajbani et al., Immunogenicity of Semliki Forest Virus Based Self-Amplifying RNA Expressing Indian HIV-1C Genes in Mice. Int J Biol Macromol. Nov. 2015;81:794-802. doi: 10.1016/j.ijbiomac.2015.09.010. Epub Sep. 8, 2015.

Alconada et al., A tyrosine-based motif and a casein kinase II phosphorylation site regulate the intracellular trafficking of the varicella-zoster virus glycoprotein I, a protein localized in the trans-Golgi network. EMBO J. Nov. 15, 1996;15(22):6096-110.

Anderson et al., Incorporation of pseudouridine into mRNA enhances translation by diminishing PKR activation, Nucleic Acids Res. Sep. 2010;38(17):5884-92. doi: 10.1093/nar/gkq347. Epub May 10, 2010.

Anderson et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.

Archer, Induction of a T-cell specific antigen on bone marrow lymphocytes with thymus RNA. Immunology. Jan. 1978;34(1):123-9.

Ashley et al., Bone marrow-generated dendritic cells pulsed with tumor extracts or tumor RNA induce antitumor immunity against central nervous system tumors. J Exp Med. Oct. 6, 1997; 186(7): 1177-82.

Awasthi et al., Nucleoside-modified mRNA encoding HSV-2 glycoproteins C, D, and E prevents clinical and subclinical genital herpes. Sci Immunol. Sep. 20, 2019;4(39):eaaw7083.

Awasthi et al., A paradigm shift: vaccine-induced antibodies as an immune correlate of protection against herpes simplex virus type 1 genital herpes. J Infect Dis. Mar. 2014;209(6):813-5. doi: 10.1093/infdis/jit658. Epub Nov. 27, 2013.

Awasthi et al., An HSV-2 Trivalent Vaccine Is Immunogenic in Rhesus Macaques and Highly Efficacious in Guinea Pigs. PLoS Pathog. Jan. 19, 2017;13(1):e1006141. doi: 10.1371/journal.ppat.1006141. eCollection Jan. 2017.

Awasthi et al., Immunization With a Vaccine Combining Herpes Simplex Virus 2 (HSV-2) Glycoprotein C (gC) and gD Subunits Improves the Protection of Dorsal Root Ganglia in Mice and Reduces the Frequency of Recurrent Vaginal Shedding of HSV-2 DNA in Guinea Pigs Compared to Immunization With gD Alone. J Virol . Oct. 2011;85(20):10472-86. doi: 10.1128/JVI.00849-11. Epub Aug. 3, 2011.

Azarkh et al. Synthesis and decay of varicella zoster virus transcripts. J Neurovirol. Jun. 2011;17(3):281-7. doi: 10.1007/s13365-011-0029-2. Epub Apr. 1, 20112.

Bahl et al., Preclinical and Clinical Demonstration of Immunogenicity by mRNA Vaccines against H10N8 and H7N9 Influenza Viruses. Mol Ther. Jun. 7, 2017;25(6):1316-1327. doi: 10.1016/j.ymthe.2017.03.035. Epub Apr. 27, 2017.

Balazs et al., Vectored immunoprophylaxis protects humanized mice from mucosal HIV transmission. Nat Med. Mar. 2014;20(3):296-300. doi: 10.1038/nm.3471. Epub Feb. 9, 2014. Author Manuscript, 17 pages.

Barouch et al., Therapeutic efficacy of potent neutralizing HIV-1-specific monoclonal antibodies in SHIV-infected rhesus monkeys. Nature. Nov. 14, 2013;503(7475):224-8. doi: 10.1038/nature12744. Epub Oct. 30, 2013. Author Manuscript, 24 pages.

Belliveau, N.M., et al., Microfluidic synthesis of highly potent limit-size lipid nanoparticles for in vivo delivery of siRNA. Mol Ther Nucleic Acids. Aug. 2012; 1(8): e37.

Bettinger et al., Peptide-mediated RNA delivery: a novel approach for enhanced transfection of primary and post-mitotic cells. Nucleic Acids Res. Sep. 15, 2001;29(18):3882-91.

Bogers et al., Potent immune responses in rhesus macaques induced by nonviral delivery of a self-amplifying RNA vaccine expressing HIV type 1 envelope with a cationic nanoemulsion. J Infect Dis. Mar. 15, 2015;211(6):947-55. doi: 10.1093/infdis/jiu522. Epub Sep. 18, 2014.

(56) References Cited

OTHER PUBLICATIONS

Bonehill et al., Single-step antigen loading and activation of dendritic cells by mRNA electroporation for the purpose of therapeutic vaccination in melanoma patients. Clin Cancer Res. May 2009; 15(10): 3366-3375.
Borza et al., Use of gHgL for attachment of Epstein-Barr virus to epithelial cells compromises infection. J Virol. May 2004;78(10):5007-14. doi: 10.1128/jvi.78.10.5007-5014.2004.
Bose et al., Influence of cationic lipid concentration on properties of lipid-polymer hybrid nanospheres for gene delivery. Int J Nanomedicine. Sep. 2, 2015;10:5367-82. doi: 10.2147/IJN.S87120. eCollection 2015.
Bowie et al., Deciphering the message in protein sequences: tolerance to amino acid substitutions. Science. Mar. 16, 1990;247(4948):1306-10.
Bridge et al., Heterologous prime-boost-boost immunisation of Chinese cynomolgus macaques using DNA and recombinant poxvirus vectors expressing HIV-1 virus-like particles. Virol J. Sep. 7, 2011;8:429. doi: 10.1186/1743-422X-8-429.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Brito et al., Self-amplifying mRNA vaccines. Adv Genet. 2015;89:179-233. doi: 10.1016/bs.adgen.2014.10.005. Epub Dec. 4, 2014.
Burton et al., Efficient neutralization of primary isolates of HIV-1 by a recombinant human monoclonal antibody. Science. Nov. 11, 1994;266(5187):1024-7. doi: 10.1126/science.7973652.
Cairns et al., Patient-Specific Neutralizing Antibody Responses to Herpes Simplex Virus Are Attributed to Epitopes on gD, gB, or Both and Can Be Type Specific. J Virol. Sep. 2015;89(18):9213-31. doi: 10.1128/JVI.01213-15. Epub Jun. 24, 2015.
Chahal et al., An RNA nanoparticle vaccine against Zika virus elicits antibody and CD8+ T cell responses in a mouse model. Sci Rep. Mar. 21, 2017;7(1):252. doi: 10.1038/s41598-017-00193-w.
Chattopadhyay et al., A chimeric vesiculo/alphavirus is an effective alphavirus vaccine. J Virol. Jan. 2013;87(1):395-402.
Chen et al., Human monoclonal antibodies targeting the haemagglutinin glycoprotein can neutralize H7N9 influenza virus. Nat Commun. Mar. 30, 2015;6:6714. doi: 10.1038/ncomms7714.
Chen et al., Influence of Particle Size on the in Vivo Potency of Lipid Nanoparticle Formulations of siRNA. J Control Release. Aug. 10, 2016;235:236-244. doi: 10.1016/j.jconrel.2016.05.059. Epub May 26, 2016.
Cheng et al., Multifunctional triblock copolymers for intracellular messenger RNA delivery. Biomaterials. Oct. 2012; 33(28): 6868-6876.
Cohen et al., Vaccine Development for Epstein-Barr Virus.Adv Exp Med Biol. 2018;1045:477-493. doi: 10.1007/978-981-10-7230-7_22.
Cohen, Epstein-barr virus vaccines. Clin Transl Immunology. Jan. 23, 2015;4(1):e32. doi: 10.1038/cti.2014.27. eCollection Jan. 2015.
Conry et al., Characterization of a messenger RNA polynucleotide vaccine vector. Cancer Res. Apr. 1, 1995 ;55 (7):1397-1400.
Cross, Without these lipid shells, there would be no mRNA vaccines for COVID-19. Chem Eng News. Mar. 6, 2021; 99(8). 4 pages.
Cu et al., Enhanced Delivery and Potency of Self-Amplifying mRNA Vaccines by Electroporation in Situ, Vaccines, 2013, 1, 367-383. Abstract Only.
Cuchet et al., Characterization of anti proliferative and cytotoxic properties of the HSV-1 immediate-early ICPo protein. J Gene Med. Sep. 2005;7(9):1187-99. doi: 10.1002/jgm.761.
Cui et al., Rabbits immunized with Epstein-Barr virus gH/gL or gB recombinant proteins elicit higher serum virus neutralizing activity than gp350. Vaccine. Jul. 25, 2016;34(34):4050-5. doi: 10.1016/j.vaccine.2016.06.021. Epub Jun. 10, 2016.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Cunnigham, The herpes zoster subunit vaccine. Expert Opin Biol Ther. 2016;16(2):265-71. doi: 10.1517/14712598.2016.1134481. PMID: 26865048.
Dahlman et al., In vivo endothelial siRNA delivery using polymeric nanoparticles with low molecular weight. Nat Nanotechnol. Aug. 2014;9(8):648-655. doi: 10.1038/nnano.2014.84. Epub May 11, 2014.
Daubeuf et al., HSV ICP0 recruits USP7 to modulate TLR-mediated innate response. Blood. Apr. 2, 2009;113(14):3264-75. Epub Oct. 24, 2008.
Davison, envelope glycoprotein D [Human alphaherpesvirus 2]. NCBI Reference Sequence: YP 009137218.1. May 12, 2015. 3 pages.
De Jong et al., Drug delivery and nanoparticles:applications and hazards. Int J Nanomedicine. 2008;3(2):133-49.
De La Pena et al., Immunogenicity in Rabbits of HIV-1 SOSIP Trimers from Clades A, B, and C, Given Individually, Sequentially, or in Combination. J Virol. Mar. 28, 2018;92(8):e01957-17. doi: 10.1128/JVI.01957-17. Print Apr. 15, 2018.
De Lucca, FL et al., Effect of the calcium phosphate-mediated RNA uptake on the transfer of cellular immunity of a synthetic peptide of HIV-1 to human lymphocytes by exogenous RNA. Mol Cell Biochem. Dec. 2001;228(1-2):9-14. doi: 10.1023/a:1013305708539.
Deering et al., Nucleic acid vaccines: prospects for non-viral delivery of mRNA vaccines.Expert Opin Drug Deliv. Jun. 2014;11(6):885-99. doi: 10.1517/17425247.2014.901308. Epub Mar. 26, 2014.
Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015. Review.
Dropulic et al., The challenge of developing a herpes simplex virus 2 vaccine. xpert Rev Vaccines. Dec. 2012; 11(12):1429-40. doi:10.1586/erv.12.129.
Durbin et al., RNAs Containing Modified Nucleotides Fail To Trigger RIG-I Conformational Changes for Innate Immune Signaling. mBio. Sep. 20, 2016;7(5):e00833-16. doi: 10.1128/mBio.00833-16.
Dutton et al., A novel DNA vaccine technology conveying protection against a lethal herpes simplex viral challenge in mice. PLoS One. Oct. 3, 2013;8(10):e76407. doi: 10.1371/journal.pone.0076407. eCollection 2013.
Egan et al., An HSV-2 nucleoside-modified mRNA genital herpes vaccine containing glycoproteins gC, gD, and gE protects mice against HSV-1 genital lesions and latent infection. PLoS Pathog. Jul. 27, 2020;16(7):e1008795.
Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.
Escalante et al., A Pentavalent Epstein-Barr Virus-Like Particle Vaccine Elicits High Titers of Neutralizing Antibodies against Epstein-Barr Virus Infection in Immunized Rabbits. Vaccines (Basel). Apr. 6, 2020;8(2):169. doi: 10.3390/vaccines8020169.
Everett et al., Herpes simplex virus type 1 regulatory protein ICP0 aids infection in cells with a preinduced interferon response but does not impede interferon-induced gene induction. J Viral. May 2009;83(10):4978-83. doi: 10.1128/JV1.02595-08. Epub Mar. 4, 2009.
Ewert et al., Cationic liposome-nucleic acid complexes for gene delivery and silencing: pathways and mechanisms for plasmid DNA and siRNA. Top Curr Chem. 2010;296:191-226.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Furuichi et al., Viral and cellular mRNA capping: past and prospects. Adv Virus Res. 2000;55:135-84. doi: 10.1016/s0065-3527(00)55003-9.

(56) References Cited

OTHER PUBLICATIONS

Furuichi, Caps on Eukaryotic mRNAs. eLS. John Wiley & Sons. Jul. 2014. 1-12.
Gaskell et al., Feline herpesvirus. Vet Res. Mar.-Apr. 2007;38(2):337-54. Epub Feb. 13, 2007.
Geall et al., Nonviral delivery of self-amplifying RNA vaccines. Proc Natl Acad Sci U S A. Sep. 4, 2012;109(36):14604-9. doi:10. 1073/pnas. 1209367109. Epub Aug. 20, 2012.
Gilboa et al., Cancer immunotherapy with mRNA-transfected dendritic cells. Immunol Rev. Jun. 2004;199:251-63.
Gjetting et al., In vitro and in vivo effects of polyethylene glycol (PEG)-modified lipid in DOTAP/cholesterol-mediated gene transfection. Int J Nanomedicine. Aug. 9, 2010;5:371-83.
Gorander et al., Secreted portion of glycoprotein g of herpes simplex virus type 2 is a novel antigen for type-discriminating serology. J Clin Microbiol. Aug. 2003;41(8):3681-6.
Grabbe et al., Translating nanoparticulate-personalized cancer vaccines into clinical applications: case study with RNA-lipoplexes for the treatment of melanoma. Nanomedicine (Lond). Oct. 2016;11(20):2723-2734.
Gram et al., Immunological analysis of a Lactococcus lactis-based DNA vaccine expressing HIV gp120. Genet Vaccines Ther. Jan. 29, 2007;5:3. doi: 10.1186/1479-0556-5-3.
Gupta et al., TcVac3 induced control of Trypanosoma cruzi infection and chronic myocarditis in mice. PLoS One. 2013;8(3):e59434. doi: 10.1371/journal.pone.0059434. Epub Mar. 26, 2013.
Haas et al., Codon usage limitation in the expression of HIV-1 envelope glycoprotein. Curr Biol. Mar. 1, 1996;6(3):315-24. doi: 10.1016/s0960-9822(02)00482-7.
Haddad et al., Depletion of glycoprotein gp85 from virosomes made with Epstein-Barr virus proteins abolishes their ability to fuse with virus receptor-bearing cells. J Virol. Dec. 1989;63(12):4998-5005. doi: 10.1128/JVI.63.12.4998-5005.1989.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013. 07.002. Epub Jul. 17, 2013.
Hagglund et al., Role of ICP0 in the strategy of conquest of the host cell by herpes simplex virus 1. J Viral. Mar. 2004;78(5): 2169-78. doi: 10.1128/jvi.78.5.2169-2178.2004.
Hajj et al., Tools for translation: non-viral materials for therapeutic mRNA delivery. Nat Rev Mat. Sep. 2017;2:17056.
Halford et al., ICP0 antagonizes Stat 1-dependent repression of herpes simplex virus: implications for the regulation of viral latency. Viral J. Jun. 9, 2006;3:44.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
Hecker et al., Non-Viral DNA and mRNA Gene Delivery to the CNS Pre-Operatively for Neuroprotection and Following Neurotrauma. Molecular Therapy. 2004; 9, S258-S258.
Hecker, Nonviral, cationic lipid-mediated delivery of mRNA. Methods Mol Biol. 2013;969:73-88. doi: 10.1007/978-1-62703-260-5_5.
Heidenreich et al., A novel RNA-based adjuvant combines strong immunostimulatory capacities with a favorable safety profile. Int J Cancer. Jul. 15, 2015;137(2):372-84. doi: 10.1002/ijc.29402. Epub Jan. 8, 2015.
Heiser et al., Induction of polyclonal prostate cancer-specific CTL using dendritic cells transfected with amplified tumor RNA. J Immunol. Mar. 1, 2001; 166(5):2953-60.
Hess et al., Vaccination with mRNAs encoding tumor-associated antigens and granulocyte-macrophage colony-stimulating factor efficiently primes CTL responses, but is insufficient to overcome tolerance to a model tumor/self antigen. Cancer Immunol Immunother. Jun. 2006;55(6):672-83. Epub Aug. 20, 2005.
Heyes et al., Cationic lipid saturation influences intracellular delivery of encapsulated nucleic acids. J Control Release. Oct. 3, 2005;107(2):276-87.
Hobbs et al., Efficient activation of viral genomes by levels of herpes simplex virus ICP0 insufficient to affect cellular gene expression or cell survival. J Viral. Apr. 2001;75(7):3391-403. doi: 10.1128/ JVI. 75. 7.3391-3403.2001.
Hodgman et al. RecName: Full=Envelope glycoprotein I; Short=gl; Flags: Precursor. UniProtKB/Swiss-Prot: P06764.1. Rev. Jan. 10, 2015. 1 page.
Hoerr et al., In vivo application of RNA leads to induction of specific cytotoxic T lymphocytes and antibodies. EurJ Immunol. Jan. 2000;30(1):1-7.
Hoerr et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp et al., Modification of antigen-encoding RNA increases stability, translational efficacy, and T-cell stimulatory capacity of dendritic cells. Blood. Dec. 15, 2006;108(13):4009-17.
Hori et al., Antitumor Activity of Cationic Liposome-Mediated Bax mRNA Transfer in HOSM-1 Mandibular Osteoosarcoma Cells: A Comparative Study of Local Administration and Systemic Administration. Journal of Oral and Maxillofacial Surgery, 2014, vol. 72, No. 9, SUPPL. 1, p. e107, Abstract No. 98.
Hsu et al., Cationic lipid nanoparticles for therapeutic delivery of siRNA and miRNA to murine liver tumor. Nanomedicine. Nov. 2013;9(8):1169-80. doi: 10.1016/j.nano.2013.05.007. Epub May 30, 2013.
Ito et al., Full-length EBNA1 mRNA-transduced dendritic cells stimulate cytotoxic T lymphocytes recognizing a novel HLA-Cw*0303- and -Cw*0304-restricted epitope on EBNA1-expressing cells.J Gen Virol. Mar. 2007;88(Pt 3):770-80.
Jirikowski et al., Reversal of diabetes insipidus in Brattleboro Rats: Intrahypothalamic injection of vasopressin mRNA. Science. Feb. 1992; 255(5047): 996-998.
Jochum et al., RNAs in Epstein-Barr virions control early steps of infection. Proc Natl Acad Sci U S A. May 22, 2012;109(21):E1396-404. doi: 10.1073/pnas.1115906109. Epub Apr. 27, 2012.
John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018. 01.029. Epub Feb. 15, 2018.
Johnston et al., Status of vaccine research and development of vaccines for herpes simplex virus. Vaccine. Jun. 3, 2016;34(26):2948-2952. doi: 10.1016/j.vaccine.2015.12.076. Epub Mar. 11, 2016.
Julien et al., Broadly neutralizing antibody PGT121 allosterically modulates CD4 binding via recognition of the HIV-1 gp120 V3 base and multiple surrounding glycans. PLoS Pathog. 2013;9(5):e1003342. doi: 10.1371/journal.ppat. 1003342. Epub May 2, 2013.
Kalantari-Dehagi et al., Discovery of Potential Diagnostic and Vaccine Antigens in Herpes Simplex Virus 1 and 2 by Proteome-Wide Antibody Profiling. J Virol. Apr. 2012;86(8):4328-39. doi: 10.1128/JVI.05194-11. Epub Feb. 8, 2012.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/ 2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kanapathipillai et al., Nanoparticle targeting of anti-cancer drugs that alter intracellular signaling or influence the tumor microenvironment. Adv Drug Deliv Rev. Dec. 15, 2014;79-80:107-18. doi: 10.1016/j.addr.2014.05.005. Epub May 9, 2014.
Kariko et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.

(56) References Cited

OTHER PUBLICATIONS

Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.

Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.

Kauffman et al., Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. Epub Oct. 20, 2015.

Khanna et al., Vaccine strategies against Epstein-Barr virus-associated diseases: lessons from studies on cytotoxic T-cell-mediated immune regulation. Immunol Rev. Aug. 1999; 170:49-64. doi: 10.1111/j.1600-065x.1999.tb01328.x.

Kirschner et al., Soluble Epstein-Barr virus glycoproteins gH, gL, and gp42 form a 1:1:1 stable complex that acts like soluble gp42 in B-cell fusion but not in epithelial cell fusion. J Virol. Oct. 2006;80(19):9444-54. doi: 10.1128/JVI.00572-06.

Kisich et al., Antimycobacterial agent based on mRNA encoding human beta-defensin 2 enables primary macrophages to restrict growth of Mycobacterium tuberculosis.Infect Immun. Apr. 2001;69(4):2692-9.

Klasse et al., Sequential and Simultaneous Immunization of Rabbits with HIV-1 Envelope Glycoprotein SOSIP.664 Trimers from Clades A, B and C. PLoS Pathog. Sep. 14, 2016;12(9):e1005864. doi: 10.1371/journal.ppat.1005864. eCollection Sep. 2016.

Koelle et al., Recent progress in herpes simplex virus immunobiology and vaccine research. Clin Microbiol Rev. Jan. 2003;16(1):96-113. doi: 10.1128/CMR.16.1.96-113.2003.

Kofler et al., Mimicking live flavivirus immunization with a non-infectious RNA vaccine. Proc. Natl. Acad. Sci. U S A. Feb. 2004;101(7):1951-1956.

Kohl et al., Limited antibody-dependent cellular cytotoxicity antibody response induced by a herpes simplex virus type 2 subunit vaccine. J Infect Dis. Jan. 2000;181(1):335-9. doi: 10.1086/315208.

Kozielski et al., Bioreducible Cationic Polymer-Based Nanoparticles for Efficient and Environmentally Triggered Cytoplasmic siRNA Delivery to Primary Human Brain Cancer Cells, ACS Nano. Apr. 22, 2014;8(4):3232-41. doi: 10.1021/nn500704t. Epub Apr. 3, 2014.

Kreiter et al., Intranodal vaccination with naked antigen-encoding RNA elicits potent prophylactic and therapeutic antitumoral immunity. Cancer Res. 2010; 70: 9031-9040.

Kreiter et al., Tumor vaccination using messenger RNA: prospects of a future therapy. Curr Opinion in Immun. Jun. 2011; 23(3): 399-406.

Krisky et al., Deletion of multiple immediate-early genes from herpes simplex virus reduces cytotoxicity and permits long-term gene expression in neurons. Gene Ther. Dec. 1998;5(12):1593-603.

Kuhn et al., mRNA as a versatile tool for exogenous protein expression. Current Gene Therapy. Oct. 2012; 12 (5): 347-361.

Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.

Kurimoto et al., PEG-OligoRNA Hybridization of mRNA for Developing Sterically Stable Lipid Nanoparticles toward In Vivo Administration. Molecules. Apr. 3, 2019;24(7): 1303.

Kusakabe et al., The timing of GM-CSF expression plasmid administration influences the Th1/Th2 response induced by an HIV-1-specific DNA vaccine. J Immunol. Mar. 15, 2000;164(6):3102-11. doi: 10.4049/jimmunol.164.6.3102.

Kussie et al., A single engineered amino acid substitution changes antibody fine specificity. J Immunol. Jan. 1, 1994;152(1):146-52.

Kwoh et al., Transcription-based amplification system and detection of amplified human immunodeficiency virus type 1 with a bead-based sandwich hybridization format. Proc Natl Acad Sci U S A. Feb. 1989;86(4):1173-7. doi: 10.1073/pnas.86.4.1173.

Kwok et al., Genomic sequencing and comparative analysis of Epstein-Barr virus genome isolated from primary nasopharyngeal carcinoma biopsy. PLoS One. 2012;7(5):e36939. doi: 10.1371/journal.pone.0036939. Epub May 10, 2012.

Kwong et al., Broadly neutralizing antibodies and the search for an HIV-1 vaccine: the end of the beginning. Nat Rev Immunol. Sep. 2013;13(9):693-701. doi: 10.1038/nri3516.

Lanfranca et al., HSV-1 ICP0: An E3 Ubiquitin Ligase That Counteracts Host Intrinsic and Innate Immunity. Cells. May 20, 2014;3(2):438-54.

Ledford, H., Supercharged Antibodies Fight HIV-Related Virus in Monkeys, Nature. News & Comment. Oct. 30, 2013. 4 pages. doi: 10.1038/nature.2013.14060.

Leitner et al., DNA and RNA-based vaccines: principles, progress and prospects. Vaccine. Dec. 10, 1999;18 (9-10):765-77.

Leroueil et al., Wide varieties of cationic nanoparticles induce defects in supported lipid bilayers. Nano Lett. Feb. 2008;8(2):420-4. doi: 10.1021/n10722929. Epub Jan. 25, 2008.

Li et al., Developing lipid nanoparticle-based siRNA therapeutics for hepatocellular carcinoma using an integrated approach. Mol Cancer Ther. Nov. 2013;12(11):2308-18. doi: 10.1158/1535-7163.MCT-12-0983-T. Epub Aug. 13, 2013.

Li et al., Overcoming obstacles to develop effective and safe siRNA therapeutics. Expert Opin Biol Ther. May 2009; 9(5): 609-19.

Lian et al., Trends and developments in liposome drug delivery systems. J Pharm Sci. Jun. 2001;90(6):667-80.

Liang et al., Efficient Targeting and Activation of Antigen-Presenting Cells In Vivo after Modified mRNA Vaccine Administration in Rhesus Macaques. Mol Ther. Dec. 6, 2017;25(12):2635-2647. doi: 10.1016/j.ymthe.2017.08.006. Epub Aug. 12, 2017.

Lin et al., Lipid-based nanoparticles in the systemic delivery of siRNA. Nanomedicine (Lond). Jan. 2014;9(1):105-20. doi: 10.2217/nnm.13.192.

Lindgren et al., Induction of Robust B Cell Responses after Influenza mRNA Vaccination Is Accompanied by Circulating Hemagglutinin-Specific ICOS+PD-1+CXCR3+T Follicular Helper Cells. Front Immunol. Nov. 13, 2017;8:1539. doi: 10.3389/fimmu.2017.01539. eCollection 2017.

Liu et al., Human herpesvirus 2 strain 16293 glycoprotein D (US6) gene, complete cds. GenBank: AY779754. Encodes AAW23134. Apr. 14, 2009.

Lohith, In vivo imaging of mRNA based vaccine antigen in non-human primates using PET reporter mRNA-probe combination, Molecular Imaging and Biology, Dec. 2017, vol. 19, No. 1 Supplement, Page S703.

Loparev, Unknown [Human alphaherpesvirus 3]. Gen Bank: ABE03086.1. Dep Apr. 15, 2007. (Year: 2007).

Lorenzi et al., Intranasal vaccination with messenger RNA as a new approach in gene therapy: Use against tuberculosis. BMC Biotechnol. Oct. 2010; 10(77): 1-11.

MacLachlan, Lipid Nanoparticle-mediated delivery of messenger RNA. Presentation. 1st International mRNA Health Conference. Tubingen, Germany. Oct. 24, 2013. http://files.shareholder.com/downloads/ABEA-50QJTB/2628241206x0x699789/47543d12-db34-4e6e-88a9-f3ae5d97b1d2/MacLachlan_mRNA_Conf_2013.pdf. Last accessed Dec. 22, 2016.

Madden et al., Administration of nucleoside-modified mRNA encoding broadly neutralizing antibody protects humanized mice from HIV-1 challenge. Nat Commun. Mar. 2, 2017;8:14630. doi: 10.1038/ncomms14630. Available at https://acuitastx.com/wp-content/uploads/2015/01/Poster-Second-International-mRNA-Health-Conference.pdf.

Madden et al., Systemic delivery of mRNA therapeutics using lipid nanoparticles (LNP): improved potency for novel LNP and influence of route of administration on protein expression. 2nd International mRNA Health Conference. Nov. 12, 2014. https://acuitastx.com/wp-content/uploads/2015/01/Poster-Second-International-mRNA-Health-Conference.pdf. 1 page.

Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.

(56) References Cited

OTHER PUBLICATIONS

Maier et al., Biodegradable Lipids Enabling Rapidly Eliminated Lipid Nanoparticles for Systemic Delivery of RNAi Therapeutics. Mol Ther. Aug. 2013; 21(8): 1570-1578.
Martinon et al., Induction of virus-specific cytotoxic T lymphocytes in vivo by liposome-entrapped mRNA. EurJ Immunol. Jul. 1993;23(7):1719-22.
McAllister et al., Prospects and perspectives for development of a vaccine against herpes simplex virus infections. Expert Rev Vaccines. Nov. 2014;13(11):1349-60. doi: 10.1586/14760584.2014.932694. Epub Jul. 31, 2014.
McCafferty et al., In Vivo Validation of a Reversible Small Molecule-Based Switch for Synthetic Self-Amplifying mRNA Regulation. Mol Ther. Mar. 3, 2021;29(3):1164-1173. doi: 10.1016/j.ymthe.2020.11.010. Epub Nov. 11, 2020.
McClements et al., Immunization with DNA vaccines encoding glycoprotein Dor glycoprotein B, alone or in combination, induces protective immunity in animal models of herpes simplex virus-2 disease. Proc Natl Acad Sci U Sa. Oct. 15, 1996;93(21):11414-20.
McKenzie et al., Nucleic acid vaccines: tasks and tactics. Immunol Res. 2001;24(3):225-44.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell et al., RNA transfected dendritic cells as cancer vaccines. Curr Opin Mal Ther. Apr. 2000;2(2):176-81.
Mitchell et al., RNA-transfected dendritic cells in cancer immunotherapy. J Clin Invest. Nov. 2000;106 (9):1065-9.
Miyagawa et al., Herpes simplex viral-vector design for efficient transduction of nonneuronal cells without cytotoxicity. Proc Natl Acad Sci U Sa. Mar. 31, 2015 ;112(13):E1632-41. Epub Mar. 16, 2015. (Year: 2015).
Mockey et al., mRNA-based cancer vaccine: prevention of B16 melanoma progression and metastasis by systemic injection of MART1 mRNA histidylated lipopolyplexes. Cancer Gene Ther. Sep. 2007;14(9):802-14. Epub Jun. 22, 2007.
Moffat et al., Functions of the C-terminal domain of varicella-zoster virus glycoprotein E in viral replication in vitro and skin and T-cell tropism in vivo. J Virol. Nov. 2004;78(22):12406-15.
Molesworth et al., Epstein-Barr virus gH is essential for penetration of B cells but also plays a role in attachment of virus to epithelial cells. J Virol. Jul. 2000;74(14):6324-32. doi: 10.1128/jvi.74.14.6324-6332.2000.
Monslow et al., Immunogenicity generated by mRNA vaccine encoding VZV gE antigen is comparable to adjuvanted subunit vaccine and better than live attenuated vaccine in nonhuman primates. Vaccine. Aug. 10, 2020;38(36):5793-5802. doi: 10.1016/j.vaccine.2020.06.062. Epub Jul. 20, 2020.
Morello et al., Immunization With Herpes Simplex Virus 2 (HSV-2) Genes Plus Inactivated HSV-2 Is Highly Protective Against Acute and Recurrent HSV-2 Disease. J Virol. Apr. 2011;85(7):3461-72. doi: 10.1128/JVI.02521-10. Epub Jan. 26, 2011.
Mosca et al., Activation of human immunodeficiency virus by herpesvirus infection: identification of a region within the long terminal repeat that responds to a trans-acting factor encoded by herpes simplex virus 1. Proc Natl Acad Sci U S A. Nov. 1987;84(21):7408-12. doi: 10.1073/pnas.84.21.7408.
Mosca et al., Activation of human immunodeficiency virus by herpesvirus infection: identification of a region within the long terminal repeat that responds to a trans-acting factor encoded by herpes simplex virus 1. Proc Natl Acad Sci USA. Nov. 1987;84(21):7408-12.
Muller et al., Transfection of dendritic cells with RNA induces CD4- and COB-mediated T cell immunity against breast carcinomas and reveals the immunodominance of presented T cell epitopes. J Immunol. Jun. 15, 2003;170 (12):5892-6.
Murakawa et al., Direct detection of HIV-1 RNA from AIDS and ARC patient samples. DNA. May 1988;7(4):287-95. doi: 10.1089/dna.1988.7.287.
Natuk et al., Recombinant vesicular stomatitis virus vectors expressing herpes simplex virus type 2 gD elicit robust CD4+Th1 immune responses and are protective in mouse and guinea pig models of vaginal challenge. J Viral. May 2006;80(9):4447-57.
Paladino et al., Cellular localization of the herpes simplex virus ICP0 protein dictates its ability to block IRF3-mediated innate immune responses. PLoS One. Apr. 29, 2010;5(4):e10428.
Pardi et al., Administration of nucleoside-modified mRNA encoding broadly neutralizing antibody protects humanized mice from HIV-1 challenge. Nat Commun. Mar. 2, 2017;8:14630. doi: 10.1038/ncomms14630.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Parisien et al., Rationalization and prediction of selective decoding of pseudouridine-modified nonsense and sense codons. RNA. Mar. 2012;18(3):355-67. doi: 10.1261/rna.031351.111. Epub Jan. 26, 2012.
Perche et al., Enhancement of dendritic cells transfection in vivo and of vaccination against B16F10 melanoma with mannosylated histidylated lipopolyplexes loaded with tumor antigen messenger RNA. Nanomedicine. Aug. 2011;7(4):445-53. doi: 10.1016/j.nano.2010.12.010. Epub Jan. 8, 2011.
Perez et al. Novel Epstein-Barr virus-like particles incorporating gH/gL-EBNA1 or GB-LMP2 induce high neutralizing antibody titers and EBV-specific T-cell responses in immunized mice. Oncotarget. Mar. 21, 2017;8(12):19255-19273. doi: 10.18632/oncotarget.13770.
Petro et al., Herpes simplex type 2 virus deleted in glycoprotein D protects against vaginal, skin and neural disease. Elife. Mar. 10, 2015;4:e06054. doi: 10.7554/eLife.06054.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Pollard et al., Type I IFN counteracts the induction of antigen-specific immune responses by lipid-based delivery of mRNA vaccines. Mol Ther. Jan. 2013; 21 (1): 251-259.
Poveda et al., Establishing Preferred Product Characterization for the Evaluation of RNA Vaccine Antigens. Vaccines (Basel). Sep. 27, 2019;7(4):131. doi: 10.3390/vaccines7040131.
Pulford et al., Liposome-siRNA-peptide complexes cross the blood-brain barrier and significantly decrease PrP'C on neuronal cells and PrP'RES in infected cell cultures. PLoS One. 201 O; 5(6): e11085.
Rabinovich et al., Synthetic messenger RNA as a tool for gene therapy. Hum. Gene Ther. Oct. 2006; 17: 1027-1035.
Reichmuth et al., mRNA Vaccine Delivery Using Lipid Nanoparticles. Ther Deliv. 2016;7(5):319-34. doi: 10.4155/tde-2016-0006.
Rittig et al., Intradermal vaccinations with RNA coding for TAA generate CD8+and CD4+immune responses and induce clinical benefit in vaccinated patients. Mol Ther. May 2011;19(5):990-9. doi: 10.1038/mt.2010.289. Epub Dec. 28, 2010.
Rodriguez et al., Delivery of recombinant vaccines against bovine herpesvirus type 1 gD and Babesia bovis MSA-2c to mice using liposomes derived from egg yolk lipids. Vet J. Jun. 2013;196(3):550-1. doi: 10.1016/j.tvjl.2012.10.036. Epub Nov. 24, 2012.
Rodriguez et al., The HSV-1 ubiquitin ligase ICP0: Modifying the cellular proteome to promote infection. Virus Res. Aug. 2020;285:198015. Epub May 13, 2020.
Rouse et al., Induction in vitro of primary cytotoxic T-lymphocyte responses with DNA encoding herpes simplex virus proteins. J Virol. Sep. 1994;68(9):5685-9.
Routy et al. Immunologic activity and safety of autologous HIV RNA-electroporated dendritic cells in HIV-1 infected patients receiving antiretroviral therapy. Clin Immunol. Feb. 2010;134(2):140-7. doi: 10.1016/j.clim.2009.09.009. Epub Nov. 4, 2009.

(56) References Cited

OTHER PUBLICATIONS

Samaniego et al., The herpes simplex virus immediate-early protein ICP0 affects transcription from the viral genome and infected-cell survival in the absence of ICP4 and ICP27. J Viral. Jun. 1997;71(6):4614-25.
Sathiyamoorthy et al., Inhibition of EBV-mediated membrane fusion by anti-gHgL antibodies. Proc Natl Acad Sci U S A. Oct. 10, 2017;114(41):E8703-E8710. doi: 10.1073/pnas.1704661114. Epub Sep. 22, 2017.
Sayour et al., RNA Nanoparticle Vaccines Facilitate and Sustain Adoptive Cellular Therapy Targeting Pediatric Intracranial Malignancies. Pediatric Blood and Cancer, Jun. 2015, vol. 62, Supplement 2, p. S24, Abstract No. 4012.
Scheid et al., Sequence and structural convergence of broad and potent HIV antibodies that mimic CD4 binding. Science. Sep. 16, 2011;333(6049):1633-7. doi: 10.1126/science.1207227. Epub Jul. 14, 2011.
Schirrmacher et al., Intra-pinna anti-tumor vaccination with self-replicating infectious RNA or with DNA encoding a model tumor antigen and a cytokine. Gene Ther. Jul. 2000;7(13):1137-47.
Schlake et al., Developing mRNA-vaccine technologies. RNA Biol. Nov. 2012;9(11):1319-30. doi: 10.4161/rna.22269. Epub Oct. 12, 2012.
Schmidt-Chanasit, glycoprotein B [Human alphaherpesvirus 2]. Gen Bank: ADG45118.1. Jun. 24, 2010. 2 pages.
Schmitt et al., In vitro induction of a bladder cancer-specific T-cell response by mRNA- transfected dendritic cells. J Cancer Res Clin Oncol. 2001 ;127(3):203-6.
Schott et al., Viral and non-viral approaches for transient delivery of mRNA and proteins. Current Gene Ther. 2011; 11 (5): 382-398.
Schwendener, Liposomes as vaccine delivery systems: a review of the recent advances. Ther Adv Vaccines. Nov. 2014;2(6):159-82. doi: 10.1177/2051013614541440.
Sciortino et al., RNAs extracted from herpes simplex virus 1 virions: apparent selectivity of viral but not cellular RNAs packaged in virions. J Virol. Sep. 2001;75(17):8105-16.
Segura et al., Monitoring gene therapy by external imaging of mRNA: Pilot study on murine erythropoietin. Ther Drug Monit. Oct. 2007; 29(5): 612-8.
Sekulovich et al., The herpes simplex virus type 1 alpha protein ICP27 can act as a trans-repressor or a trans-activator in combination with ICP4 and ICP0. J Viral. Dec. 1988;62(12):4510-22. doi: 10.1128/JV1.62.12.4510-4522.1988.
Shah et al., Shingrix for Herpes Zoster: A Review. Skin Therapy Lett. Jul. 2019;24(4):5-7.
Shingai et al., Antibody-mediated immunotherapy of macaques chronically infected with SHIV suppresses viraemia. Nature. Nov. 14, 2013;503(7475):277-80. doi: 10.1038/nature12746. Epub Oct. 30, 2013.
Small et al., Viruses—from pathogens to vaccine carriers.Curr Opin Virol. Oct. 2011;1(4):241-5. doi: 10.1016/j.coviro.2011.07.009.
Smits et al. RNA-based gene transfer for adult stem cells and T cells. Leukemia. 2004; 18: 1898-1902.
Sohn et al., In-vivo particle mediated delivery of mRNA to mammalian tissues: ballistic and biological effects. Wound Rep and Regen. Jul.-Aug. 2001; 287-296.
Sohn et al., Measurement of CD8+ and CD4+ T Cell Frequencies Specific for EBV LMP1 and LMP2a Using mRNA-Transfected DCs.PLoS One. May 29, 2015;10(5):e0127899. doi: 10.1371/journal.pone.0127899. eCollection 2015.
Stanberry et al., Glycoprotein-D-adjuvant vaccine to prevent genital herpes. N Engl J Med. Nov. 21, 2002;347(21):1652-61.
Strong et al., Incorporation of beta-globin untranslated regions into a Sindbis virus vector for augmentation of heterologous mRNA expression. Gene Ther. Jun. 1997;4(6):624-7.
Su et al., Antigen presenting cells transfected with LMP2a RNA induce CD4+LMP2a-specific cytotoxic T lymphocytes which kill via a Fas-independent mechanism.Leuk Lymphoma. Aug. 2002;43(8):1651-62.
Sullenger et al., Emerging clinical applications of RNA. Nature. Jul. 11, 2002;418(6894):252-8.
Svinarchuk et al., Inhibition of HIV proliferation in MT-4 cells by antisense oligonucleotide conjugated to lipophilic groups. Biochimie. 1993;75(1-2):49-54. doi: 10.1016/0300-9084(93)90024-m.
Swain et al. RecName: Full=Envelope glycoprotein C; Flags: Precursor UniProtKB/Swiss-Prot: P06475.1. Rev. Jan. 7, 2015. 3 pages.
Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni et al., Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Tavernier et al., mRNA as gene therapeutic: How to control protein expression. J. of Controlled Release. Mar. 2011; 150(3): 238-247.
Taylor et al., Therapeutic vaccination strategies to treat nasopharyngeal carcinoma. Chin Clin Oncol. Apr. 2016;5(2):23. doi: 10.21037/cco.2016.03.20.
Tekmira, Lipid Nanoparticle-mediated delivery of messenger RNA (retrieved from the internet). Published Oct. 24, 2013. Available at http://files.shareholder.com/downloads/ABEA-50QJTB/2628241206x0x699789/47543d12-db34-4e6e-88a9-f3ae5d97b1d2/MacLachlan_mRNA_Conf_2013.pdf.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Teufel et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64.doi: 10.1038/mt.2015.103. Epub Jun. 8, 2015.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Uzgun, S., et al., PEGylation improves nanoparticle formation and transfection efficiency of messenger RNA. Pharm Res. Sep. 2011; 28(9); 2223-2232.
Vassilev et al., Microparticle-mediated RNA immunization against bovine viral diarrhea virus. Vaccine. Feb. 28, 2001;19(15-16):2012-9.
Wang et al., Epstein-Barr virus lacking glycoprotein gp42 can bind to B cells but is not able to infect. J Virol. Jan. 1998;72(1):158-63. doi: 10.1128/JVI.72.1.158-163.1998.
Wang et al., Essential role played by the C-terminal domain of glycoprotein I in envelopment of varicella-zoster virus in the trans-Golgi network: interactions of glycoproteins with tegument. J Virol. Jan. 2001;75(1):323-40.
Wang et al., Gene inoculation generates immune responses against human immunodeficiency virus type 1. Proc Natl Acad Sci U S A. May 1, 1993;90(9):4156-60. doi: 10.1073/pnas.90.9.4156.
Wang et al., Immune Responses to Varicella-Zoster Virus Glycoprotein E Formulated with Poly(Lactic-co-Glycolic Acid) Nanoparticles and Nucleic Acid Adjuvants in Mice. Virol Sin. Aug. 5, 2020. doi: 10.1007/s12250-020-00261-y.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Weilhammer et al., The use of nanolipoprotein particles to enhance the immunostimulatory properties of innate immune agonists against

(56) References Cited

OTHER PUBLICATIONS lethal influenza challenge. Biomaterials. Dec. 2013;34(38):10305-18. doi: 10.1016/j.biomaterials.2013.09.038. Epub Sep. 27, 2013.
Weissman et al., Dendritic cells express and use multiple HIV coreceptors. Adv Exp Med Biol. 1997;417:401-6. doi: 10.1007/978-1-4757-9966-8_65.
Weissman et al., HIV GAG mRNA transfection of dendritic cells (DC) delivers encoded antigen to MHC class I and II molecules, causes DC maturation, and induces a potent human in vitro primary immune response. J Immunol. Oct. 15, 2000;165(8):4710-7. doi: 10.4049/jimmunol.165.8.4710.
Whisnant et al., Integrative functional genomics decodes herpes simplex virus 1. Nat Commun. Apr. 27, 2020;11 (1):2038. (Year: 2020).
Whitley et al., Clinical management of herpes simplex virus infections: past, present, and future. Version 1. F1000Res. 2018; 7: F1000 Faculty Rev-1726.
Wilkinson et al., Structure of the Fab fragment of F105, a broadly reactive anti-human immunodeficiency virus (HIV) antibody that recognizes the CD4 binding site of HIV type 1 gp120. J Virol. Oct. 2005;79(20):13060-9. doi: 10.1128/JVI.79.20.13060-13069.2005.
Winkler et al., Changing the antigen binding specificity by single point mutations of an anti-p24 (HIV-1) antibody. J Immunol. Oct. 15, 2000;165(8):4505-14. doi: 10.4049/jimmunol.165.8.4505.
Winkler et al., Changing the antigen binding specificity by single point mutations of an anti-p24 (HIV-1) antibody. J Immunol. Oct. 15, 2000;165(8):4505-14.
Wong et al., An mRNA vaccine for influenza. Nat Biotechnol. Dec. 2012;30(12):1202-4. doi: 10.1038/nbt.2439.
Woodberry et al., Immunogenicity of a human immunodeficiency virus (HIV) polytope vaccine containing multiple HLA A2 HIV CD8(+) cytotoxic T-cell epitopes. J Virol. Jul. 1999;73(7):5320-5. doi: 10.1128/JVI.73.7.5320-5325.1999.
Wu et al., Prolonged gene expression and cell survival after infection by a herpes simplex virus mutant defective in the immediate-early genes encoding ICP4, ICP27, and ICP22. J Viral. Sep. 1996;70(9):6358-69. (Year: 1996).
Xue et al., Lipid-Based Nanocarriers for RNA Delivery. Curr Pharm Des. 2015;21(22):3140-7.
Yamamoto et al., Current prospects for mRNA gene delivery. Eur J Pharm Biopharm. Mar. 2009;71(3):484-9. doi: 10.1016/j.ejpb.2008.09.016. Epub Oct. 10, 2008.
Ying et al., Cancer therapy using a self-replicating RNA vaccine. Nat Med. Jul. 1999;5(7):823-7.
Zhao et al., Chapter Two: Lipid Nanoparticles for Gene Delivery. Book: Advances in Genetics. Elsevier, 2014. 24 pages.
Zhao et al., Nanoparticle vaccines. Vaccine. Jan. 9, 2014;32(3):327-37. doi: 10.1016/j.vaccine.2013.11.069. Epub Dec. 2, 2013.
Zhou et al., RNA melanoma vaccine: induction of antitumor immunity by human glycoprotein 100 mRNA immunization. Hum Gene Ther. Nov. 1, 1999;10(16):2719-24.
Zhu et al., Targeting of glycoprotein I (gE) of varicella-zoster virus to the trans-Golgi network by an AYRV sequence and an acidic amino acid-rich patch in the cytosolic domain of the molecule. J Virol. Oct. 1996;70(10):6563-75.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.
Zwick et al., Identification and characterization of a peptide that specifically binds the human, broadly neutralizing anti-human immunodeficiency virus type 1 antibody b12. J Virol. Jul. 2001;75(14):6692-9. doi: 10.1128/JVI.75.14.6692-6699.2001.
Zwick et al., Molecular features of the broadly neutralizing immunoglobulin G1 b12 required for recognition of human immunodeficiency virus type 1 gp120. J Virol. May 2003;77(10):5863-76. doi: 10.1128/jvi.77.10.5863-5876.2003.

A. Increased gp120 and p24 WB bands in VLPs produced in the presence of furin

B. Increased Gag content and PG16-mediated capture in concentrated VLPs produced in the presence of furin

CDH3 length: 13-52 aa. (average 18.4)

HIV RNA VACCINES

RELATED APPLICATION

This application is a national stage filing under 35 U.S.C. § 371 of International Application No. PCT/US2020/022710, filed Mar. 13, 2020, which claims the benefit under 35 U.S.C. § 119(e) of U.S. Provisional Application No. 62/819,394, filed Mar. 15, 2019, each of which is incorporated by reference herein in its entirety.

BACKGROUND

Human Immunodeficiency Virus (HIV) is a lentivirus that primarily infects hosts and cells through communication of bodily fluids or through pregnancy. HIV infects cells essential to the immune system, such as CD4+ T cells, macrophages, and dendritic cells, ultimately causing cell death. When the rate and magnitude of cell death causes essential cell levels to fall below critical levels, it become increasingly more difficult for the host to mount an effective immune response, leading to acquired immunodeficiency syndrome (AIDS). Without treatment, the average survival time after infection with HIV is estimated to be 9 to 11 years.

SUMMARY

Provided herein are mRNA-based immunogenic compositions (e.g., vaccines) and therapies that elicit neutralizing antibodies against a broad range of human immunodeficiency virus (HIV) (e.g., HIV-1) strains circulating worldwide. Use of mRNA as a vehicle for eliciting broadly neutralizing antibodies against multiple strains of HIV has the advantage of persistent in vivo expression of endogenous proteins (e.g., identical to those found in nature). Further, the co-formulation used herein, with mRNA encoding HIV Env and mRNA encoding lentivirus Gag, enables in vivo production of extracellular virus-like particles (VLPs), mimicking natural infection. Further still, the use in some embodiments of mRNA encoding full-length or partially truncated membrane-bound HIV Env gp160 or gp150 provides a bona fide “native” confirmation of expressed Env, unlike truncated soluble Env SOSIP trimers. Other embodiments provided herein provide mRNA-based immunogenic compositions that further include mRNA encoding the viral protease that is used for Gag processing, and/or mRNA encoding furin, which is used for Env processing. The intensive immunization protocols provided herein mimic continuous, high-level antigenic load in HIV-infected patients who develop broad neutralizing antibodies against HIV, and the multiple-strain heterologous boost dosing focuses the antibody response on “common” broad neutralizing antibody epitopes to the exclusion of strain-specific epitopes. In some embodiments, complete filling of Env glycan holes provides the additional advantage of an exclusion of dominant antibody responses against vaccine-irrelevant epitopes.

Induction of neutralizing antibodies with a broad spectrum of action against heterologous tier-2 isolates is a key requirement for a bona fide protective HIV-1 vaccine. Yet, none of the vaccine strategies hitherto devised has achieved this objective. In the studies presented herein, an intensive HIV-1 envelope (Env)-based immunization scheme was tested in rhesus macaques. Four groups of animals were immunized with coformulated HIV-1 Env (WITO gp150, Clade B) and SIV Gag (from SIVmac239) in order to promote the in vivo formation and release of virus-like particles. Two groups of animals received wild-type Env and two received interdomain-stabilized Env bearing the amino acid 113-432 disulfide bridge (Zhang et al., *Cell Host & Microbe* 2018; 23: 832); two groups received mRNA only, while two received mRNA followed by protein boost with the autologous SOSIP trimer. All groups were subsequently boosted with mRNA expressing Env from two heterologous HIV-1 isolates (BG505, Clade A, and DU422, Clade C); again, two groups received autologous protein boosts. High titers of neutralizing antibodies against the autologous Env (WITO.27) or against tier-1a viruses were readily induced after the second autologous immunization, becoming increasingly more persistent after each booster injection. Following the third heterologous boost, low titers of neutralizing antibodies against heterologous tier-2 viruses of different Clades were detected, including JR-FL and 12 Envs of different Clades derived from the reference small global panel. Further boosting with either mRNA or protein increased both the magnitude and durability of cross-Clade tier-2 heterologous NAb titers. Live virus challenges have been performed using repeated low-dose mucosal inoculation of a heterologous tier-2 SHIV (AD8) resulting in complete protection or delayed infection. These results provide evidence for the elicitation of cross-Clade tier-2 heterologous broadly neutralizing antibodies by mRNA immunization in a preclinical vaccine model.

In some aspects, the present disclosure provides methods of inducing in a human subject an immune response to HIV (e.g., HIV-1), the methods comprising (a) during a first period of time, administering to a subject an initial dose and multiple autologous boost doses of an HIV mRNA vaccine comprising mRNA encoding an HIV envelope (Env) protein and a mRNA encoding a lentivirus group-specific antigen (Gag) protein formulated in a lipid nanoparticle, (b) during a second period of time, administering to the subject multiple heterologous boost doses of an HIV mRNA vaccine comprising mRNA encoding an HIV Env protein and a mRNA encoding a lentivirus Gag protein formulated in a lipid nanoparticle, and (c) producing in the subject a broad and potent neutralizing antibody response against multiple strains of HIV.

In other aspects, the methods comprise, in addition to mRNA encoding Env and Gag, mRNA encoding one or both of two enzymes that are used for the full proteolytic processing of Gag and Env, respectively, and thereby promote a more efficient production and release of properly formed virus-like particles. The two enzymes are: i) the viral protease of HIV-1 or SIV, for Gag processing, and furin, a host enzyme for Env processing.

In some embodiments, the broad and potent neutralizing antibody response comprises the production of neutralizing antibodies that bind to shared epitopes on Env proteins from the multiple strains of HIV, including multiple tier-2 strains from different Clades. In some embodiments, the broadly neutralizing antibody response has an $ID_{50}$ titer of greater than 20 or greater than 50.

In some embodiments, the first period of time is 1-30 weeks following administration of the initial dose of the HIV mRNA vaccine. In some embodiments, the second period of time is 30-60 weeks following administration of the initial dose of the HIV mRNA vaccine.

In some embodiments, the time between any two doses of the HIV mRNA vaccine of (a) and/or (b) is at least 1 week. In some embodiments, the time between any two doses of the HIV mRNA vaccine of (a) and/or (b) is at least 4 weeks.

In some embodiments, the time between any two doses of the HIV mRNA vaccine of (a) and/or the HIV mRNA vaccine of (b) is 4-10 weeks.

In some embodiments, the ratio of mRNA encoding an HIV Env protein to the mRNA encoding a lentivirus Gag protein in the HIV mRNA vaccine of (a) and/or (b) is 1:1 to 10:1 (e.g., 1:1, 2:1, 3:1, 4:1, 5:1, 6:1, 7:1, 8:1, 9:1, or 10:1). In some embodiments, the ratio of mRNA encoding an HIV Env protein to the mRNA encoding a lentivirus Gag protein in the HIV mRNA vaccine of (a) and/or (b) is 3:2 to 9:2 (e.g., 3:2, 2:1, 5:2, 3:1, 7:2, 4:1, or 9:2). In some embodiments, the ratio of mRNA encoding an HIV Env protein to the mRNA encoding a lentivirus Gag protein in the HIV mRNA vaccine of (a) and/or (b) is 3:2 or at least 3:2.

In some embodiments, the ratio of mRNA encoding an HIV Env protein to the mRNA encoding furin is 10:1 to 30:1. In some embodiments, the ratio of mRNA encoding an HIV Env protein to the mRNA encoding furin is 10:1, 15:1, 20:1, 25:1, or 30:1. In some embodiments, the ratio of mRNA encoding an HIV Env protein to the mRNA encoding furin is 20:1 or at least 20:1. In some embodiments, the ratio of mRNA encoding a lentivirus Gag protein to the mRNA encoding the viral protease is 30:1 to 50:1. In some embodiments, the ratio of mRNA encoding a lentivirus Gag protein to the mRNA encoding the viral protease is 30:1, 35:1, 40:1, 45:1, or 50:1. In some embodiments, the ratio of mRNA encoding a lentivirus Gag protein to the mRNA encoding the viral protease is 40:1 or at least 40:1.

In some embodiments, an mRNA encoding a lentivirus Gag protein is replaced by an mRNA encoding the full Gag-Pol open reading frame of HIV-1 or SIV, which comprises the viral protease gene that is transcribed after a ribosomal frame-shift, thus providing an alternative to using an mRNA encoding a viral protease. In some embodiments, the Gag-Pol precursor is partially truncated to reduce its length while maintaining the full protease gene.

In some embodiments, the HIV Env protein of the mRNA HIV vaccine of (a) is selected from an HIV Env protein of Group M Clade A-K (e.g., selected from Clade A, Clade AC, Clade AE, Clade AG, Clade B, Clade C, Clade D, and Clade G), wherein the HIV Env protein of the mRNA HIV vaccine of (b) is selected from an HIV Env protein of Group M Clade A-K (e.g., selected from Clade A, Clade AC, Clade AE, Clade AG, Clade B, Clade C, Clade D, and Clade G), and wherein the Clade(s) of the HIV Env protein of (a) is different from the Clade(s) of the HIV Env protein of (b).

In some embodiments, the HIV Env protein of (a) and/or (b) comprises HIV Env SOSIP.664 mutations. In some embodiments, the HIV Env protein of (a) and/or (b) is a membrane-bound HIV Env protein. In some embodiments, the cytosolic portion of the HIV Env protein of (a) and/or (b) is truncated or partially truncated. In some embodiments, the membrane-bound HIV Env protein is gp150, with a truncation of the gp41 cytoplasmic domain at position 745, or full-length gp160. In some embodiments, the HIV Env protein of (a) and/or (b) comprises a sequence of an Env protein of an HIV strain obtained from an infected subject who has broad and potent neutralizing antibodies to HIV Env protein. In some embodiments, the HIV Env protein of (a) and/or (b) comprises a consensus sequence of variants an Env protein of an HIV strain obtained from an infected subject who has broad and potent neutralizing antibodies to HIV Env protein.

In some embodiments, the HIV Env protein of (a) and/or (b) is an uncommon Env capable of directly engaging unmutated common ancestor (UCA) antibodies from the lineages that originated some broad and potent neutralizing antibodies, such as VRC01, CH103, PG9, CH01, and others. In some embodiments, to facilitate binding to UCA antibodies, the Env protein comprises a mutation selected from 153E, 190G and N276D, relative to strain WITO4160.27 HIV Env protein, or other mutations suitable to remove the glycans at positions 188 and 276, optionally wherein the HIV Env protein of (a) and/or (b) further comprises a disulfide bridge at 113C-432GCG. In some embodiments, the HIV Env protein of (a) and/or (b) further comprises a mutation selected from N460D and N463D relative to strain BG505 HIV Env protein, or other suitable mutations to remove the glycans at positions 460 and 463. In some embodiments, the HIV Env protein of (a) and/or (b) comprises a mutation selected from K295N, D386N, and 375Y, relative to strain DU422.1 HIV Env protein, optionally wherein the HIV Env protein of (a) and/or (b) further comprises a disulfide bridge at 133C-432GCG. In some embodiments, the HIV Env protein of (a) and/or (b) comprises a mutation selected from T322N and S375Y, relative to strain WITO4160.27 HIV Env protein, optionally wherein the HIV Env protein of (a) and/or (b) further comprises a disulfide bridge at 113C-429GCG.

In some embodiments, the HIV Env protein of (a) and/or (b) is a tier-2 Env with all the major glycan holes filled in by insertion of the missing glycans.

In some embodiments, the lentivirus is selected from human immunodeficiency virus (HIV), simian immunodeficiency virus (SIV), and murine leukemia virus (muLV).

In some embodiments, the HIV mRNA vaccine further comprises a Vesicular stomatitis virus (VSV) or VSV-ΔG core protein, or the lentivirus-derived Gag is replaced by a VSV-ΔG or VSV core protein. Viral proteins include proteins that are capable of self-assembling into the VLP (Freed, E. O., *J. Virol.,* 76, 4679-87, (2002)). In some embodiments, the viral core proteins can include, but are not limited to, a viral Gag protein, for example, a retrovirus gag protein [e.g. a HIV Gag viral protein (e.g., HIV-1 NL43 Gag (GenBank serial number AAA44987)), a simian immunodeficiency virus (SW) Gag viral protein (e.g., SIVmac239 Gag (GenBank serial number CAA68379)), or a murine leukemia virus (MuLV) Gag viral protein (e.g., MuLV Gag (GenBank serial number S70394))], a retrovirus matrix protein, a rhabdovirus matrix protein M protein [e.g., a vesicular stomatis virus (VSV) M protein (e.g., VSV Matrix protein (GenBank serial number NP041714))], a filovirus viral core protein (e.g., an Ebola VP40 viral protein (e.g., Ebola virus VP40 (GenBank serial number AAN37506))), a Rift Valley Fever virus N protein (e.g., RVFV N Protein (GenBank serial number NP049344)), a coronavirus M, E and NP protein (e.g., GenBank serial number NP040838 for NP protein, NP040835 for M protein, CAC39303 for E protein of Avian Infections Bronchitis Virus and NP828854 for E protein of the SARS virus)), a bunyavirus N protein (GenBank serial number AAA47114)), an influenza M1 protein, a paramyxovirus M protein, an arenavirus Z protein (e.g., a Lassa Fever Virus Z protein), and combinations thereof.

In some aspects, the present disclosure provides methods of inducing in a human subject an immune response to HIV, the methods comprising administering to the subject a first lipid nanoparticle comprising a mRNA encoding an HIV envelope (Env) protein from a first Clade, preferentially a UCA-engaging Env, and a mRNA encoding a lentivirus group-specific antigen (Gag) protein, and administering to the subject a second lipid nanoparticle comprising a mRNA encoding an HIV Env protein from a second Clade and a mRNA encoding a lentivirus Gag protein, wherein the first lipid nanoparticle and the second lipid nanoparticle are administered more than once and in an amount effective at inducing in the subject a population of neutralizing antibodies that bind to shared epitopes on proteins from the first Clade and neutralizing antibodies that bind to shared epitopes on proteins from the second Clade. In some embodiments, the HIV is HIV Type 1 (HIV-1).

In some embodiments, the population comprises neutralizing antibodies that bind to shared epitopes on proteins from multiple strains of the first Clade and neutralizing antibodies that bind to shared epitopes on proteins from multiple strains of the second Clade.

In some embodiments, the methods further comprise administering to the subject at least one additional lipid nanoparticle comprising a mRNA encoding an HIV Env protein from at least one additional Clade and a mRNA encoding an HIV Gag protein. Thus, in some embodiments, the population comprises neutralizing antibodies that bind to shared epitopes on proteins from multiple strains of the at least one additional Clade.

In some embodiments, the first nanoparticle comprises a ratio of mRNA encoding an HIV Env protein to mRNA encoding an HIV Gag protein of at least 1:1, and/or wherein the second nanoparticle comprises a ratio of mRNA encoding an HIV Env protein to mRNA encoding an HIV Gag protein of at least 1:1. For example, the first nanoparticle may comprise a ratio of the mRNA encoding an HIV Env protein to the mRNA encoding an HIV Gag protein of at least 3:2, and/or the second nanoparticle may comprise a ratio the mRNA encoding an HIV Env protein to the mRNA encoding an HIV Gag protein of at least 3:2.

In some embodiments, the first nanoparticle comprises a ratio of mRNA encoding an HIV Env protein to mRNA encoding furin of at least 5:1. In some embodiments, the ratio of mRNA encoding an HIV Gag protein to mRNA encoding a viral protease is at least 5:1. In some embodiments, the first nanoparticle comprises mRNA encoding the full or partially truncated Gag-Pol gene from HIV-1 or SIV, which comprises the viral protease gene, thus providing an alternative to an mRNA encoding a viral protease.

In some embodiments, the HIV Env protein comprises mutations, relative to wild-type HIV Env protein, that favor a closed conformation. In some embodiments, the HIV Env protein comprises mutations, relative to wild-type HIV Env protein, that comprises glycan knock-in or knock-out modifications. In some embodiments, the HIV Env protein is a stabilized soluble Env protein. For example, HIV Env protein may be an HIV Env SOSIP.664 protein (e.g., SEQ ID NO: 9). In some embodiments, the HIV Env protein is a membrane-bound HIV Env protein. In some embodiments, the cytosolic portion of the HIV Env protein is partially truncated. For example, the membrane-bound HIV Env protein may be gp150 with a truncation at position 745, or gp160.

In some embodiments, the lentivirus is selected from HIV, simian immunodeficiency virus (SIV), and murine leukemia virus (muLV). In some embodiments, the lentivirus-derived Gag is replaced by VSV-ΔG or VSV core protein.

In some embodiments, the first Clade, the second Clade, and the at least one additional Clade are selected from the group consisting of HIV Group M Clades A-K and related circulating recombinant forms (CRFs).

In some embodiments, the first lipid nanoparticle and the second nanoparticle are administered sequentially. In other embodiments, the first lipid nanoparticle and the second nanoparticle are administered simultaneously.

In some embodiments, the first lipid nanoparticle is administered as multiple doses separated by at least 1 week per administration, prior to administration of the second lipid nanoparticle. In some embodiments, the second lipid nanoparticle is administered as multiple doses separated by at least 1 week per administration, after administration of the first lipid nanoparticle. In some embodiments, the second lipid nanoparticle and the at least one additional lipid nanoparticle are administered simultaneously.

In some embodiments, a first Clade is Clade A (e.g., Clade A, Clade AC, Clade AE, or Clade AG). For example, an HIV Env protein may be an HIV Clade A BG505, Q23, Q842, MI369, KER2008, 0330, RW020 or BI369 strain Env protein, an HIV Clade AC 3301 strain Env protein, an HIV Clade AE C2101, CM244 or BJOXO28000 strain Env protein, or an HIV Clade AG DJ263 or T280 strain Env protein.

In some embodiments, a first Clade is Clade B. For example, an HIV Env protein may be an HIV Clade B WITO strain Env protein with or without removal of glycans at positions 188, 276, 460 and 463 to better engage UCA antibodies. In some embodiments, the HIV Env protein is selected from HIV Clade B WITO, X2278, JRCSF, JR-FL, B41, 3988, 45_01dG5, BX08, RHPA, TRJO, YU2 or REJO strain Env Proteins.

In some embodiments, a first Clade is Clade C. For example, an HIV Env protein may be an HIV Clade C 426c strain Env protein with or without removal of glycans at positions 188, 276, 460 and 463 to better engage UCA antibodies. In some embodiments, the HIV Env protein is selected from HIV Clade C DU422, 426C, CH505, ZM176, ZM249, ZA012, DU156, CH848, CH1012, MM24, MM45, 001428, BR025, or MW965 strain Env proteins.

In some embodiments, a first Clade is Clade D. For example, an HIV Env protein may be an HIV Clade D A07412M1 strain Env protein.

In some embodiments, a first Clade is Clade G. For example, an HIV Env protein may be an HIV Clade G X1193 or P1981 strain Env protein.

In some embodiments, a second Clade is Clade A (e.g., Clade A, Clade AC, Clade AE, or Clade AG). For example, an HIV Env protein may be an HIV Clade A BG505, Q23, Q842, MI369, KER2008, 0330, RW020 or BI369 strain Env protein, an HIV Clade AC 3301 strain Env protein, an HIV Clade AE C2101, CM244 or BJOXO28000 strain Env protein, or an HIV Clade AG DJ263 or T280 strain Env protein.

In some embodiments, a second Clade is Clade B. For example, an HIV Env protein may be an HIV Clade B WITO strain Env protein with or without removal of glycans at positions 188, 276, 460 and 463 to better engage UCA antibodies. In some embodiments, the HIV Env protein is selected from HIV Clade B WITO, X2278, JRCSF, JR-FL, B41, 3988, 45_01dG5, BX08, RHPA, TRJO, YU2 or REJO strain Env Proteins.

In some embodiments, a second Clade is Clade C. For example, an HIV Env protein may be an HIV Clade C 426c strain Env protein with or without removal of glycans at positions 188, 276, 460 and 463 to better engage UCA antibodies. In some embodiments, the HIV Env protein is selected from HIV Clade C DU422, 426C, CH505, ZM176, ZM249, ZA012, DU156, CH848, CH1012, MM24, MM45, 001428, BR025, or MW965 strain Env proteins.

In some embodiments, a second Clade is Clade D. For example, an HIV Env protein may be an HIV Clade D A07412M1 strain Env protein.

In some embodiments, a second Clade is Clade G. For example, an HIV Env protein may be an HIV Clade G X1193 or P1981 strain Env protein.

In some embodiments, the HIV Env protein comprises a sequence of an Env protein of an HIV strain obtained from an infected subject who has broad and potent neutralizing antibodies to HIV Env protein. In some embodiments, the HIV Env protein comprises a consensus sequence of variants an Env protein of an HIV strain obtained from an infected subject who has broad and potent neutralizing antibodies to HIV Env protein.

In some embodiments, the methods comprise administering to the subject a first lipid nanoparticle comprising a mRNA encoding a first HIV Env protein and a mRNA encoding an HIV Gag polyprotein, administering to the subject a second lipid nanoparticle comprising a mRNA encoding a second HIV Env protein and a mRNA encoding an HIV Gag polyprotein, and administering to the subject a third lipid nanoparticle comprising a mRNA encoding a third HIV Env protein and a mRNA encoding an HIV Gag polyprotein, wherein the population of neutralizing antibodies comprises neutralizing antibodies that bind to shared epitopes on proteins from multiple different HIV strains. In some embodiments, at least one of the first, second, and third HIV Env proteins comprises a sequence of an Env protein of an HIV strain obtained from an infected subject who has broad and potent neutralizing antibodies to HIV Env protein. In some embodiments, at least one of the first, second, and third HIV Env proteins comprises a consensus sequence of variants an Env protein of an HIV strain obtained from an infected subject who has broad and potent neutralizing antibodies to HIV Env protein.

In some embodiments, the methods comprise administering to the subject a first lipid nanoparticle comprising a mRNA encoding an HIV Clade B Env protein and a mRNA encoding an HIV Gag polyprotein, administering to the subject a second lipid nanoparticle comprising a mRNA encoding an HIV Clade A Env protein and a mRNA encoding an HIV Gag polyprotein, and administering to the subject a third lipid nanoparticle comprising a mRNA encoding an HIV Clade C Env protein and a mRNA encoding an HIV Gag polyprotein, wherein the population of neutralizing antibodies comprises neutralizing antibodies that bind to shared epitopes on HIV Clade B proteins, HIV Clade A proteins, and HIV Clade C proteins. In some embodiments, the population of neutralizing antibodies comprises neutralizing antibodies that bind to shared epitopes on at least 3 Clades comprised in the group-M (Clades A-K) HIV viruses.

In some embodiments, the population comprises neutralizing antibodies that bind to shared epitopes on proteins from multiple Clade B HIV strains, neutralizing antibodies that bind to shared epitopes on proteins from multiple Clade A HIV strains, and neutralizing antibodies that bind to shared epitopes on proteins from multiple Clade C HIV strains. In some embodiments, the population comprises neutralizing antibodies that bind to shared epitopes on proteins from at least five (5) different HIV strains. For example, the population may comprise neutralizing antibodies that bind to shared epitopes on proteins from at least 10 different HIV strains. In some embodiments, the population comprises neutralizing antibodies that bind to shared epitopes on proteins from any two or more (e.g., 2, 3, 4, 5, 6, 7, 8, 9, 10, 11, 12, 13, 14, 15, 16, 17, 18, 19, or 20) of the following HIV strains: JRFL, WITO.33, BG505, AD8, 398F1, CNE8, CNE55, 25710, CE1176, X1632, TRO11, X2278, BJOXO2000, X2632, 246F3, CH119, CE0217, A3, 02, and A3/02.

In some embodiments, none of the first, second, or at least one additional lipid nanoparticles comprise mRNA encoding a soluble HIV Env protein.

Also provided herein are immunogenic compositions comprising a lipid nanoparticle comprising mRNA encoding a membrane-bound HIV Env protein and a mRNA encoding an HIV Gag protein, wherein the lipid nanoparticle comprises an ionizable cationic lipid, a non-cationic lipid, sterol, and a PEG-modified lipid. In some embodiments, the immunogenic compositions comprise a lipid nanoparticle comprising mRNA encoding an HIV Env SOSIP.664 protein and a mRNA encoding an HIV Gag protein. In some embodiments, the immunogenic compositions comprise a lipid nanoparticle comprising mRNA encoding a membrane-bound HIV Env protein and a mRNA encoding an HIV Gag protein, wherein the ratio of the mRNA encoding a membrane-bound HIV Env protein to the mRNA encoding an HIV Gag protein is at least 3:2.

DETAILED DESCRIPTION

Figure 1A:
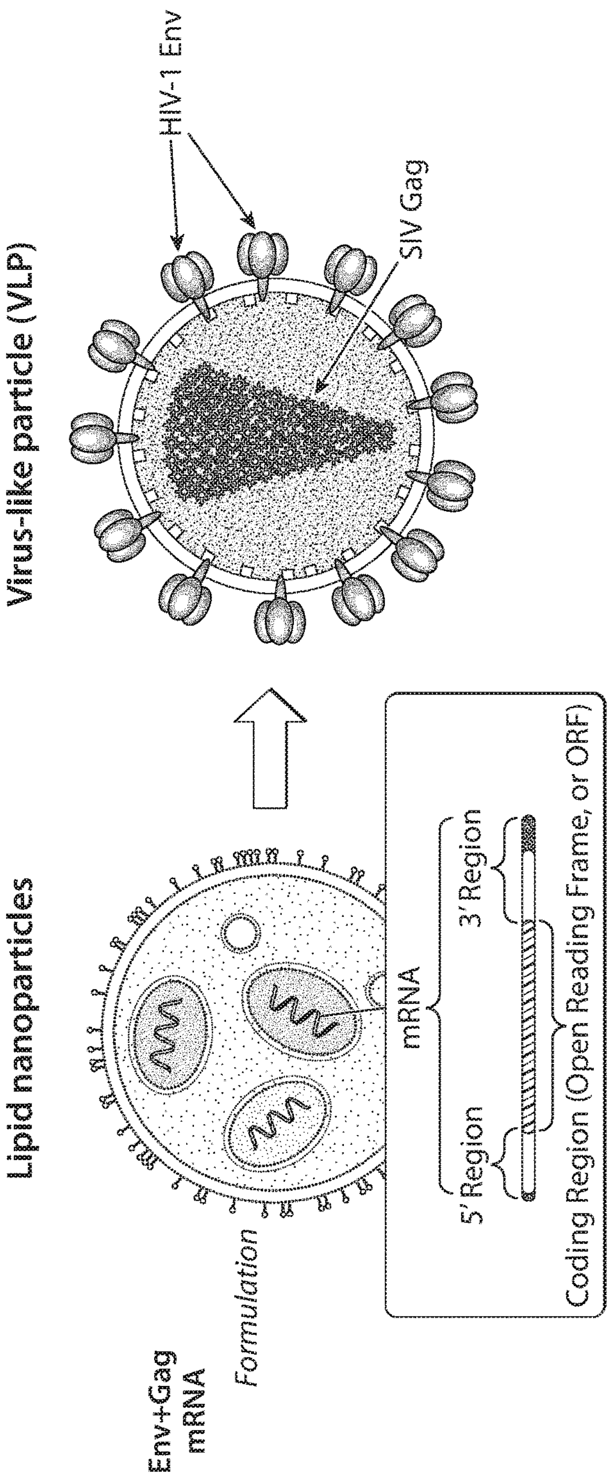
FIG. 1A shows a schematic of the co-formulation used herein, with mRNA encoding HIV Env and mRNA encoding lentivirus Gag, which enables in vivo production of extracellular virus-like particles (VLPs), mimicking natural infection.
Figure 1B:
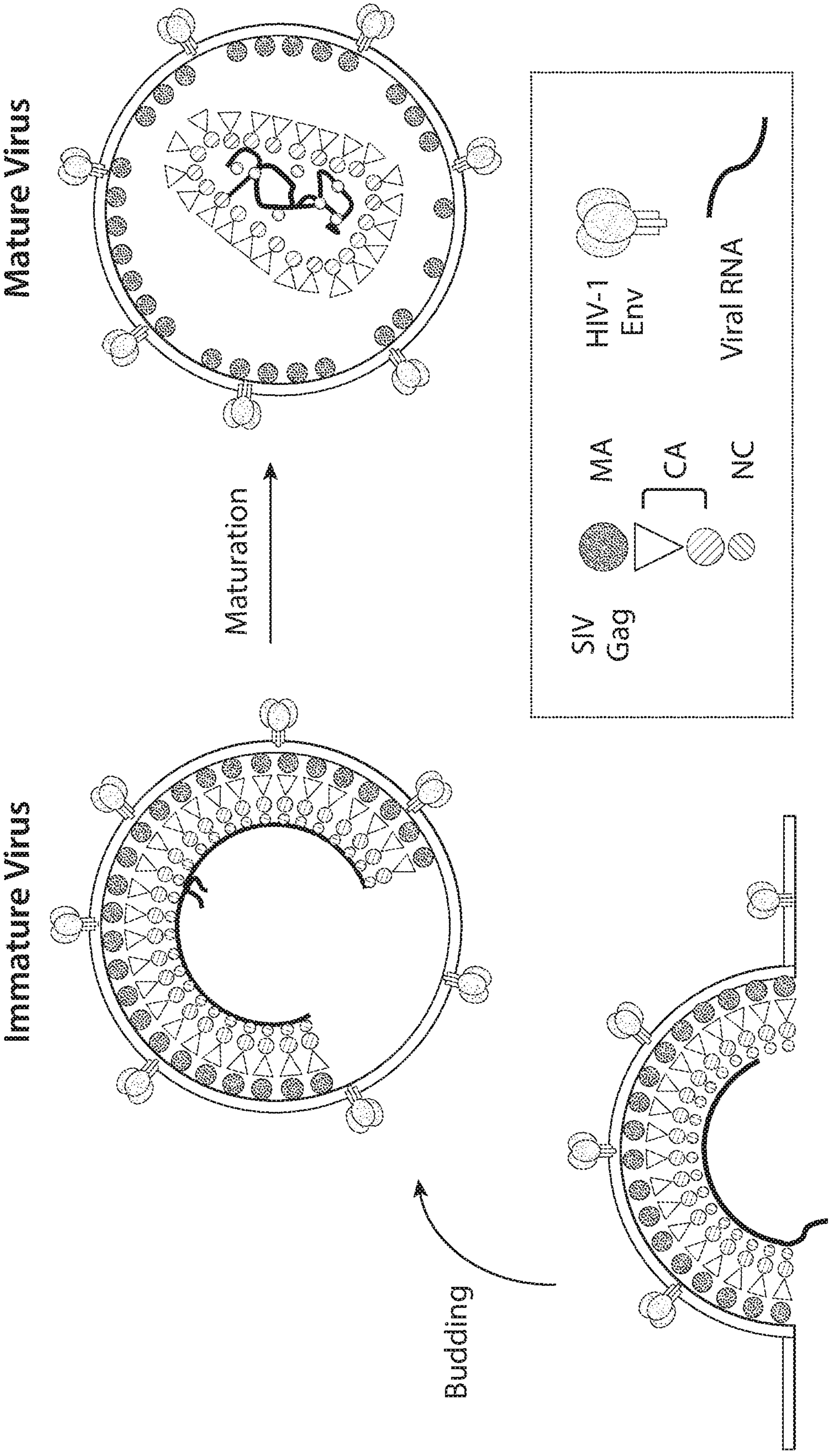
FIG. 1B shows a schematic of the HIV-1 maturation process.

In some aspects, the present disclosure provides methods of inducing in a human subject an immune response to HIV, the methods comprising administering to the subject a first lipid nanoparticle comprising a mRNA encoding an HIV envelope (Env) protein from a first Clade and a mRNA encoding a lentivirus group-specific antigen (Gag) protein, and administering to the subject a second lipid nanoparticle comprising a mRNA encoding an HIV Env protein from a second Clade and a mRNA encoding a lentivirus Gag protein.

Human Immunodeficiency Virus (HIV)

Some aspects of the disclosure provide methods of inducing in a subject an immune response to human immunodeficiency virus (HIV). HIV (Retroviridae, Orthoretrovirinae) is a lentivirus capable of long-term latent infection of cells and short-term cytopathic effects, which can produce the progressive and fatal acquired immunodeficiency syndrome (AIDS). HIV causes depletion of host T-cells, primarily CD4+ T-cells, thereby leaving the host unable to fight off serious as well as otherwise innocuous infections. An infectious HIV virion includes two identical strands of RNA that are packaged within a core of viral proteins. The virion core is surrounded by a phospholipid bilayer envelope largely derived from the host cell membrane and includes proteins encoded in the viral RNA.

Two major and closely related strains of HIV have been identified, HIV type 1 (HIV-1) and HIV type 2 (HIV-2), of which HIV-1 is the predominate strain and recognized as the more virulent and aggressive form of HIV accounting for approximately 95% of all HIV infections world-wide, with HIV-2 being relatively uncommon and less infectious. In some embodiments, the methods of the disclosure induce an immune response to HIV-1. The present disclosure contemplates HIV vaccines that can equally target and/or be effective in treating or preventing any strain of HIV.

The integrated form of HIV-1, also known as the provirus, is approximately 9.8 kilobases in length. Both ends of the provirus are flanked by a repeated sequence Referred to as the long terminal repeats (LTRs). The genes of HIV are located in the central region of the proviral DNA and encode at least nine proteins, divided into three classes: the major structural proteins, Gag, Pol, and Env; the regulatory proteins, Tat and Rev; and the accessory proteins, Vpu, Vpr, Vif, and Nef. The mRNA vaccines of the present disclosure, in some embodiments, comprise mRNA encoding HIV Env protein and/or lentivirus (e.g., HIV) Gag protein.

HIV Env

The Env protein forms part of the HIV viral envelope. The env gene encodes glycoprotein 160 (gp160), which is cleaved by the host cell protease yielding glycoprotein 120 (gp120) and glycoprotein 41 (gp41) subunits, with the external gp120 subunit non-covalently bonded to the transmembrane gp41 subunit. This resulting Env complex, which includes three gp120/gp41 pairs, mediates a multistep process that results in the fusion of the viral membrane with the host cell membrane. In the first step of the process, gp120 facilitates initial binding with host cells, most commonly through CD4 receptors, which in turn fosters binding of a chemokine co-receptor. The most common chemokine receptors to act as co-receptors are CXCR4 and CCR5, however additional chemokine receptors, as well as various other proteins of the G protein-coupled receptor superfamily, have been shown to serve as co-receptors for HIV entry. Co-receptor binding causes gp41 to undergo a conformational change exposing a hydrophobic region to the host cell membrane. Gp41 then inserts itself into the host cell causing gp41 to again change conformation and fold back on itself forcing fusion of the host cell membrane with the viral membrane, in turn enabling the viral capsid to enter the cell. Env can genetically vary by as much as 35% across Clades causing variation in the precise genetic sequence of the protein, which causes distinct tropisms. These tropisms are often related to the specificity of the gp120 variants to different chemokine receptors, thus influencing virion binding, altering membrane fusion triggers, and ultimately the mechanism of host cell infection. Env protein is also assembled post viral DNA integration into the host genome. Once transcribed, the viral RNA is transported to the cytoplasm, where Env protein is generated. Post translation, the protein is integrated into the host cell membrane, a process facilitated by Gag polyprotein.

The HIV Env proteins of the present disclosure may be one of several different HIV Clades. HIV-1, for example, is divided into four known groups (M, N, O, and P), which are believed to represent an independent transmission of simian immunodeficiency virus (SIV) into humans. Of the four groups, M is considered the major group (accounting for more than 90% of HIV and AIDS cases by some estimates), with N, O, and P representing the minor groups. Within the M group of HIV-1, eleven sub-types, referred to as Clades A-K, have been established, which unlike the groups do not indicate distinct transmissions of SIV, but rather often refer to the geographic area the Clade is predominate. Similar to the four groups, Clades have been assigned letter designations A-K, but more may be established. Further variations of the known Clades can result from genetic combinations of the Clades, resulting in hybrids known as circulating recombinant forms (CRF) (e.g., A/B, C/K, or any combination of A-K).

The HIV Env proteins encoded by the mRNA administered herein may be, and in preferred embodiments are, from different Clades, for example, one from a “first Clade” (e.g., A-K) and one from a second Clade (e.g., any one of A-K that is not the first Clade) (and optionally at least one additional Clade, e.g., any one of A-K that is not the first or second Clade. In some embodiments, the first Clade, the second Clade, and the at least one additional Clade are selected from the group consisting of HIV Group M Clades A-K and related circulating recombinant forms (CRFs). The first, the second Clade, and the at least one additional Clade may be selected, in some embodiments, from Clade A of Group M, Clade AC of Group M, Clade AE of Group M, Clade AG of Group M, Clade B of Group M, Clade C of Group M, Clade D of Group M, Clade E of Group M, Clade F of Group M, Clade G of Group M, Clade H of Group M, Clade I of Group M, Clade J of Group M, or Clade K of Group M. In some embodiments, the first Clade is Clade A of Group M. In some embodiments, the first Clade is Clade AC of Group M.

In some embodiments, the first Clade is Clade AE of Group M. In some embodiments, the first Clade is Clade AG of Group M. In some embodiments, the first Clade is Clade B of Group M. In some embodiments, the first Clade is Clade C of Group M. In some embodiments, the first Clade is Clade B of Group M, and the second Clade is Clade A of Group M. In some embodiments, the first Clade is Clade B of Group M, and the second Clade is Clade C of Group M.

In some embodiments, the first Clade is Clade B. For example, the HIV Env protein may be an HIV Clade B WITO, X2278, JRCSF, JR-FL, B41, 3988, 45_01dG5, BX08, RHPA, TRJO, YU2, or REJO strain Env protein. In some embodiments, the second Clade is Clade A, for example, an HIV Clade A BG505, Q23, Q842, MI369, KER2008, 0330, RW020, or BI369 strain Env protein. In some embodiments, the second Clade is Clade C, for example, an HIV Clade C DU422, 426C, CH505, ZM176, ZM249, ZA012, DU156, CH848, CH1012, MM24, MM45, 001428, BR025, or MW965 strain Env protein.

The Env proteins encoded by the HIV mRNA vaccines of the present disclosure induce protective titers of broadly neutralizing antibodies against multiple strains of HIV (e.g., multiple strains of HIV-1). These neutralizing antibodies bind to the Env complex on the virion surface to neutralize HIV infectivity. Unlike more common strategies for broad neutralizing antibody induction that involve the design of soluble, recombinant protein mimics of the native Env complex, the HIV mRNA vaccines provided herein, in some embodiments, encode membrane-bound Env protein, such as gp160, or a truncated form, gp150 (cytosolic portion truncated at residue 775, relative to the reference HIV Env protein). Herein, the "reference HIV Env protein" is a soluble, stabilized trimeric HIV Env SOSOP.644 complex; Sanders R W et al. *PLoS Pathog* 9:e1003618, incorporated herein by reference). This soluble reference HIV Env protein includes an engineered disulfide bond that covalently links subunits gp120 and $gp41_{ECTO}$ (produced by introducing a stop codon to truncate the gp41 ectodomain) and also includes an Ile-to-Pro change at residue 559 (I559P) that helps maintain the $gp41_{ECTO}$ moieties in the prefusion form (Binley J M et al. *J Virol* 2000; 74: 627-643; and Sanders R W et al. *J Virol* 2002; 76: 8875-8889, each of which is incorporated herein by reference) as well as a Ala-to-Cys change at residue 501 (A501C) and a Thr-to-Cys at residue 605 (T605C). In addition, the truncation of $gp41_{ECTO}$ at residue 664 eliminates a hydrophobic region that tends to cause trimer aggregation (Khayat R et al. *J Virol* 2013; 87:9873-9885; Wu X et al. *J Virol* 2006; 80: 835-844, each of which is incorporated herein by reference).

Stabilized Trimeric HIV Env SOSOP.644 Complex (SEQ ID NO: 9)

MDAMKRGLCCVLLLCGAVFVSPSQEIHARFRRGARAENLWVTVYYGVPVW
KDAETTLFCASDAKAYETEKHNVWATHACVPTDPNPQEIHLENVTEEFNM
WKNNMVEQMHTDIISLWDQSLKPCVKLTPLCVTLQCTNVTNNITDDMRGE
LKNCSFNMTTELRDKKQKVYSLFYRLDVVQINENQGNRSNNSNKEYRLIN
CNTSAITQACPKVSFEPIPIHYCAPAGFAILKCKDKKFNGTGPCPSVSTV
QCTHGIKPVVSTQLRQAHCNVSKATWNETLGKVVKQLRKHFGNNTIIRFA
NSSGGDLEVTTHSFNCGGEFFYCNTSGLFNSTWISNTSVQGSNSTGSNDS
ITLPCRIKQIINMWQRIGQAMYAPPIQGVIRCVSNITGLILTRDGGSTNS

-continued

TTETFRPGGGDMRDNWRSELYKYKVVKIEOLGVAPTRCKRRVVGRRRRRR
AVGIGAVFLGFLGAAGSTMGAASMTLTVQARNLLSGIVQQQSNLLRAPEA
QQHLLKLTVWGIKQLQARVLAVERYLRDQQLLGIWGCSGKLICCTNVPWN
SSWSNRNLSEIWDNMTWLQWDKEISNYTQIIYGLLEESQNQQEKNEQDLL
ALD*****

Several variant forms of HIV Env protein may be encoded by the mRNA of the vaccines provided herein.

The HIV Env proteins, for example, may include one or more CD4 primate binding modifications. These modifications include any of the mutations selected from 153E and 375Y, relative to a reference HIV Env protein comprising the sequence of SEQ ID NO:1. In some embodiments, a mRNA encodes an HIV Env protein comprising a 153E mutation, relative to a reference HIV Env protein comprising the sequence of SEQ ID NO:1. In some embodiments, a mRNA encodes an HIV Env protein comprising a 375Y mutation, relative to a reference HIV Env protein comprising the sequence of SEQ ID NO:1. Thus, in some embodiments, the membrane-bound form of HIV Env protein comprises mutations, relative to the reference HIV Env protein, that favor a closed conformation, and thus, cannot bind CD4.1

(SEQ ID NO: 1)

```
  1 mrvkekyqhl wrwgwrwgtm llgmlmicsa teklwvtvyy
    gvpvwkeatt tlfcasdaka
 61 ydtevhnvwa thacvptdpn pqevvlvnvt enfnmwkndm
    veqmhediis lwdqslkpcv
121 kltplcvslk ctdlkndtnt nsssgrmime kgeikncsfn
    istsirgkvq keyaffykld
181 iipidndtts ykltscntsv itqacpkvsf epipihycap
    agfailkcnn ktfngtgpct
241 nvstvqcthg irpvvstqll lngslaeeev virsvnftdn
    aktiivqlnt sveinctrpn
301 nntrkririq rgpgrafvti gkignmrqah cnisrakwnn
    tlkqiasklr eqfgnnktii
361 fkqssggdpe ivthsfncgg effycnstql fnstwfnstw
    stegsnnteg sdtitlperi
421 kqiinmwqkv gkamyappis gqircssnit gllltrdggn
    snneseifrp gggdmrdnwr
481 selykykvvk ieplgvaptk akrrvvqrek ravgigalfl
    gflgaagstm gaasmtltvq
541 arqllsgivq qqnnllraie aqqhllqltv wgikqlqari
    laverylkdq qllgiwgcsg
601 klicttavpw naswsnksle qiwnhttwme wdreinnyts
    lihslieesq nqqekneqel
661 leldkwaslw nwfnitnwlw yiklfimivg glvglrivfa
    vlsivnrvrq gysplsfqth
```

-continued

```
721 lptprgpdrp egieeegger drdrsirlvn gslaliwddl
    rslclfsyhr lrdlllivtr
781 ivellgrrgw ealkywwnll qywsqelkns aysllnatai
    avaegtdrvi evvqgacrai
841 rhiprrirqg lerill
```

HIV Env proteins having glycan post-translational modifications are also contemplated herein. These modifications may be made at a residue selected from, for example, residue 276 (276N), 295 (295N), 322 (322N), and 386 (386), relative to a reference HIV Env protein comprising the sequence of SEQ ID NO:1. In some embodiments, a mRNA encodes an HIV Env protein comprising a glycan modification at residue 276 (276N), relative to a reference HIV Env protein comprising the sequence of SEQ ID NO:1. In some embodiments, a mRNA encodes an HIV Env protein comprising a glycan modification at residue 295 (295N), relative to a reference HIV Env protein comprising the sequence of SEQ ID NO:1. In some embodiments, a mRNA encodes an HIV Env protein comprising a glycan modification at residue 322 (322N), relative to a reference HIV Env protein comprising the sequence of SEQ ID NO:1. In some embodiments, a mRNA encodes an HIV Env protein comprising a glycan modification at residue 386 (386N), relative to a reference HIV Env protein comprising the sequence of SEQ ID NO:1.

In some embodiments, the HIV Env protein comprises mutations, relative to wild-type HIV Env protein, that comprises glycan knock-in or knock-out modifications. In some embodiments, the HIV Env protein comprises glycan knock-in mutations at residues selected from N332, N241, and N289, relative to an HIV BG550 strain Env protein. In some embodiments, the HIV Env protein comprises glycan knock-in mutations at residues selected from N295 and N386, relative to an HIV DU422, DU172.17, ZM176.66, CNE58, or 426c strain Env protein. In some embodiments, the HIV Env protein comprises glycan knock-in mutations at residue N188, relative to an HIV WITO strain Env protein. In some embodiments, the HIV Env protein comprises glycan knock-out mutations at residue N276, relative to an HIV BG550 strain Env protein.

In some embodiments, the HIV isolate/strain is WITO4160.27. In some embodiments, an HIV mRNA encode membrane-bound Env gp150 (truncated at residue 775) that includes a 153E mutation and a 276D, relative to a reference HIV Env protein, wherein the reference HIV Env protein comprises the sequence of SEQ ID NO: 2. In some embodiments, an HIV mRNA encode membrane-bound Env gp150 (truncated at residue 775) that includes a 153E mutation, a 276D mutation, and a 113C-432GCG disulfide bridge, relative to a reference HIV Env protein, wherein the reference HIV Env protein comprises the sequence of SEQ ID NO: 2.

```
(SEQ ID NO: 2; GenBank: ABG67917.1;
WITO4160.27)
  1 mkvmgtkkny qhlwrwgiml lgmlmmssaa eqlwvtvyyg
    vpvwreantt lfcasdakay
 61 dtevhnvwat hacvptdpnp qevvmgnvte dfnmwknnmv
    eqmhediisl wdqslkpcvk
```

-continued

```
121 ltplcvtlhc tnvtisstng stanvtmreg mkncsfnttt
    virdkiqkey alfykldivp
181 iegkntntsy rlincntsvi tqacpkvsfe pipihycapa
    gfailkcnnk tfngkgpern
241 vstvqcthgi kpvvstqlll ngslaeedii irsenftnng
    kniivqlkep vkinctrpgn
301 ntrrsinigp grafyatgai igdirkahcn isteqwnntl
    tqivdklreq fgnktiifnq
361 ssggdpevvm htfncggeff ycnstqlfns twfnngtstw
    nstadnitlp crikqvinmw
421 qevgkamyap pirgqidcss nitgliltrd ggsnssqnet
    frpgggnmkd nwrselykyk
481 vvkieplgia ptrakrrvvq rekravtlga vflgflgaag
    stmgaasltl tvgarlllsg
541 ivqqqsnllr aieaqqhmlq ltvwgikqlq arvlaieryl
    kdqqllgiwg csgklicttt
601 vpwntswsnk sydyiwnnmt wmqwereidn ytgfiytlie
    esqnqqekne lelleldkwa
661 slwnwfnitn wlwyiklfim iigglvglrt vcavlsivnr
    vrqgysplsf qtrlpnprgp
721 grpeetegeg gerdrdrsar lvngflaiiw ddlrslclfs
    yhrlrdllli varvveilgr
781 rgweilkyww nllkywsqel knsaysllnv taiavaegtd
    rvieivqrav railhiptri
841 rqgferall
```

In some embodiments, the HIV isolate/strain is DU422, DU172.17, ZM176.66, CNE58, or 426c. In some embodiments, an HIV mRNA encode membrane-bound Env gp150 (truncated at residue 775) that includes a 295N mutation, a 386N mutation, and a 375Y mutation, relative to a reference HIV Env protein, wherein the reference HIV Env protein comprises the sequence of SEQ ID NO: 3. In some embodiments, an HIV mRNA encode membrane-bound Env gp150 (truncated at residue 775) that includes a 295N mutation, a 386N mutation, a 375Y mutation, and a 133C-432GCG disulfide bridge, relative to a reference HIV Env protein, wherein the reference HIV Env protein comprises the sequence of SEQ ID NO: 3.

```
(SEQ ID NO: 3; GenBank: ABD83641.1; Du422.1)
  1 mrvrgiprnw pqwwiwgilg fwmiiicrvv gnldlwvtvy
    ygvpvwkeak ttlfcasdak
 61 aydkevhnvw athacvptdp npqeivlenv tenfnmwknd
    mvdqmhedii slwdqslkpc
```

-continued

```
121  vkltplcvtl ncknvnisan anatatlnss mngeikncsf
     ntttelrdkk qkvyalfykp
181  dvvpinggeh netgeyilin cnsstitqac pkvsfdpipi
     hycapagyai lkcnnktfng
241  tgpcnnvstv qcthgikpvv stqlllngsl aeeeiivrse
     nitnniktii vhlnksveik
301  ctrpnnntrk svrigpgqtf yatgeiigdi reahcnisre
     twnstliqvk eklrehynkt
361  ikfepssggd levtthsfnc rgeffycdtt klfnetklfn
     eseyvdnkti ilperikqii
421  nmwqevgram yappiegnit cksnitglll twdggenste
     gvfrpgggnm kdnwrselyk
481  ykvveikplg vaptkskrkv vgrekravgl gavllgflga
     agstmgaasi tltvgarqll
541  sgivqqqsnl lraieaqqhl lqltvwgikq lqtrvlaier
     ylkdqqllgl wgcsgklica
601  tavpwnssws nkslgdiwdn mtwmqwdrei snytntifrl
     ledsqnqqek nekdllalds
661  wknlwnwfdi tnwlwyikif imivggligl riifgvlaiv
     krvrqgyspl sfqtlipnpr
721  gpdrlgriee eggeqdkdrs irlvsgflal awddlrslcl
     fsyhqlrdfi ltaaraaell
781  grsslrglqr gwevlkylgn lvqywglelk rsainlfdti
     aiavaegtdr iieviqricr
841  airyiptrir qgfeaall
```

In some embodiments, the HIV isolate/strain is BG505. In some embodiments, an HIV mRNA encode membrane-bound Env gp160 that includes a 322N mutation and a 375Y mutation, relative to a reference HIV Env protein, wherein the reference HIV Env protein comprises the sequence of SEQ ID NO: 4. In some embodiments, the HIV isolate/strain is BG505. In some embodiments, an HIV mRNA encode membrane-bound Env gp160 that includes a 322N mutation, a 375Y mutation, and a 113C-429GCG disulfide bridge, relative to a reference HIV Env protein, wherein the reference HIV Env protein comprises the sequence of SEQ ID NO: 4.

```
(SEQ ID NO: 4; GenBank: ABA61516.1; BG505)
  1  mrvmgiqrnc qhlfrwgtmi lgmiiicsaa enlwvtvyyg
     vpvwkdaett lfcasdakay
 61  etekhnvwat hacvptdpnp qeihlenvte efnmwknnmv
     eqmhtdiisl wdqslkpcvk
121  ltplcvtlqc tnytnnitdd mrgelkncsf nmttelrdkk
     qkvyslfyrl dvvqinenqg
```

-continued

```
181  nrsnnsnkey rlincntsai tqacpkvsfe pipihycapa
     gfailkckdk kfngtgpcps
241  vstvqcthgi kpvvstqlll ngslaeeevm irsenitnna
     knilvqfntp vqinctrpnn
301  ntrksirigp gqafyatgdi igdirqahct vskatwnetl
     gkyvkqlrkh fgnntiirfa
361  nssggdlevt thsfncggef fycntsglfn stwisntsyq
     gsnstgsnds itlperikqi
421  inmwqrigqa myappiqgvi rcvsnitgli ltrdggstns
     ttetfrpggg dmrdnwrsel
481  ykykyvkiep lgvaptrakr rvvgrekrav gigavflgfl
     gaagstmgaa smtltvgarn
541  llsgivqqqs nllraieaqq hllkltvwgi kqlqarvlav
     erylrdqqll giwgcsgkli
601  cttnvpwnss wsnrnlseiw dnmtwlqwdk eisnytqiiy
     glleesqnqq ekneqdllal
661  dkwaslwnwf disnwlwyik ifimivggli glrivfavls
     vihrvrqgys plsfqthtpn
721  prgldrperi eeedgeqdrg rstrlvsgfl alawddlrsl
     clfcyhrlrd filiaarive
781  llghsslkgl rlgweglkyl wnllaywgre lkisainlfd
     tiaiavaewt drvieigqrl
841  craflhiprr irqglerall
```

The HIV Env protein, in some embodiments, comprises a sequence of an Env protein of an HIV strain obtained from an infected subject who has broad and potent neutralizing antibodies to HIV Env protein. A subject is considered to have been infected with HIV if, for example, the subject test positive following an HIV viral load test (also referred to as an HIV nucleic acid amplification test (NAAT or NAT); HIV by PCR; or HIV RNA test). Methods for diagnosing an HIV positive subject are known, any of which may be used herein.

In some embodiments, the HIV Env protein comprises a consensus sequence of variants an Env protein of an HIV strain obtained from an infected subject who has broad and potent neutralizing antibodies to HIV Env protein. The consensus sequence may be determined, for example, by aligning the amino acid sequences (or nucleic acid sequences) of various HIV Env proteins obtained from an infected subject who has broad and potent neutralizing antibodies to HIV Env protein, then determining the most commonly expressed amino acid (or nucleic acid) at each position.

HIV Gag

The lentivirus group-specific antigen (gag) gene encodes a 55-kilodalton (kD) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6 (Göttlinger H G et al. *Proc Natl Acad Sci USA* 1989; 86(15): 5781-5).

The lentiviral Gag protein encoded herein may be an HIV Gag protein, a simian immunodeficiency virus (SIV) Gag protein, or a murine leukemia virus (muLV) Gag protein. In some embodiments, the Gag protein is an HIV Gag protein. In some embodiments, the Gag protein is a SIV Gag protein. In some embodiments, the Gag protein is an muLV Gag protein. In some embodiments, the SIV Gag protein is a SIVmac239 Gag protein.

```
>HIV_gag(HXB2 genbank AAB50258.1)
                                                         (SEQ ID NO: 5)
  1   mgarasvlsg geldrwekir lrpggkkkyk lkhivwasre lerfavnpgl letsegcrqi

 61   lgqlqpslqt gseelrslyn tvatlycvhq rieikdtkea ldkieeeqnk skkkaqqaaa

121   dtghsnqvsq nypivqniqg qmvhqaispr tlnawvkvve ekafspevip mfsalsegat

181   pqdlntmlnt vgghqaamqm lketineeaa ewdrvhpvha gpiapgqmre prgsdiagtt

241   stlqeqigwm tnnppipvge iykrwiilgl nkivrmyspt sildirqgpk epfrdyvdrf

301   yktlraeqas qevknwmtet llvqnanpdc ktilkalgpa atleemmtac qgvggpghka

361   rvlaeamsqv tnsatimmqr gnfrnqrkiv kcfncgkegh tarncraprk kgcwkcgkeg

421   hqmkdcterq anflgkiwps ykgrpgnflq srpeptappe esfrsgvett tppqkqepid

481   kelypltslr slfgndpssq
```

```
HIV Gag-Pot
>HIV_gag_pol(psPAX2)
                                                         (SEQ ID NO: 6)
ATGGGTGCGAGAGCGTCAGTATTAAGCGGGGGAGAATTAGATCGATGGGAAAAAATTCGGTTAAGGCCAGGGGGA

AAGAAAAAATATAAATTAAAACATATAGTATGGGCAAGCAGGGAGCTAGAACGATTCGCAGTTAATCCTGGCCTG

TTAGAAACATCAGAAGGCTGTAGACAAATACTGGGACAGCTACAACCATCCCTTCAGACAGGATCAGAAGAACTT

AGATCATTATATAATACAGTAGCAACCCTCTATTGTGTGCATCAAAGGATAGAGATAAAAGACACCAAGGAAGCT

TTAGACAAGATAGAGGAAGAGCAAAACAAAAGTAAGAAAAAAGCACAGCAAGCAGCAGCTGACACAGGACACAGC

AATCAGGTCAGCCAAAATTACCCTATAGTGCAGAACATCCAGGGGCAAATGGTACATCAGGCCATATCACCTAGA

ACTTTAAATGCATGGGTAAAAGTAGTAGAAGAGAAGGCTTTCAGCCCAGAAGTGATACCCATGTTTTCAGCATTA

TCAGAAGGAGCCACCCCACAAGATTTAAACACCATGCTAAACACAGTGGGGGGACATCAAGCAGCCATGCAAATG

TTAAAAGAGACCATCAATGAGGAAGCTGCAGAATGGGATAGAGTGCATCCAGTGCATGCAGGGCCTATTGCACCA

GGCCAGATGAGAGAACCAAGGGGAAGTGACATAGCAGGAACTACTAGTACCCTTCAGGAACAAATAGGATGGATG

ACACATAATCCACCTATCCCAGTAGGAGAAATCTATAAAAGATGGATAATCCTGGGATTAAATAAAATAGTAAGA

ATGTATAGCCCTACCAGCATTCTGGACATAAGACAAGGACCAAAGGAACCCTTTAGAGACTATGTAGACCGATTC

TATAAAACTCTAAGAGCCGAGCAAGCTTCACAAGAGGTAAAAAATTGGATGACAGAAACCTTGTTGGTCCAAAAT

GCGAACCCAGATTGTAAGACTATTTTAAAAGCATTGGGACCAGGAGCGACACTAGAAGAAATGATGACAGCATGT

CAGGGAGTGGGGGGACCCGGCCATAAAGCAAGAGTTTTGGCTGAAGCAATGAGCCAAGTAACAAATCCAGCTACC

ATAATGATACAGAAAGGCAATTTTAGGAACCAAAGAAAGACTGTTAAGTGTTTCAATTGTGGCAAAGAAGGGCAC

ATAGCCAAAAATTGCAGGGCCCCTAGGAAAAAGGGCTGTTGGAAATGTGGAAAGGAAGGACACCAAATGAAAGAT

TGTACTGAGAGACAGGCTAATTTTTTAGGGAAGATCTGGCCTTCCCACAAGGGAAGGCCAGGGAATTTTCTTCAG

AGCAGACCAGAGCCAACAGCCCCACCAGAAGAGAGCTTCAGGTTTGGGGAAGAGACAACAACTCCCTCTCAGAAG

CAGGAGCCGATAGACAAGGAACTGTATCCTTTAGCTTCCCTCAGATCACTCTTTGGCAGCGACCCCTCGTCACAA

TAAAGATAGGGGGGCAATTAAAGGAAGCTCTATTAGATACAGGAGCAGATGATACAGTATTAGAAGAAATGAATT

TGCCAGGAAGATGGAAACCAAAAATGATAGGGGGAATTGGAGGTTTTATCAAAGTAAGACAGTATGATCAGATAC

TCATAGAAATCTGCGGACATAAAGCTATAGGTACAGTATTAGTAGGACCTACACCTGTCAACATAATTGGAAGAA

ATCTGTTGACTCAGATTGGCTGCACTTTAAATTTTCCCATTAGTCCTATTGAGACTGTACCAGTAAAATTAAAGC
```

-continued

CAGGAATGGATGGCCCAAAAGTTAAACAATGGCCATTGACAGAAGAAAAAATAAAAGCATTAGTAGAAATTTGTA

CAGAAATGGAAAAGGAAGGAAAAATTTCAAAAATTGGGCCTGAAAATCCATACAATACTCCAGTATTTGCCATAA

AGAAAAAAGACAGTACTAAATGGAGAAAATTAGTAGATTTCAGAGAACTTAATAAGAGAACTCAAGATTTCTGGG

AAGTTCAATTAGGAATACCACATCCTGCAGGGTTAAAACAGAAAAAATCAGTAACAGTACTGGATGTGGGCGATG

CATATTTTTCAGTTCCCTTAGATAAAGACTTCAGGAAGTATACTGCATTTACCATACCTAGTATAAACAATGAGA

CACCAGGGATTAGATATCAGTACAATGTGCTTCCACAGGGATGGAAAGGATCACCAGCAATATTCCAGTGTAGCA

TGACAAAAATCTTAGAGCCTTTTAGAAAACAAAATCCAGACATAGTCATCTATCAATACATGGATGATTTGTATG

TAGGATCTGACTTAGAAATAGGGCAGCATAGAACAAAAATAGAGGAACTGAGACAACATCTGTTGAGGTGGGGAT

TTACCACACCAGACAAAAAACATCAGAAAGAACCTCCATTCCTTTGGATGGGTTATGAACTCCATCCTGATAAAT

GGACAGTACAGCCTATAGTGCTGCCAGAAAAGGACAGCTGGACTGTCAATGACATACAGAAATTAGTGGGAAAAT

TGAATTGGGCAAGTCAGATTTATGCAGGGATTAAAGTAAGGCAATTATGTAAACTTCTTAGGGGAACCAAAGCAC

TAACAGAAGTAGTACCACTAACAGAAGAAGCAGAGCTAGAACTGGCAGAAAACAGGGAGATTCTAAAAGAACCGG

TACATGGAGTGTATTATGACCCATCAAAAGACTTAATAGCAGAAATACAGAAGCAGGGGCAAGGCCAATGGACAT

ATCAAATTTATCAAGAGCCATTTAAAAATCTGAAAACAGGAAAGTATGCAAGAATGAAGGGTGCCCACACTAATG

ATGTGAAACAATTAACAGAGGCAGTACAAAAAATAGCCACAGAAAGCATAGTAATATGGGGAAAGACTCCTAAAT

TTAAATTACCCATACAAAAGGAAACATGGGAAGCATGGTGGACAGAGTATTGGCAAGCCACCTGGATTCCTGAGT

GGGAGTTTGTCAATACCCCTCCCTTAGTGAAGTTATGGTACCAGTTAGAGAAAGAACCCATAATAGGAGCAGAAA

CTTTCTATGTAGATGGGGCAGCCAATAGGGAAACTAAATTAGGAAAAGCAGGATATGTAACTGACAGAGGAAGAC

AAAAAGTTGTCCCCCTAACGGACACAACAAATCAGAAGACTGAGTTACAAGCAATTCATCTAGCTTTGCAGGATT

CGGGATTAGAAGTAAACATAGTGACAGACTCACAATATGCATTGGGAATCATTCAAGCACAACCAGATAAGAGTG

AATCAGAGTTAGTCAGTCAAATAATAGAGCAGTTAATAAAAAAGGAAAAAGTCTACCTGGCATGGGTACCAGCAC

ACAAAGGAATTGGAGGAAATGAACAAGTAGATAAATTGGTCAGTGCTGGAATCAGGAAAGTACTATTTTTAGATG

GAATAGATAAGGCCCAAGAAGAACATGAGAAATATCACAGTAATTGGAGAGCAATGGCTAGTGATTTTAACCTAC

CACCTGTAGTAGCAAAAGAAATAGTAGCCAGCTGTGATAAATGTCAGCTAAAAGGGGAAGCCATGCATGGACAAG

TAGACTGTAGCCCAGGAATATGGCAGCTAGATTGTACACATTTAGAAGGAAAAGTTATCTTGGTAGCAGTTCATG

TAGCCAGTGGATATATAGAAGCAGAAGTAATTCCAGCAGAGACAGGGCAAGAAACAGCATACTTCCTCTTAAAAT

TAGCAGGAAGATGGCCAGTAAAAACAGTACATACAGACAATGGCAGCAATTTCACCAGTACTACAGTTAAGGCCG

CCTGTTGGTGGGCGGGGATCAAGCAGGAATTTGGCATTCCCTACAATCCCCAAAGTCAAGGAGTAATAGAATCTA

TGAATAAAGAATTAAAGAAAATTATAGGACAGGTAAGAGATCAGGCTGAACATCTTAAGACAGCAGTACAAATGG

CAGTATTCATCCACAATTTTAAAAGAAAAGGGGGGATTGGGGGGTACAGTGCAGGGGAAAGAATAGTAGACATAA

TAGCAACAGACATACAAACTAAAGAATTACAAAAACAAATTACAAAAATTCAAAATTTTCGGGTTTATTACAGGG

ACAGCAGAGATCCAGTTTGGAAAGGACCAGCAAAGCTCCTCTGGAAAGGTGAAGGGGCAGTAGTAATACAAGATA

ATAGTGACATAAAAGTAGTGCCAAGAAGAAAAGCAAAGATCATCAGGGATTATGGAAAACAGATGGCAGGTGATG

ATTGTGTGGCAAGTAGACAGGATGAGGATTAA

HIV Protease

HIV-1 protease is a retroviral aspartyl protease essential for the life-cycle of HIV-1 because it cleaves newly synthesized polyproteins at nine cleavage sites to create the mature protein components of an HIV virion. Without effective HIV protease, HIV virions remain uninfectious.

HIV_protease GenBank: AEU00248.1
(SEQ ID NO: 7)
```
  1 pqitlwkrpl vtikiggqlk ealldtgadd tvleemnlpg
    rwkpkmiggi ggfikvrqyd
 61 qilieicghk aigtvlvgpt pvniigrnll tqigctlnf
```

Furin

Furin is a host cell enzyme that belongs to the subtilisin-like proprotein convertase family and is responsible for the proteolytic cleavage of the HIV envelope polyprotein precursor gp160 to gp120 and gp41.

>sp|P09958|FURIN_HUMAN Furin OS = Homo sapiens
OX = 9606 GN = FURIN PE = 1 SV = 2
(SEQ ID NO: 8)
MELRPWLLWVVAATGTLVLLAADAQGQKVETNTWAVRIPGGPAVANSVAR

KHGELNLGQIFGDYYHEWHRGVTKRSLSPHRPRHSRLQREPQVQWLEQQV

AKRRTKRDVYQEPTDPKFPQQWYLSGVTQRDLNVKAAWAQGYTGHGIVVS

ILDDGIEKNHPDLAGNYDPGASEDVNDQDPDPQPRYTQMNDNRHGTRCAG

EVAAVANNGVCGVGVAYNARIGGVRMLDGEVTDAVEARSLGLNPNHIHIY

SASWGPEDDGKTVDGPARLAEEAFFRGVSQGRGGLGSIFVWASGNGGREH

DSCNCDGYTNSIYTLSISSATQFGNVPWYSEACSSTLATTYSSGNQNEKQ

IVTTDLRQKCTESHTGTSASAPLAAGIIALTLEANKNLTWRDMQHLVVQT

SKPAHLNANDWATNGVGRKVSHSYGYGLLDAGAMVALAQNWTTVAPQRKC

IIDILTEPKDIGKRLEVRKTVTACLGEPNHITRLEHAQARLTLSYNRRGD

LAIHLVSPMGTRSTLLAARPHDYSADGENDWAFMTTHSWDEDPSGEWVLE

IENTSEANNYGTLTKFTLVLYGTAPEGLPVPPESSOCKTLTSSQACVVCE

EGFSLHQKSCVQHCPPGFAPQVLDTHYSTENDVETIRASVCAPCHASCAT

CQGPALTDCLSCPSHASLDPVEQTCSRQSQSSRESPPQQQPPRLPPEVEA

GQRLRAGLLPSHLPEVVAGLSCAFIVLVFVTVELVLQLRSGESFRGVKVY

TMDRGLISYKGLPPEAWQEECPSDSEEDEGRGERTAFIKDQSAL

GeneBank: P09958.2

HIV Immunogenic Compositions/Vaccine Formulations

Provided herein, in some embodiments, are immunogenic compositions comprising a lipid nanoparticle comprising mRNA encoding a membrane-bound HIV Env protein and a mRNA encoding an HIV Gag protein, wherein the lipid nanoparticle comprises an ionizable cationic lipid, a non-cationic lipid, sterol, and a PEG-modified lipid. In some embodiments, the immunogenic compositions comprise a lipid nanoparticle comprising mRNA encoding an HIV Env SOSIP.664 protein (e.g., any of the HIV Env variants described herein) and a mRNA encoding a lentivirus Gag protein.

It should be understood that the HIV mRNA vaccine therapies provided herein include the administration of multiple doses of an HIV mRNA vaccine formulation, each dose separated by at least 1 week, and each dose comprising a combination of mRNA encoding HIV Env protein and mRNA encoding lentivirus Gag protein formulated, for example, in a cationic lipid nanoparticle. It should also be understood that each dose may be different (heterologous) in that the particular HIV strain/isolate from which the mRNA sequence encoding Env protein is obtained/derived may differ and/or the particular dose amount may differ and/or the ratio of mRNA encoding Env v. Gag may differ. Thus, the present disclosure contemplates multiple heterologous boosts of co-formulated mRNA encoding HIV Env and mRNA encoding lentivirus Gag.

In some embodiments, the immunogenic compositions comprise a lipid nanoparticle comprising mRNA encoding a membrane-bound HIV Env protein and a mRNA encoding a lentivirus Gag protein, wherein the ratio of the mRNA encoding a membrane-bound HIV Env protein to the mRNA encoding a lentivirus Gag protein is at least 1:1. For example, the ratio of the mRNA encoding a membrane-bound HIV Env protein to the mRNA encoding a lentivirus Gag protein may be 1:1, 2:1, 3:1, 4:1, or 5:1. In some embodiments, the ratio of the mRNA encoding a membrane-bound HIV Env protein to the mRNA encoding a lentivirus Gag protein is at least 3:2. For example, the ratio of the mRNA encoding a membrane-bound HIV Env protein to the mRNA encoding a lentivirus Gag protein may be 3:2, 4:2, 5:5, 6:2, or 7:2.

Other proportions of mRNA encoding HIV Env protein and mRNA encoding lentivirus Gag protein are contemplated herein. In some embodiments, the immunogenic compositions comprise a lipid nanoparticle comprising mRNA encoding a membrane-bound HIV Env protein and a mRNA encoding a lentivirus Gag protein, wherein the ratio of the mRNA encoding a lentivirus Gag protein to the mRNA encoding a membrane-bound HIV Env protein is at least 1:1. For example, the ratio of the mRNA encoding a lentivirus Gag protein to the mRNA encoding a membrane-bound HIV Env protein may be 1:1, 2:1, 3:1, 4:1, or 5:1. In some embodiments, the ratio of the ratio of the mRNA encoding a lentivirus Gag protein to the mRNA encoding a membrane-bound HIV Env protein is at least 3:2. For example, the ratio of the mRNA encoding a lentivirus Gag protein to the mRNA encoding a membrane-bound HIV Env protein may be 3:2, 4:2, 5:5, 6:2, or 7:2.

In some embodiments, a single dose of an HIV mRNA vaccine of the present disclosure comprises 100 μg to 1000 μg of mRNA. For example, a single dose (e.g., comprising mRNA encoding HIV Env and mRNA encoding Gag formulated in a lipid nanoparticle at a ratio of Env:Gag of 3:2) may be 100 μg to 900 μg, 100 μg to 800 μg, 100 μg to 700 μg, 100 μg to 600 μg, 100 μg to 500 μg, 200 μg to 900 μg, 200 μg to 800 μg, 200 μg to 700 μg, 200 μg to 600 μg, 200 μg to 500 μg, 300 μg to 900 μg, 300 μg to 800 μg, 300 μg to 700 μg, 300 μg to 600 μg, or 300 μg to 600 μg. In some embodiments, a single dose (e.g., comprising mRNA encoding HIV Env and mRNA encoding Gag formulated in a lipid nanoparticle at a ratio of mRNA Env:mRNA Gag of 3:2) is 200 μg, 205 μg, 210 μg, 215 μg, 220 μg, 225 μg, 230 μg, 235 μg, 240 μg, 245 μg, 250 μg, 255 μg, 260 μg, 265 μg, 270 μg, 275 μg, 280 μg, 285 μg, 290 μg, 300 μg, 300 μg, 305 μg, 310 μg, 315 μg, 320 μg, 325 μg, 330 μg, 335 μg, 340 μg, 345 μg, 350 μg, 355 μg, 360 μg, 365 μg, 370 μg, 375 μg, 380 μg, 385 μg, 390 μg, or 400 μg.

The HIV mRNA vaccines of the present disclosure are administered as multiple doses according to particular dosing schedule described herein. In some embodiments, a single initial dose is administered, followed by multiple booster doses. The amount of mRNA in an initial dose, in some embodiments, is less than the amount of mRNA in a subsequent booster dose.

A single dose (e.g., an initial dose) of an HIV mRNA vaccine, as provided herein, in some embodiments comprises 300 μg to 500 μg, or 350 to 450 μg, of mRNA encoding an HIV Env protein of one Clade (e.g., HIV Clade B Env protein, e.g., strain WITO, X2278, JRCSF, JR-FL, B41, 3988, 45_01 dG5, BX08, RHPA, TRJO, YU2, or REJO) and mRNA encoding lentivirus Gag protein (e.g., formulated in a lipid nanoparticle at a ratio of mRNA Env:mRNA Gag of 3:2). In some embodiments, a single dose of an HIV mRNA vaccine comprises 400 μg of mRNA encoding an HIV Env protein of one Clade (e.g., HIV Clade B Env protein, e.g., strain WITO, X2278, JRCSF, JR-FL, B41, 3988, 45_01 dG5, BX08, RHPA, TRJO, YU2, or REJO) and mRNA encoding lentivirus Gag protein (e.g., formulated in a lipid nanoparticle at a ratio of mRNA Env:mRNA Gag of 3:2). It should be understood that the initial dose may include an HIV Clade A Env protein, HIV Clade AC Env protein, HIV Clade AE Env protein, HIV Clade AG Env protein, an HIV Clade B Env protein, an HIV Clade C Env protein, HIV Clade D Env protein, HIV Clade G Env protein, or any other HIV Group M Env protein.

In some embodiments, a single dose (e.g., a booster dose) of an HIV mRNA vaccine comprises 150 μg to 350 μg, or 200 μg to 300 μg, of mRNA encoding an HIV Env protein of a first Clade (e.g., HIV Clade B Env protein, e.g., strain WITO) and mRNA encoding lentivirus Gag protein (e.g., formulated in a lipid nanoparticle at a ratio of mRNA Env:mRNA Gag of 3:2). In some embodiments, a single dose of an HIV mRNA vaccine comprises 240 μg, of mRNA encoding an HIV Env protein of a first Clade (e.g., HIV Clade B Env protein, e.g., strain WITO) and mRNA encoding lentivirus Gag protein (e.g., formulated in a lipid nanoparticle at a ratio of mRNA Env:mRNA Gag of 3:2). It should be understood that any booster dose may include an HIV Clade A Env protein, an HIV Clade AC Env protein, an HIV Clade AE Env protein, an HIV Clade AG Env protein, an HIV Clade B Env protein, an HIV Clade C Env protein, an HIV Clade D Env protein, an HIV Clade G Env protein, or any other HIV Group M Env protein. In some embodiments, a booster dose includes an Env protein of an HIV Clade that is the same as the initial dose. In some embodiments, a booster dose includes an Env protein of an HIV Clade that is different from the initial dose.

In some embodiments, a single dose (e.g., a booster dose) of an HIV mRNA vaccine comprises 150 μg to 350 μg, or 200 μg to 300 μg, of mRNA encoding an HIV Env protein of another Clade (e.g., HIV Clade A Env protein, e.g., strain BG505, Q23, Q842, MI369, KER2008, 0330, RW020, or B1369) and mRNA encoding lentivirus Gag protein (e.g., formulated in a lipid nanoparticle at a ratio of mRNA Env:mRNA Gag of 3:2). In some embodiments, a single dose of an HIV mRNA vaccine comprises 240 μg, of mRNA encoding an HIV Env protein of another Clade (e.g., HIV Clade A Env protein, e.g., strain BG505, Q23, Q842, MI369, KER2008, 0330, RW020, or B1369) and mRNA encoding lentivirus Gag protein (e.g., formulated in a lipid nanoparticle at a ratio of mRNA Env:mRNA Gag of 3:2).

In some embodiments, a single dose (e.g., a booster dose) of an HIV mRNA vaccine comprises 150 μg to 350 μg, or 200 μg to 300 μg, of mRNA encoding an HIV Env protein of yet another Clade (e.g., HIV Clade C Env protein, e.g., strain DU422, 426C, CH505, ZM176, ZM249, ZA012, DU156, CH848, CH1012, MM24, MM45, 001428, BR025, or MW965) and mRNA encoding lentivirus Gag protein (e.g., formulated in a lipid nanoparticle at a ratio of mRNA Env:mRNA Gag of 3:2). In some embodiments, a single dose of an HIV mRNA vaccine comprises 240 μg, of mRNA encoding an HIV Env protein of yet another Clade (e.g., HIV Clade C Env protein, e.g., strain DU422, 426C, CH505, ZM176, ZM249, ZA012, DU156, CH848, CH1012, MM24, MM45, 001428, BR025, or MW965) and mRNA encoding lentivirus Gag protein (e.g., formulated in a lipid nanoparticle at a ratio of mRNA Env:mRNA Gag of 3:2).

In some embodiments, two booster doses are administered simultaneously, e.g., intramuscularly, one in each arm. For example, following an initial 350 μg to 450 μg dose of a vaccine comprising mRNA encoding HIV Clade B Env protein and mRNA encoding lentivirus Gag protein, two booster doses of vaccine may be administered at the same time (e.g., on the same day, e.g., within hours or minutes of each other). One of the two booster doses may include, for example, mRNA encoding HIV Clade A Env protein and mRNA encoding lentivirus Gag protein, and the other of the two booster doses may include, for example, mRNA encoding HIV Clade C Env protein and mRNA encoding lentivirus Gag protein.

As discussed in the Examples, the present disclosure contemplates, in some embodiments, administration of a final low-dose booster. Thus, in some embodiments, a single booster dose of an HIV mRNA vaccine comprises 20 μg to 50 μg of mRNA encoding HIV Env protein and mRNA encoding lentivirus Gag protein. In some embodiments, a single booster dose of an HIV mRNA vaccine comprises 20 μg, 25 μg, 30 μg, 35 μg, 40 μg, 45 μg, or 50 μg of mRNA encoding HIV Env protein and mRNA encoding lentivirus Gag protein.

In some embodiments, the HIV vaccine therapies provided herein also include one or more boost dose of an HIV protein formulation. For example, an HIV protein boost dose may include 25 μg to 500 μg, or 50 μg to 200 μg (e.g., 50 μg, 100 μg, or 200 μg), of soluble HIV Env protein (e.g., SOSIP Env) and/or lentivirus Gag protein, without or without adjuvant (e.g., Adjuplex, or other adjuvant). In some embodiments, a protein boost dose is administered at least one month following an initial mRNA dose. For example, a protein boost dose may be administered at Week 45, 46, 47, 48, 49, 50, 51, 52, 53, 54, 55, 56, 57, 58, 59, or 60 of a vaccine dosing schedule.

Lipid Nanoparticle (LNPs)

HIV RNA (e.g., mRNA) vaccines of the disclosure are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

In some embodiments, an ionizable cationic lipid of the disclosure comprises a compound having structure:

(Compound 1)

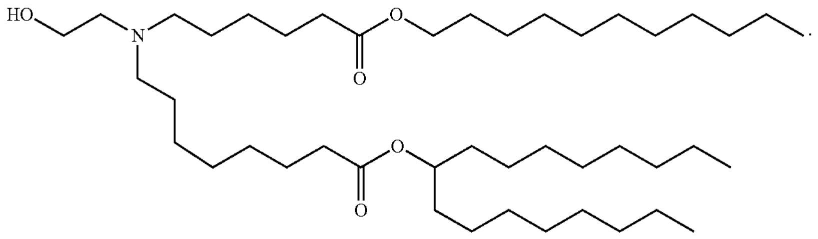

In some embodiments, an ionizable cationic lipid of the disclosure comprises a compound having structure:

(Compound 2)

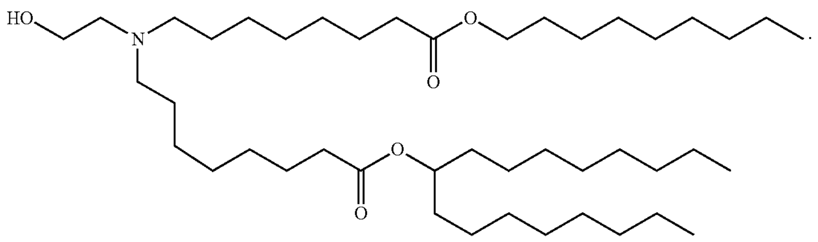

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is PEG-DMG.

In some embodiments, a LNP of the disclosure comprises an N:P ratio of from about 2:1 to about 30:1.

In some embodiments, a LNP of the disclosure comprises an N:P ratio of about 6:1.

In some embodiments, a LNP of the disclosure comprises an N:P ratio of about 3:1.

In some embodiments, a LNP of the disclosure comprises a wt/wt ratio of the ionizable cationic lipid component to the RNA of from about 10:1 to about 100:1.

In some embodiments, a LNP of the disclosure comprises a wt/wt ratio of the ionizable cationic lipid component to the RNA of about 20:1.

In some embodiments, a LNP of the disclosure comprises a wt/wt ratio of the ionizable cationic lipid component to the RNA of about 10:1.

In some embodiments, a LNP of the disclosure has a mean diameter from about 50 nm to about 150 nm.

In some embodiments, a LNP of the disclosure has a mean diameter from about 70 nm to about 120 nm.

Dosing Schedules/Immunization Protocols

The HIV mRNA vaccination methods of the present disclosure, in some embodiments, include administration of an initial dose of the vaccine followed by multiple (e.g., heterologous) booster doses, typically separated by at least one week. Herein, an initial dose formulated with an HIV Env of a particular Clade (e.g., Clade B) may be referred to as an “autologous dose,” whereas a subsequent booster dose formulated with an HIV Env of a different Clade (e.g., Clade A or C) may be referred to as a “heterologous dose.”

In some embodiments, an autologous dose of an HIV mRNA vaccine formulation is administered one or more time(s) within a particular time interval (the first time interval), and then multiple heterologous doses of an HIV mRNA vaccine formulation is administered one or more time(s) within a subsequent time interval (the second time interval). For example, an autologous dose of an HIV mRNA vaccine comprising mRNA encoding HIV Clade B Env (e.g., WITO) and mRNA encoding lentivirus Gag may be administered every 8-12 (e.g., 8, 9, 10, 11, or 12) weeks for 5-7 (e.g., 5, 6, or 7) months, and a heterologous dose of an HIV mRNA vaccine comprising mRNA encoding HIV Clade A Env (e.g., BG505, Q23, Q842, MI369, KER2008, 0330, RW020, or B1369) and mRNA encoding lentivirus Gag, and/or a heterologous dose of an HIV mRNA vaccine comprising mRNA encoding HIV Clade C Env (e.g., DU422, 426C, CH505, ZM176, ZM249, ZA012, DU156, CH848, CH1012, MM24, MM45, 001428, BR025, or MW965) and mRNA encoding lentivirus Gag, may be administered every 8-12 weeks for an additional 5-7 months. Thus, the present disclosure encompasses sequential immunizations initially with mRNA from a first Clade (e.g., Clade B) transmitter/founder envelope (e.g., WITO, X2278, JRCSF, JR-FL, B41, 3988, 45_01dG5, BX08, RHPA, TRJO, YU2, or REJO) followed by mixed heterologous envelopes from 2 different Clades (e.g., Clade A and Clade C), each co-formulated with mRNA encoding lentivirus Gag.

In some embodiments, the interval of time separating an initial dose from a booster dose, and/or separating one booster dose from another booster dose, is 2 to 10 weeks, or 2 to 15 weeks. For example, the interval of time separating an initial dose from a booster dose, and/or separating one booster dose from another booster dose, may be 2, 3, 4, 5, 6, 7, 8, 9, 10, 11, 12, 13, 14, or 15 weeks.

In some embodiments, a first lipid nanoparticle vaccine formulation is administered as multiple doses separated by at least 1 week per administration, prior to administration of a second lipid nanoparticle vaccine formulation. In some embodiments, a second lipid nanoparticle vaccine formulation is administered as multiple doses separated by at least 1 week per administration, after administration of a first lipid nanoparticle vaccine formulation. In some embodiments, a second lipid nanoparticle vaccine formulation and the at least one additional lipid nanoparticle vaccine formulation are administered simultaneously.

In some embodiments, an initial dose is administered (Week 0), and one or more booster dose is administered 10 to 60 weeks later. For example, as shown in the Examples, an initial dose may be administered at Week 0, and then subsequent heterologous booster doses administered at Weeks 11, 19, 27, 35, 43, 47, 51, and/or 56. In some embodiments, an initial dose may be administered at Week 0, and then subsequent heterologous booster doses administered at any one of Weeks 10-12 (e.g., 10, 11, or 12), 18-20 (e.g., 18, 19, or 20), 26-28 (e.g., 26, 27, or 28), 34-36 (e.g., 34, 35, or 36), 42-44 (e.g., 42, 43, or 44), 46-48 (e.g., 46, 47, or 48), 50-52 (e.g., 50, 51, or 52), and/or 55-57 (e.g., 55, 56, or 57). In some embodiments, an initial dose may be administered at Week 0, and then subsequent heterologous booster doses administered at any one of Weeks 5-10, 15-20, 25-30, 35-40, 45-50, and/or 55-60.

In some embodiments, a heterologous booster dose of an HIV mRNA vaccine is administered every 5 weeks, every 6 weeks, every 7 weeks, every 8 weeks, every 9 weeks, or every 10 weeks, for example, for at least 20, at least 22, at least 24, at least 26, at least 28, at least 30, at least 32, at least 34, at least 36, at least 38, at least 40, at least 42, at least 44, at least 46, at least 48, or at least 50 weeks. For example, a heterologous booster dose of an HIV mRNA vaccine may be administered every 5 weeks for at least 20, at least 22, at least 24, at least 26, at least 28, at least 30, at least 32, at least 34, at least 36, at least 38, at least 40, at least 42, at least 44, at least 46, at least 48, or at least 50 weeks. In some embodiments, a heterologous booster dose of an HIV mRNA vaccine may be administered every 6 weeks for at least 20, at least 22, at least 24, at least 26, at least 28, at least 30, at least 32, at least 34, at least 36, at least 38, at least 40, at least 42, at least 44, at least 46, at least 48, or at least 50 weeks. In some embodiments, a heterologous booster dose of an HIV mRNA vaccine may be administered every 7 weeks for at least 20, at least 22, at least 24, at least 26, at least 28, at least 30, at least 32, at least 34, at least 36, at least 38, at least 40, at least 42, at least 44, at least 46, at least 48, or at least 50 weeks. In some embodiments, a heterologous booster dose of an HIV mRNA vaccine may be administered every 8 weeks for at least 20, at least 22, at least 24, at least 26, at least 28, at least 30, at least 32, at least 34, at least 36, at least 38, at least 40, at least 42, at least 44, at least 46, at least 48, or at least 50 weeks. In some embodiments, a heterologous booster dose of an HIV mRNA vaccine may be administered every 9 weeks for at least 20, at least 22, at least 24, at least 26, at least 28, at least 30, at least 32, at least 34, at least 36, at least 38, at least 40, at least 42, at least 44, at least 46, at least 48, or at least 50 weeks. In some embodiments, a heterologous booster dose of an HIV mRNA vaccine may be administered every 10 weeks for at least 20, at least 22, at least 24, at least 26, at least 28, at least 30, at least 32, at least 34, at least 36, at least 38, at least 40, at least 42, at least 44, at least 46, at least 48, or at least 50 weeks.

Alternating intervals of time may also be used, for example, a booster at 10 weeks, a booster at 5 weeks, a booster at 10 weeks, a booster at 5 weeks, and so on.

In some embodiments, a 300-500 μg dose of an HIV mRNA vaccine is administered at Week 0, a 200-300 μg heterologous booster dose of an HIV mRNA vaccine is administered at any one of Weeks 10-12, a 200-300 μg heterologous booster dose of an HIV mRNA vaccine is administered at Weeks 18-20, a 200-250 μg heterologous booster dose of HIV mRNA vaccine is administered at Weeks 28-28, a 200-250 μg heterologous booster dose of an HIV mRNA vaccine is administered at Weeks 34-36, a 200-250 μg heterologous booster dose of an HIV mRNA vaccine is administered at Weeks 42-44, a 200-250 μg heterologous booster dose of an HIV mRNA vaccine is administered at Weeks 46-48, and a 30-50 μg heterologous booster dose of an HIV mRNA vaccine is administered at Weeks 55-57. In some embodiments, a 200-300 μg dose of an HIV protein vaccine is administered at Weeks 50-52.

In some embodiments, a 400 μg dose of HIV mRNA vaccine is administered at Week 0, a 240 μg heterologous booster dose of HIV mRNA vaccine is administered at Week 11, a 240 μg heterologous booster dose of HIV mRNA vaccine is administered at Week 19, a 225 μg heterologous booster dose of HIV mRNA vaccine is administered at Week 27, a 225 μg heterologous booster dose of HIV mRNA vaccine is administered at Week 35, a 225 μg heterologous booster dose of HIV mRNA vaccine is administered at Week 43, a 225 μg heterologous booster dose of HIV mRNA vaccine is administered at Week 47, and a 35 μg heterologous booster dose of HIV mRNA vaccine is administered at Week 56. In some embodiments, an HIV a 100 μg dose of protein vaccine is administered at Week 51.

In some embodiments, an initial dose of an HIV mRNA vaccine comprising mRNA encoding HIV Env (from a first Clade) and mRNA encoding lentivirus Gag is administered at Week 0, a booster dose of an HIV mRNA vaccine comprising mRNA encoding HIV Env (from the first Clade) and mRNA encoding lentivirus Gag is administered at any one of Weeks 10-12, a booster dose of an HIV mRNA vaccine comprising mRNA encoding HIV Env (from the first Clade) and mRNA encoding lentivirus Gag is administered at any one of Weeks 18-20, at least one heterologous booster dose of an HIV mRNA vaccine comprising mRNA encoding HIV Env (from a second Clade, and optionally from a third Clade) and mRNA encoding lentivirus Gag is administered at any one of Weeks 26-28, a heterologous booster dose of an HIV mRNA vaccine comprising mRNA encoding HIV Env (from the second Clade, and optionally from the third Clade) and mRNA encoding lentivirus Gag is administered at any one of Weeks 34-36, at least one heterologous booster dose of an HIV mRNA vaccine comprising mRNA encoding HIV Env (from the second Clade, and optionally from the third Clade) and mRNA encoding lentivirus Gag is administered at any one of Weeks 42-44, at least one heterologous booster dose of an HIV mRNA vaccine comprising mRNA encoding HIV Env (from the second Clade, and optionally from the third Clade) and mRNA encoding lentivirus Gag is administered at any one of Weeks 46-48, and optionally at least one heterologous booster dose of an HIV mRNA vaccine comprising mRNA encoding HIV Env (from the second Clade, and optionally from the third Clade) and mRNA encoding lentivirus Gag is administered at any one of Weeks 55-57.

In some embodiments, the methods comprise administering to the subject a first lipid nanoparticle comprising a mRNA encoding a first HIV Env protein and a mRNA encoding an HIV Gag polyprotein, administering to the subject a second lipid nanoparticle comprising a mRNA encoding a second HIV Env protein and a mRNA encoding an HIV Gag polyprotein, and administering to the subject a third lipid nanoparticle comprising a mRNA encoding a third HIV Env protein and a mRNA encoding an HIV Gag polyprotein, wherein the population of neutralizing antibodies comprises neutralizing antibodies that bind to shared epitopes on proteins from multiple different HIV strains. In some embodiments, at least one of the first, second, and third HIV Env proteins comprises a sequence of an Env protein of an HIV strain obtained from an infected subject who has broad and potent neutralizing antibodies to HIV Env protein. In some embodiments, at least one of the first, second, and third HIV Env proteins comprises a consensus sequence of variants an Env protein of an HIV strain obtained from an infected subject who has broad and potent neutralizing antibodies to HIV Env protein.

In some embodiments, the methods comprise administering to the subject a first lipid nanoparticle comprising a mRNA encoding an HIV Clade B Env protein and a mRNA encoding an HIV Gag polyprotein, administering to the subject a second lipid nanoparticle comprising a mRNA encoding an HIV Clade A Env protein and a mRNA encoding an HIV Gag polyprotein, and administering to the subject a third lipid nanoparticle comprising a mRNA encoding an HIV Clade C Env protein and a mRNA encoding an HIV Gag polyprotein, wherein the population of neutralizing antibodies comprises neutralizing antibodies that bind to shared epitopes on HIV Clade B proteins, HIV Clade A proteins, and HIV Clade C proteins.

In some embodiments, the population comprises neutralizing antibodies that bind to shared epitopes on proteins from multiple Clade B HIV strains, neutralizing antibodies that bind to shared epitopes on proteins from multiple Clade A HIV strains, and neutralizing antibodies that bind to shared epitopes on proteins from multiple Clade C HIV strains. In some embodiments, the population comprises neutralizing antibodies that bind to shared epitopes on proteins from at least five (5) different HIV strains. For example, the population may comprise neutralizing antibodies that bind to shared epitopes on proteins from at least 10 different HIV strains. In some embodiments, the population comprises neutralizing antibodies that bind to shared epitopes on proteins from any of the following HIV strains: JRFL, WITO.33, BG505, AD8, 398F1, CNE8, CNE55, 25710, CE1176, X1632, TRO11, X2278, BJOXO2000, X2632, 246F3, CH119, CE0217, A3, 02, and A3/02.

In some embodiments, none of the first, second, or at least one additional lipid nanoparticles comprise mRNA encoding a soluble HIV Env protein.

Broadly Neutralizing Antibodies and Vaccine Efficacy

Antibody-mediated neutralization of viruses is the direct inhibition of viral infectivity resulting from antibody docking to virus particles (Burton D R et al. *Curr Top Microbiol Immunol* 2001; 260: 109-143). The elicitation of a neutralizing-antibody response is a correlate of protection for many vaccines and contributes to long-lived protection against many viral infections (Plotkin S A et al. *Clin Vaccine Immunol* 2010; 17: 1055-1065). A potent antiviral response may select for variants that allow escape from antibody neutralization and/or effector functions. Neutralization escape mechanisms are diverse and include the selection of amino acid variation in antibody epitopes directly as well as the modulation of structural features to prevent antibody binding.

As is known in the art, the number of antibodies required to neutralize a virus, such as HIV-1, can vary. While in many cases, the neutralization threshold for structurally distinct groups of viruses correlates positively with virion size, in agreement with the "coating theory" (Burton D R et al. 2001), factors that determine the number of antibodies required for neutralization may vary among viruses with different structures, compositions, and entry mechanisms. For example, the small number of functional trimers on the HIV-1 surface allows neutralization with a stoichiometry much lower than that predicted for a virion of this size (Yang X et al. *J Virol* 2005; 79: 3500-3508; and Klasse P J et al. *Virology* 2007; 369: 245-262). See also VanBlargan L A et al. *Microbiology and Molecular Biology Reviews* 2016; 80(4): 989-1010, incorporated herein by reference.

A broad and potent neutralizing antibody response to HIV (e.g., HIV-1) is one that can inhibit infectivity of multiple strains of HIV (e.g., heterologous tier-2 isolates). In some embodiments, a broad and potent neutralizing antibody response can inhibit infectivity of at least 2, at least 3, at least 4, at least 5 strains, at least 10 strains, or at least 15 strains of HIV (e.g., HIV-1). In some embodiments, a broad and potent neutralizing antibody response can inhibit infectivity of 2, 3, 4, 5, 6, 7, 8, 9, 10, 11, 12, 13, 14, or 15, or more of the following HIV strains: JRFL, WITO.33, BG505, AD8, 398F1, CNE8, CNE55, 25710, CE1176, X1632, TRO11, X2278, BJOXO2000, X2632, 246F3, CH119, CE0217, A3, 02, and A3/02. In some embodiments, neutralizing antibodies titers are calculated as the inhibitor concentrations ($IC_{50}$) or reciprocal plasma/serum dilutions ($ID_{50}$) causing a 50% reduction of relative light units. In some embodiments, a broad and neutralizing antibody response is characterized as having an $ID_{50}$ titer of greater than 20. For example, the $ID_{50}$ titer may be greater than 25, 30, 35, 40, 45, 50, 55, 60, 65, 70, 75, 80, 85, 90, 95, or 100. In some embodiments, the $ID_{50}$ titer is greater than 50. In some embodiments, the $ID_{50}$ titer is greater than 100. "Shared epitopes" of HIV antigens, such as HIV Env protein, comprise a common sequence motif to which broadly neutralizing antibodies can bind. Herein, in some embodiments, as discussed throughout the disclosure, the HIV vaccination methods elicit broadly neutralizing antibodies that bind to shared epitopes across multiple strains (e.g., at least 2, at least 3, at least 5, at least 10, or at least 15 strains) of HIV (e.g., HIV-1). In some embodiments, a first lipid nanoparticle vaccine formulation and a second lipid nanoparticle vaccine formulation are administered more than once (e.g., 2 to 10 times, e.g., 2, 3, 4, 5, 6, 7, 8, 9, or 10 times, or more) and in an amount effective at inducing in the subject a population of neutralizing antibodies that bind to shared epitopes on proteins from a first HIV Clade and neutralizing antibodies that bind to shared epitopes on proteins from a (at least a) second HIV Clade. In some embodiments, the population comprises neutralizing antibodies that bind to shared epitopes on proteins from multiple strains (e.g., at least 2, at least 3, at least 5, at least 10, or at least 15 strains) of the first Clade and neutralizing antibodies that bind to shared epitopes on proteins from multiple strains (e.g., at least 2, at least 3, at least 5, at least 10, or at least 15 strains) of the second Clade.

In some embodiments, the methods further comprise administering to the subject at least one additional lipid nanoparticle comprising a mRNA encoding an HIV Env protein from at least one additional Clade (e.g., any one of Group M Clades A-K) and a mRNA encoding an HIV Gag protein. Thus, in some embodiments, the population comprises neutralizing antibodies that bind to shared epitopes on proteins from multiple strains of the at least one additional Clade (e.g., any one of Group M Clades A-K).

Some aspects of the present disclosure provide formulations of the HIV mRNA vaccine, wherein the HIV mRNA vaccine is formulated in an effective amount to produce an antigen specific immune response in a subject (e.g., production of antibodies specific to an HIV antigen). "An effective amount" is a dose of an HIV mRNA vaccine effective to produce an antigen-specific immune response. Also provided herein are methods of inducing an antigen-specific immune response in a subject.

In some embodiments, the antigen-specific immune response is characterized by measuring an anti-HIV antigen (e.g., anti-HIV Env and/or anti-HIV Gag) antibody titer produced in a subject administered an HIV mRNA vaccine as provided herein. An antibody titer is a measurement of the amount of antibodies within a subject, for example, antibodies that are specific to a particular antigen or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the HIV mRNA vaccine.

The HIV therapies (e.g., combination of vaccine formulations and dosing schedule) provided herein produce in a subject broadly neutralizing antibodies against multiple HIV strains. In some embodiments, a broadly neutralizing antibody titer produced in a subject is increased by at least 1 log relative to a control. For example, a broadly neutralizing antibody titer produced in a subject may be increased by at least 1.5, at least 2, at least 2.5, or at least 3 log relative to a control. In some embodiments, a broadly neutralizing antibody titer produced in the subject is increased by 1, 1.5, 2, 2.5 or 3 log relative to a control. In some embodiments, a broadly neutralizing antibody titer produced in the subject is increased by 1-3 log relative to a control. For example, the a broadly neutralizing antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, a broadly neutralizing antibody titer produced in a subject is increased at least 2 times relative to a control. For example, a broadly neutralizing antibody titer produced in a subject may be increased at least 3 times, at least 4 times, at least 5 times, at least 6 times, at least 7 times, at least 8 times, at least 9 times, or at least 10 times relative to a control. In some embodiments, a broadly neutralizing antibody titer produced in the subject is increased 2, 3, 4, 5, 6, 7, 8, 9, or 10 times relative to a control. In some embodiments, a broadly neutralizing antibody titer produced in a subject is increased 2-10 times relative to a control. For example, a broadly neutralizing antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control may be, for example, an unvaccinated subject, or a subject administered a live attenuated HIV vaccine, an inactivated HIV vaccine, or a protein subunit HIV vaccine. A control, in some embodiments, is a broadly neutralizing antibody titer produced in a subject who has not been administered an HIV mRNA vaccine. In some embodiments, a control is a broadly neutralizing antibody titer produced in a subject administered a recombinant or purified HIV protein vaccine. Recombinant protein vaccines typically include protein antigens that either have been produced in a heterologous expression system (e.g., bacteria or yeast) or purified from large amounts of the pathogenic organism.

In some embodiments, an effective amount of an HIV mRNA vaccine is a dose that is reduced compared to the standard of care dose of a recombinant HIV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified HIV protein vaccine, or a live attenuated or inactivated HIV vaccine, or an HIV VLP vaccine, that a physician/clinician or other medical professional would administer to a subject to treat or prevent HIV, or an HIV-related condition, while following the standard of care guideline for treating or preventing HIV, or an HIV-related condition.

In some embodiments, a broadly neutralizing antibody titer produced in a subject administered an effective amount of an HIV mRNA vaccine is equivalent to a broadly neutralizing antibody titer produced in a control subject administered a standard of care dose of a recombinant or purified HIV protein vaccine, or a live attenuated or inactivated HIV vaccine, or an HIV VLP vaccine.

In some embodiments, an effective amount of an HIV mRNA vaccine is a dose equivalent to an at least 2-fold reduction in a standard of care dose of a recombinant or purified HIV protein vaccine. For example, an effective amount of an HIV mRNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified HIV protein vaccine. In some embodiments, an effective amount of an HIV mRNA vaccine is a dose equivalent to an at least at least 100-fold, at least 500-fold, or at least 1000-fold reduction in a standard of care dose of a recombinant or purified HIV protein vaccine. In some embodiments, an effective amount of an HIV mRNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified HIV protein vaccine. In some embodiments, a broadly neutralizing antibody titer produced in a subject administered an effective amount of an HIV mRNA vaccine is equivalent to a broadly neutralizing antibody titer produced in a control subject administered the standard of care dose of a recombinant or protein HIV protein vaccine, or a live attenuated or inactivated HIV vaccine, or an HIV VLP vaccine. In some embodiments, an effective amount of an HIV mRNA vaccine is a dose equivalent to a 2-fold to 1000-fold (e.g., 2-fold to 100-fold, 10-fold to 1000-fold) reduction in the standard of care dose of a recombinant or purified HIV protein vaccine, wherein a broadly neutralizing antibody titer produced in the subject is equivalent to a broadly neutralizing antibody titer produced in a control subject administered the standard of care dose of a recombinant or purified HIV protein vaccine, or a live attenuated or inactivated HIV vaccine, or an HIV VLP vaccine.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(ARU-ARV)/ARU\times 100;\text{ and}$$

$$\text{Efficacy}=(1-RR)\times 100.$$

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$Effectiveness=(1-OR)\times 100.$$

In some embodiments, efficacy of the HIV vaccine is at least 60% relative to unvaccinated control subjects. For example, efficacy of the HIV vaccine may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective viral infection into the host. In some embodiments, the effective amount of an HIV vaccine of the present disclosure is sufficient to provide sterilizing immunity in the subject for at least 1 year. For example, the effective amount of an HIV vaccine of the present disclosure is sufficient to provide sterilizing immunity in the subject for at least 2 years, at least 3 years, at least 4 years, or at least 5 years. In some embodiments, the effective amount of an HIV vaccine of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of an HIV vaccine of the present disclosure is sufficient to produce detectable levels of HIV antigen as measured in serum of the subject at 1-72 hours post administration.

Titer. An antibody titer is a measurement of the amount of antibodies within a subject, for example, antibodies that are specific to a particular antigen (e.g., an anti-HIV antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of an HIV vaccine of the present disclosure is sufficient to produce a 1,000-10,000 neutralizing antibody titer produced by neutralizing antibody against the HIV antigen as measured in serum of the subject at 1-72 hours post administration. In some embodiments, the effective amount is sufficient to produce a 1,000-5,000 neutralizing antibody titer produced by neutralizing antibody against the HIV antigen as measured in serum of the subject at 1-72 hours post administration. In some embodiments, the effective amount is sufficient to produce a 5,000-10,000 neutralizing antibody titer produced by neutralizing antibody against the HIV antigen as measured in serum of the subject at 1-72 hours post administration.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, a geometric mean, which is the nth root of the product of n numbers, is generally used to describe proportional growth. Geometric mean, in some embodiments, is used to characterize antibody titer produced in a subject.

mRNA Design, Elements, and Manufacturing

Messenger RNA (mRNA) is any ribonucleic acid that encodes a (at least one) protein (a naturally-occurring, non-naturally-occurring, or modified polymer of amino acids) and can be translated to produce the encoded protein in vitro, in vivo, in situ, or ex vivo. The skilled artisan will appreciate that, except where otherwise noted, nucleic acid sequences set forth in the instant application may recite "T"s in a representative DNA sequence but where the sequence represents RNA (e.g., mRNA), the "T"s would be substituted for "U"s. Thus, any of the DNAs disclosed and identified by a particular sequence identification number herein also disclose the corresponding RNA (e.g., mRNA) sequence complementary to the DNA, where each "T" of the DNA sequence is substituted with "U."

An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in a vaccine of the present disclosure. It is contemplated that the HIV vaccines of the present disclosure comprise at least one (one or more) ribonucleic acid (RNA) having an open reading frame encoding at least one HIV antigen.

In some embodiments, the RNA is a messenger RNA (mRNA) having an open reading frame encoding at least one HIV antigen. In some embodiments, the RNA (e.g., mRNA) further comprises a (at least one) 5' UTR, 3' UTR, a polyA tail and/or a 5' cap.

mRNA of the present disclosure, in some embodiments, is not naturally-occurring. That is, the mRNA in some embodiments, is engineered, for example, chemically synthesized or produced using recombinant nucleic acid technology. In some embodiments, at least one mRNA of the compositions provided herein is naturally-occurring.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure. Non-limiting examples of 5' UTR sequences include

```
                                            (SEQ ID NO: 10)
GGGAAAUAAGAGAGAAAAGAAGAGUAAGAAGAAAUAUAAGAGCCACC
and
                                            (SEQ ID NO: 11)
GGGAAAUAAGAGAGAAAAGAAGAGUAAGAAGAAAUAUAAGACCCCGGCGC

CGCCACC
```

A "3' untranslated region" (UTR) refers to a region of an mRNA that is directly downstream (i.e., 3') from the stop codon (i.e., the codon of an mRNA transcript that signals a termination of translation) that does not encode a polypeptide. 3' UTR: Non-limiting examples of 3' UTR sequences include

```
                                            (SEQ ID NO: 12)
UGAUAAUAGGCUGGAGCCUCGGUGGCCAUGCUUCUUGCCCCUUGGGCCUC

CCCCCAGCCCCUCCUCCCCUUCCUGCACCCGUACCCCCGUGGUCUUUGAA

UAAAGUCUGAGUGGGCGGC
and
```

-continued (SEQ ID NO: 13)
UGAUAAUAGGCUGGAGCCUCGGUGGCCUAGCUUCUUGCCCCUUGGGCCUC

CCCCCAGCCCCUCCUCCCCUUCCUGCACCCGUACCCCCGUGGUCUUUGAA

UAAAGUCUGAGUGGGCGGC

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, the length of a mRNA is 200 to 3,000 nucleotides. For example, the length of a mRNA may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

Sequence Optimization

In some embodiments, an ORF encoding an Env and/or Gag protein of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% (e.g., less than 90%, less than 85%, less than 80%, or less than 75%) sequence identity to a naturally-occurring or wild-type sequence ORF (e.g., a naturally-occurring or wild-type mRNA sequence encoding an ENV or Gag protein). In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding an ENV or Gag protein).

In some embodiments, a codon optimized mRNA may be one in which the levels of G/C are enhanced. The G/C-content of nucleic acid molecules (e.g., mRNA) may influence the stability of the mRNA. mRNA having an increased amount of guanine (G) and/or cytosine (C) residues may be functionally more stable than mRNA containing a large amount of adenine (A) and thymine (T) or uracil (U) nucleotides. As an example, WO2002098443 (published Dec. 12, 2002) discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, at least one RNA (e.g., mRNA) of HIV vaccines of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

HIV mRNA vaccines of the present disclosure comprise, in some embodiments, at least one mRNA having an open reading frame encoding at least one Env and/or Gag protein, wherein the mRNA comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Thus, mRNA of the disclosure can comprise standard nucleotides and nucleosides, naturally-occurring nucleotides and nucleosides, non-naturally-occurring nucleotides and nucleosides, or any combination thereof.

The mRNA in some embodiments, comprises non-natural modified nucleotides that are introduced during synthesis or post-synthesis of the mRNA to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a mRNA may be chemically modified.

The present disclosure provides for modified nucleosides and nucleotides of a mRNA. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. mRNA can comprise a region or regions of linked nucleosides. Such regions may have variable backbone linkages. The linkages can be standard phosphodiester linkages, in which case the mRNA would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in the mRNA having at least one chemical modification. One example of such non-standard base pairing is the base pairing between the modified nucleotide inosine and adenine, cytosine or uracil. Any combination of base/sugar or linker may be incorporated into mRNA of the present disclosure.

In some embodiments, modified nucleobases in mRNA comprise 1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in mRNA comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a MRNA of the disclosure comprises 1-methyl-pseudouridine (m1ψ) substitutions at one or more or all uridine positions of the mRNA. In some embodiments, a MRNA of the disclosure comprises 1-methyl-pseudouridine (m1ψ) substitutions at one or more or all uridine positions of the mRNA and 5-methyl cytidine substitutions at one or more or all cytidine positions of the mRNA. In some embodiments, a MRNA of the disclosure comprises pseudouridine (ψ) substitutions at one or more or all uridine positions of the mRNA. In some embodiments, a MRNA of the disclosure comprises pseudouridine (ψ) substitutions at one or more or all uridine positions of the mRNA and 5-methyl cytidine substitutions at one or more or all cytidine positions of the mRNA. In some embodiments, a mRNA of the disclosure comprises uridine at one or more or all uridine positions of the mRNA.

In some embodiments, mRNA is uniformly modified (e.g., fully modified, modified throughout the entire sequence) for a particular modification. For example, mRNA can be uniformly modified with 1-methyl-pseudouridine, meaning that all uridine residues in the mRNA sequence are replaced with 1-methyl-pseudouridine. Similarly, mRNA can be uniformly modified for any type of nucleoside residue present in the sequence by replacement with a modified residue such as those set forth above.

The mRNA may contain from about 1% to about 100% modified nucleotides (either in relation to overall nucleotide content, or in relation to one or more types of nucleotide, i.e., any one or more of A, G, U or C) or any intervening percentage. It will be understood that any remaining percentage is accounted for by the presence of unmodified A, G, U, or C. The mRNA may contain at a minimum 1% and at maximum 100% modified nucleotides, or any intervening percentage. In some embodiments, at least 5%, at least 10%, at least 25%, at least 50%, at least 80%, at least 90% or 100% of the uracil in the mRNA is replaced with a modified uracil (e.g., a 5-substituted uracil).

In Vitro Transcription of RNA cDNA encoding the polynucleotides described herein may be transcribed using an in vitro transcription (IVT) system. In vitro transcription of RNA is known in the art and is described in WO2014/152027, which is incorporated by reference herein in its entirety.

In some embodiments, the mRNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of HIV mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5 ' to and operably linked to the gene of interest.

In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis

Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions

Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present invention may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

ADDITIONAL EMBODIMENTS

1. A method of inducing in a subject an immune response to human immunodeficiency virus (HIV), the method comprising:
(a) during a first period of time, administering to a subject an initial dose and multiple autologous boost doses of a first composition comprising a messenger RNA (mRNA) encoding an HIV envelope (Env) protein and an mRNA encoding a lentivirus group-specific antigen (Gag) protein formulated in a lipid nanoparticle;
(b) during a second period of time, administering to the subject multiple heterologous boost doses of a second composition comprising an mRNA encoding an HIV Env protein and an mRNA encoding a lentivirus Gag protein formulated in a lipid nanoparticle; and
(c) producing in the subject a broadly neutralizing antibody response against multiple strains of HIV.
2. The method of paragraph 1, wherein the broadly neutralizing antibody response comprises a production of neutralizing antibodies that bind to shared epitopes on proteins from the multiple strains of HIV.
3. The method of paragraph 2, wherein the broadly neutralizing antibody response comprises an $ID_{50}$ titer of greater than 20 or greater than 50.
4. The method of paragraph 1, wherein (i) the first period of time is 1-30 weeks following administration of the initial dose of the first composition and/or (ii) the second period of time is 8-60 weeks following administration of the initial dose of the first composition.

5. The method of paragraph 1, wherein the time between any two doses of the first composition of (a) and/or the second composition of (b) is at least 1 week, is at least 4 weeks, or is 4-12 weeks.

6. The method of paragraph 1, wherein the HIV is HIV type-1 (HIV-1).

7. The method of paragraph 1, wherein the ratio of the mRNA encoding an HIV Env protein to the mRNA encoding an HIV Gag protein of in the first composition of (a) and/or in the second composition of (b) is 2:1 or 3:2.

8. The method of paragraph 1, wherein the first composition and/or the second composition further comprises an mRNA encoding an HIV protease.

9. The method of paragraph 8, wherein the ratio of the mRNA encoding an HIV Gag protein to the mRNA encoding an HIV protease to is at least 1:5, at least 1:10, at least 1:20, at least 1:40, at least 1:60, or at least 1:80.

10. The method of paragraph 1, wherein the first and/or second composition further comprises an mRNA encoding furin.

11. The method of paragraph 10, wherein the ratio of the mRNA encoding furin to the mRNA encoding an HIV Env protein is at least 1:5.

12. The method of paragraph 1, wherein the HIV Env protein of the first composition of (a) is selected from an HIV Env protein of Group M Clade A-K, wherein the HIV Env protein of the second composition of (b) is selected from an HIV Env protein of Group M Clade A-K, and wherein the Clade(s) of the HIV Env protein of the first composition of (a) is different from the Clade(s) of the HIV Env protein of the second composition of (b).

13. The method of paragraph 1, wherein the HIV Env protein of the first composition of (a) and/or the second composition of (b) comprises HIV Env SOSIP.664 mutations.

14. The method of paragraph 1, wherein the HIV Env protein of the first composition of (a) and/or the second composition of (b) is a membrane-bound HIV Env protein.

15. The method of paragraph 1, wherein the cytosolic portion of the HIV Env protein of the first composition of (a) and/or the second composition of (b) is partially truncated.

16. The method of paragraph 14, wherein the membrane-bound HIV Env protein is gp150 or gp160.

17. The method of paragraph 1, wherein the HIV Env protein of the first composition of (a) and/or the second composition of (b) comprises a sequence of an Env protein, or a consensus sequence of variants an Env protein, of an HIV strain obtained from an infected subject who has broadly neutralizing antibodies to HIV Env protein.

18. The method of paragraph 1, wherein the HIV Env protein of the first composition of (a) and/or the second composition of (b) comprises a sequence of a variant Env protein of an HIV strain that engages one or multiple UCA antibodies to HIV Env protein from the lineages of known broadly neutralizing antibodies.

19. The method of paragraph 1, wherein the HIV Env protein of the first composition of (a) and/or the second composition of (b) comprises:

(i) a mutation selected from 153E, 190G and N276D, relative to strain WITO4160.27 HIV Env protein, or other mutations suitable to remove the glycans at positions 188 and 276, optionally wherein the HIV Env protein of the first composition of (a) and/or the second composition of (b) further comprises a disulfide bridge at 113C-432GCG;

(ii) a mutation selected from N460D and N463D relative to strain BG505 HIV Env protein, or other suitable mutations to remove the glycans at positions 460 and 463;

(iii) a mutation selected from K295N, D386N, and 375Y, relative to strain DU422.1, C DU156.12, DU172.17, ZM176.66, or CNE58 HIV Env protein, optionally wherein the HIV Env protein of the first composition of (a) and/or the second composition of (b) further comprises a disulfide bridge at 133C-432GCG; or (iv) a mutation selected from T322N and S375Y, relative to strain WITO4160.27 HIV Env protein, optionally wherein the HIV Env protein of the first composition of (a) and/or the second composition of (b) further comprises a disulfide bridge at 113C-429GCG.

20. The method of paragraph 1, wherein the HIV Env protein of the first composition of (a) and/or the second composition of (b) is a tier-2 Env with all the major glycan holes filled in by insertion of the missing glycans.

21. The method of paragraph 1, wherein the lentivirus is selected from human immunodeficiency virus (HIV), simian immunodeficiency virus (SIV), and murine leukemia virus (muLV).

22. The method of paragraph 1, wherein the lentivirus-derived Gag is replaced by VSV-ΔG or VSV core protein.

23. A method of inducing in a subject an immune response to human immunodeficiency virus (HIV), the method comprising:

administering to the subject a first lipid nanoparticle comprising a messenger RNA (mRNA) encoding an HIV envelope (Env) protein from a first Clade and an mRNA encoding a lentivirus group-specific antigen (Gag) protein; and administering to the subject a second lipid nanoparticle comprising a mRNA encoding an HIV Env protein from a second Clade and a mRNA encoding a lentivirus Gag protein, wherein the first lipid nanoparticle and the second lipid nanoparticle are administered more than once and in an amount effective at inducing in the subject a population of neutralizing antibodies that bind to shared epitopes on proteins from the first Clade and neutralizing antibodies that bind to shared epitopes on proteins from the second Clade.

24. The method of paragraph 23, wherein the HIV is HIV type-1.

25. The method of paragraph 23, wherein the population comprises neutralizing antibodies that bind to shared epitopes on proteins from multiple strains of the first Clade and neutralizing antibodies that bind to shared epitopes on proteins from multiple strains of the second Clade.

26. The method of paragraph 23 further comprising administering to the subject at least one additional lipid nanoparticle comprising an mRNA encoding an HIV Env protein from at least one additional Clade and a mRNA encoding an HIV Gag protein.

27. The method of paragraph 26, wherein the population comprises neutralizing antibodies that bind to shared epitopes on proteins from multiple strains of the at least one additional Clade.

28. The method of paragraph 23, wherein the first nanoparticle comprises a ratio of the mRNA encoding an HIV Env protein to the mRNA encoding an HIV Gag protein of at least 1:1, and/or wherein the second nanoparticle comprises a ratio the mRNA encoding an HIV Env protein to the mRNA encoding an HIV Gag protein of at least 1:1.

29. The method of paragraph 28, wherein the first nanoparticle comprises a ratio of the mRNA encoding an HIV Env protein to the mRNA encoding an HIV Gag protein of at least 3:2, and/or wherein the second nanoparticle comprises a ratio the mRNA encoding an HIV Env protein to the mRNA encoding an HIV Gag protein of at least 3:2.

30. The method of paragraph 23, wherein the HIV Env protein comprises mutations, relative to wild-type HIV Env protein, that favor a closed conformation.

31. The method of paragraph 23, wherein the HIV Env protein comprises glycan knock-in or knock-out modifications.

32. The method of paragraph 23, wherein the HIV Env protein is a stabilized soluble Env protein.

33. The method of paragraph 32, wherein the HIV Env protein is an HIV Env SOSIP.664 protein.

34. The method of paragraph 23, wherein the HIV Env protein is a membrane-bound HIV Env protein.

35. The method of paragraph 34, wherein the cytosolic portion of the protein is truncated.

36. The method of paragraph 34, wherein the membrane-bound HIV Env protein is gp150 or gp160.

37. The method of paragraph 23, wherein the lentivirus is selected from human immunodeficiency virus (HIV), simian immunodeficiency virus (SIV), and murine leukemia virus (muLV).

38. The method of paragraph 23, wherein the first Clade, the second Clade, and the at least one additional Clade are selected from the group consisting of HIV Group M Clades A-K and related circulating recombinant forms (CRFs).

39. The method of paragraph 23, wherein the first lipid nanoparticle and the second nanoparticle are administered sequentially.

40. The method of paragraph 39, wherein the first lipid nanoparticle is administered as multiple doses separated by at least 1 week per administration, prior to administration of the second lipid nanoparticle.

41. The method of paragraph 39, wherein the second lipid nanoparticle is administered as multiple doses separated by at least 1 week per administration, after administration of the first lipid nanoparticle.

42. The method of paragraph 23, wherein the second lipid nanoparticle and the at least one additional lipid nanoparticle are administered simultaneously.

43. The method of paragraph 38, wherein the first Clade is Clade A.

44. The method of paragraph 38, wherein the second Clade is Clade A.

45. The method of paragraph 43 or 44, wherein the HIV Env protein is selected from HIV Clade A BG505, Q23, Q842, MI369, KER2008, 0330, RW020, and BI369 strain Env proteins.

46. The method of paragraph 38, wherein the first Clade is Clade AC.

47. The method of paragraph 38, wherein the second Clade is Clade AC.

48. The method of paragraph 46 or 47, wherein the HIV Env protein is an HIV Clade AC 3301 strain Env proteins.

49. The method of paragraph 38, wherein the first Clade is Clade AE.

50. The method of paragraph 38, wherein the second Clade is Clade AE.

51. The method of paragraph 49 or 50, wherein the HIV Env protein is selected from HIV Clade AE C2101, CM244, and BJOXO28000 strain Env proteins.

52. The method of paragraph 38, wherein the first Clade is Clade AG.

53. The method of paragraph 38, wherein the second Clade is Clade AG.

54. The method of paragraph 52 or 53, wherein the HIV Env protein is selected from HIV Clade AG DJ263 and T280 strain Env proteins.

55. The method of paragraph 38, wherein the first Clade is Clade B.

56. The method of paragraph 38, wherein the second Clade is Clade B.

57. The method of paragraph 55 or 56, wherein the HIV Env protein is selected from HIV Clade B WITO, X2278, JRCSF, JR-FL, B41, 3988, 45_0ldG5, BX08, RHPA, TRJO, YU2, and REJO strain Env proteins.

58. The method of paragraph 38, wherein the first Clade is Clade C.

59. The method of paragraph 38, wherein the second Clade is Clade C.

60. The method of paragraph 58 or 59, wherein the HIV Env protein is selected from HIV Clade C DU422, 426C, CH505, ZM176, ZM249, ZA012, DU156, CH848, CH1012, MM24, MM45, 001428, BR025, and MW965 strain Env proteins.

61. The method of paragraph 38, wherein the first Clade is Clade D.

62. The method of paragraph 38, wherein the second Clade is Clade D.

63. The method of paragraph 61 or 62, wherein the HIV Env protein is an HIV Clade D A07412M1 strain Env protein.

64. The method of paragraph 38, wherein the first Clade is Clade G.

65. The method of paragraph 38, wherein the second Clade is Clade G.

66. The method of paragraph 64 or 65, wherein the HIV Env protein is selected from HIV Clade G X1193 and P1981 strain Env proteins.

67. The method of paragraph 23, wherein the HIV Env protein comprises a sequence of an Env protein of an HIV strain obtained from an infected subject who has broadly neutralizing antibodies to HIV Env protein.

68. The method of paragraph 23, wherein the HIV Env protein comprises a consensus sequence of variants an Env protein of an HIV strain obtained from an infected subject who has broadly neutralizing antibodies to HIV Env protein.

69. The method of paragraph 23, wherein the method comprises administering to the subject a first lipid nanoparticle comprising a mRNA encoding a first HIV Env protein and a mRNA encoding an HIV Gag polyprotein;

administering to the subject a second lipid nanoparticle comprising a mRNA encoding a second HIV Env protein and a mRNA encoding an HIV Gag polyprotein; and administering to the subject a third lipid nanoparticle comprising a mRNA encoding a third HIV Env protein and a mRNA encoding an HIV Gag polyprotein;

wherein the population of neutralizing antibodies comprises neutralizing antibodies that bind to shared epitopes on proteins from multiple different HIV strains.

70. The method of paragraph 69, wherein at least one of the first, second, and third HIV Env proteins comprises a sequence of an Env protein of an HIV strain obtained from an infected subject who has broadly neutralizing antibodies to HIV Env protein.

71. The method of paragraph 69, wherein at least one of the first, second, and third HIV Env proteins comprises a consensus sequence of variants an Env protein of an HIV strain obtained from an infected subject who has broadly neutralizing antibodies to HIV Env protein.

72. The method of paragraph 23, wherein the method comprises administering to the subject a first lipid nanoparticle comprising a mRNA encoding an HIV Clade B Env protein and a mRNA encoding an HIV Gag polyprotein;

administering to the subject a second lipid nanoparticle comprising a mRNA encoding an HIV Clade A Env protein and a mRNA encoding an HIV Gag polyprotein; and administering to the subject a third lipid nanoparticle comprising a mRNA encoding an HIV Clade C Env protein and a mRNA encoding an HIV Gag polyprotein;

wherein the population of neutralizing antibodies comprises neutralizing antibodies that bind to shared epitopes on HIV Clade B proteins, HIV Clade A proteins, and HIV Clade C proteins.

73. The method of paragraph 72, wherein the population comprises neutralizing antibodies that bind to shared epitopes on proteins from multiple Clade B HIV strains, neutralizing antibodies that bind to shared epitopes on proteins from multiple Clade AN HIV strains, and neutralizing antibodies that bind to shared epitopes on proteins from multiple Clade C HIV strains.

74. The method of paragraph 23, wherein the population comprises neutralizing antibodies that bind to shared epitopes on proteins from at least 5 different HIV strains.

75. The method of paragraph 74, wherein the population comprises neutralizing antibodies that bind to shared epitopes on proteins from at least 10 different HIV strains.

76. The method of paragraph 75, wherein the population comprises neutralizing antibodies that bind to shared epitopes on proteins from any of the following HIV strains: JRFL, WITO.33, BG505, AD8, 398F1, CNE8, CNE55, 25710, CE1176, X1632, TRO11, X2278, BJOXO2000, X2632, 246F3, CH119, CE0217, A3, 02, and A3/02.

77. The method of paragraph 23, wherein none of the first, second, or at least one additional lipid nanoparticles comprise mRNA encoding a soluble HIV Env protein.

78. An immunogenic composition, comprising a lipid nanoparticle comprising mRNA encoding a membrane-bound HIV Env protein and a mRNA encoding an HIV Gag protein, wherein the lipid nanoparticle comprises an ionizable cationic lipid, a non-cationic lipid, sterol, and a PEG-modified lipid.

79. An immunogenic composition, comprising a lipid nanoparticle comprising mRNA encoding an HIV Env SOSIP.664 protein and a mRNA encoding an HIV Gag protein.

80. An immunogenic composition, comprising a lipid nanoparticle comprising mRNA encoding a membrane-bound HIV Env protein and a mRNA encoding an HIV Gag protein, wherein the ratio of the mRNA encoding a membrane-bound HIV Env protein to the mRNA encoding an HIV Gag protein is at least 3:2.

81. The method of any one of the preceding paragraphs, wherein the Env protein encoded by the mRNA of the first composition and the Env protein encoded by the mRNA of the second composition are from difference clades.

82. The method of any one of the preceding paragraphs, wherein the first composition the second composition are administered more than once and in an amount effective at inducing in the subject a population of neutralizing antibodies that bind to shared epitopes on HIV Env proteins from different Clades.

83. The method of any one of the preceding paragraphs, wherein the first composition comprises mRNA encoding an HIV Env protein selected from HIV Clade A Env proteins, HIV Clade AC Env proteins, HIV Clade AE Env proteins, HIV Clade AG Env proteins, HIV Clade B Env proteins, HIV Clade C Env proteins, HIV Clade D Env proteins, and HIV Clade G Env proteins.

84. The method of any one of the preceding paragraphs, wherein the first composition comprises a first mRNA and a second mRNA, each encoding an HIV Env protein selected from HIV Clade A Env proteins, HIV Clade AC Env proteins, HIV Clade AE Env proteins, HIV Clade AG Env proteins, HIV Clade B Env proteins, HIV Clade C Env proteins, HIV Clade D Env proteins, and HIV Clade G Env proteins, wherein the Env protein encoded by the first mRNA and the Env protein encoded by the second mRNA are from different clades.

85. The method of any one of the preceding paragraphs, wherein the first composition comprises a first mRNA, a second mRNA, and a third mRNA, each encoding an HIV Env protein selected from HIV Clade A Env proteins, HIV Clade AC Env proteins, HIV Clade AE Env proteins, HIV Clade AG Env proteins, HIV Clade B Env proteins, HIV Clade C Env proteins, HIV Clade D Env proteins, and HIV Clade G Env proteins, wherein the Env protein encoded by the first mRNA, the Env protein encoded by the second mRNA, and the Env protein encoded by the third mRNA are from different clades.

86. The method of any one of the preceding paragraphs, wherein the second composition comprises mRNA encoding an HIV Env protein selected from HIV Clade A Env proteins, HIV Clade AC Env proteins, HIV Clade AE Env proteins, HIV Clade AG Env proteins, HIV Clade B Env proteins, HIV Clade C Env proteins, HIV Clade D Env proteins, and HIV Clade G Env proteins, and wherein the Env proteins encoded by the mRNA of the first composition and the Env proteins encoded by the mRNA of the second composition are from different clades.

87. The method of any one of the preceding paragraphs, wherein the second composition comprises a first mRNA and a second mRNA, each encoding an HIV Env protein selected from HIV Clade A Env proteins, HIV Clade AC Env proteins, HIV Clade AE Env proteins, HIV Clade AG Env proteins, HIV Clade B Env proteins, HIV Clade C Env proteins, HIV Clade D Env proteins, and HIV Clade G Env proteins, wherein the Env protein encoded by the first mRNA and the Env protein encoded by the second mRNA are from different clades, and wherein the Env proteins encoded by the mRNA of the first composition and the Env proteins encoded by the mRNA of the second composition are from different clades.

88. The method of any one of the preceding paragraphs, wherein the second composition comprises a first mRNA, a second mRNA, and a third mRNA, each encoding an HIV Env protein selected from HIV Clade A Env proteins, HIV Clade AC Env proteins, HIV Clade AE Env proteins, HIV Clade AG Env proteins, HIV Clade B Env proteins, HIV Clade C Env proteins, HIV Clade D Env proteins, and HIV Clade G Env proteins, wherein the Env protein encoded by the first mRNA, the Env protein encoded by the second mRNA, and the Env protein encoded by the third mRNA are from different clades, and wherein the Env proteins encoded by the mRNA of the first composition and the Env proteins encoded by the mRNA of the second composition are from different clades.

89. The method of any one of the preceding paragraphs, wherein the HIV Clade A Env proteins are selected from HIV Clade A BG505, Q23, Q842, MI369, KER2008, 0330, RW020 or BI369 strain Env proteins.

90. The method of any one of the preceding paragraphs, wherein the HIV Clade AC Env proteins are HIV Clade AC 3301 strain Env proteins.

91. The method of any one of the preceding paragraphs, wherein the HIV Clade AE Env proteins are selected from HIV Clade AE C2101, CM244, and BJOXO28000 strain Env proteins.

92. The method of any one of the preceding paragraphs, wherein the HIV Clade AG Env proteins are selected from HIV Clade AG DJ263 and T280 strain Env proteins.

93. The method of any one of the preceding paragraphs, wherein the HIV Clade B Env proteins are selected from HIV Clade B X2278, JRCSF, JR-FL, B41, 3988, 45_01dG5, BX08, RHPA, TRJO, YU2, and REJO strain Env proteins.

94. The method of any one of the preceding paragraphs, wherein the HIV Clade C Env proteins are selected from HIV Clade C DU422, 426C, CH505, ZM176, ZM249, ZA012, DU156, CH848, CH1012, MM24, MM45, 001428, BR025, and MW965 strain Env proteins.

95. The method of any one of the preceding paragraphs, wherein the HIV Clade D Env proteins are selected from HIV Clade D A07412M1 strain Env proteins.

96. The method of any one of the preceding paragraphs, wherein the HIV Clade G Env proteins are selected from HIV Clade G X1193 and P1981 strain Env proteins.

97. The method of any one of the preceding paragraphs, wherein the RNA comprises a chemical modification.

98. The method of any one of the preceding paragraphs, wherein the chemical modification is 1-methylpseudouridine.

99. The method of any one of the preceding paragraphs, wherein the lipid nanoparticle comprises a PEG-modified lipid, a non-cationic lipid, a sterol, an ionizable cationic lipid, or any combination thereof.

100. The method of any one of the preceding paragraphs, wherein the lipid nanoparticle comprises 0.5-15% PEG-modified lipid; 5-25% non-cationic lipid; 25-55% sterol; and 20-60% ionizable cationic lipid.

101. The method of any one of the preceding paragraphs, wherein the PEG-modified lipid is 1,2 dimyristoyl-sn-glycerol, methoxypolyethyleneglycol (PEG2000 DMG), the non-cationic lipid is 1,2 distearoyl-sn-glycero-3-phosphocholine (DSPC), the sterol is cholesterol; and the ionizable cationic lipid has the structure of Compound 1.

Examples

Example 1: Multi-Clade mRNA Immunizations Spur Cross Clade Immune Response

Fifteen Rhesus macaques were divided into Groups ("GR"). Two groups (GRs. 3 and 4) received seven doses of immunizations containing mRNA encoding an HIV-1 envelope protein, with either a Native or Modified CD4 receptor-binding ability, co-formulated with mRNA encoding an SIV group-specific antigen (Gag) protein (Table 1). The other two groups (GRs. 1 and 2) received five doses of the same formula and two doses of pre-made soluble HIV-1 Env protein (SOSIP trimer) administered with an adjuvant (Adjuplex). The immunizations were delivered approximately every eight weeks (FIG. 2), intramuscularly carried by the lipid nanoparticle comprising an ionizable cationic lipid of Compound 1.

Figure 2:
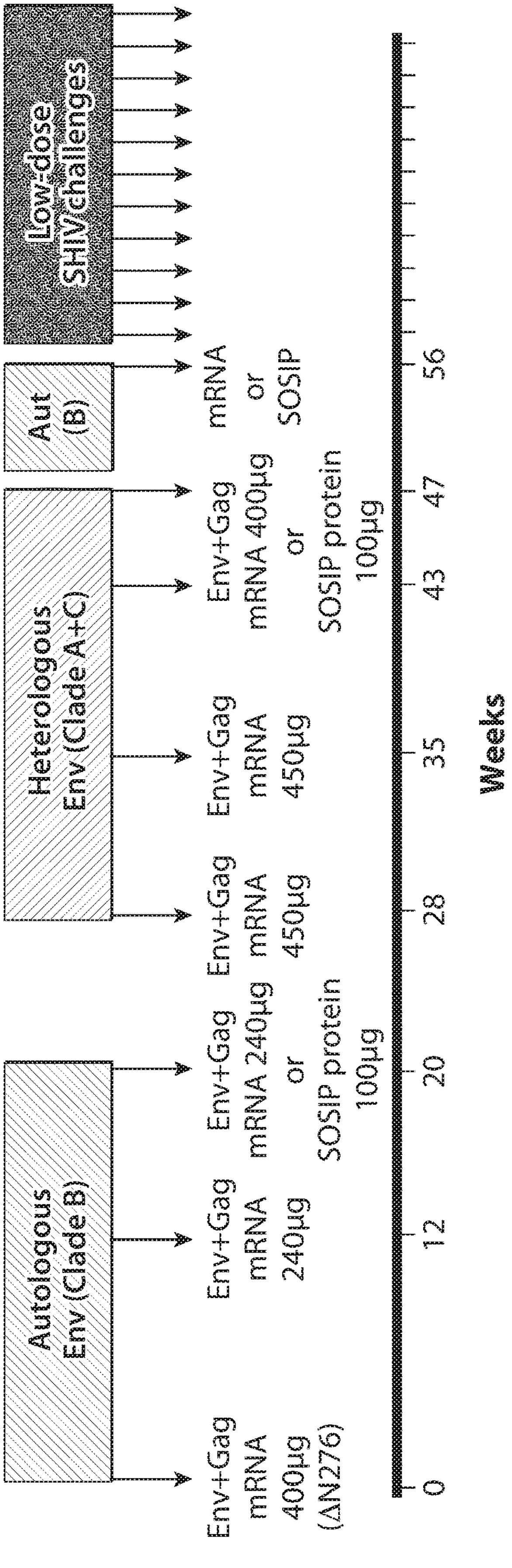
FIG. 2 shows the study plan with associated vaccination doses, components, Clades, and timelines.

The first two doses contained mRNA encoding an Env protein from Clade B. These were followed by either a third dose of the same formula (GRs. 3 and 4) or a dose of the soluble envelope proteins (FIG. 2). Three more doses of mRNA encoding proteins from Clades A and C were then administered followed by a either a fourth dose of the same formula (GRs. 3 and 4) or a dose of soluble envelope proteins (FIG. 2). Two additional immunizations of Clade B followed. A single protein boost of soluble envelope protein from Clade B was administered at week 51 and a dose sparing boost of either mRNA encoding an Env or a soluble envelope protein was administered at week 56 (FIG. 2, Table 1).

Figure 3:
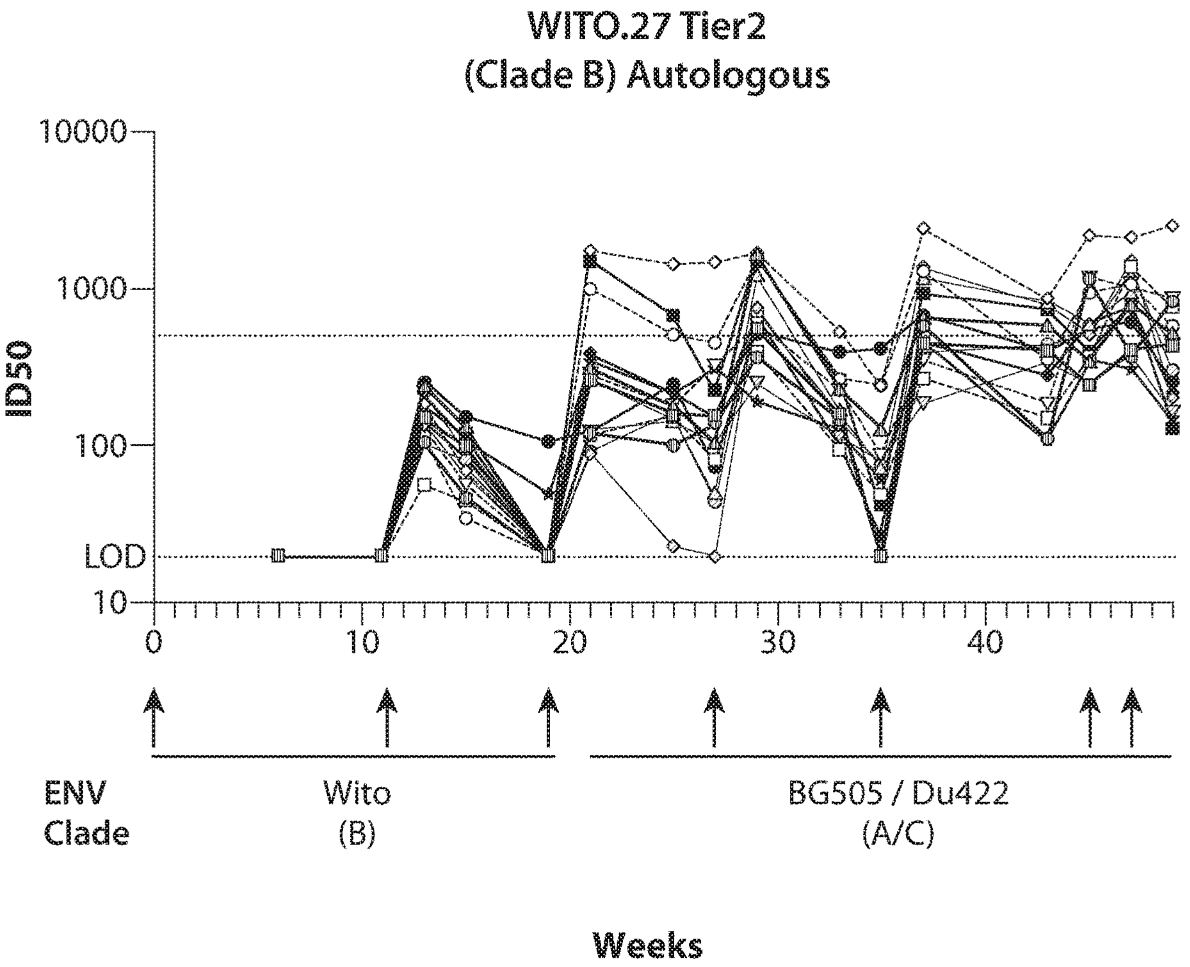
FIG. 3 shows a graph of an autologous titer of WITO.27 tier 2 (Clade B) of Rhesus macaques. The median inhibitory dose ("$ID_{50}$") is plotted on the y-axis against time displayed in weeks on the x-axis. The vaccination doses and respective Clade information are also indicated below the x-axis to indicate the timing and identity of the vaccination doses.
Figure 4:
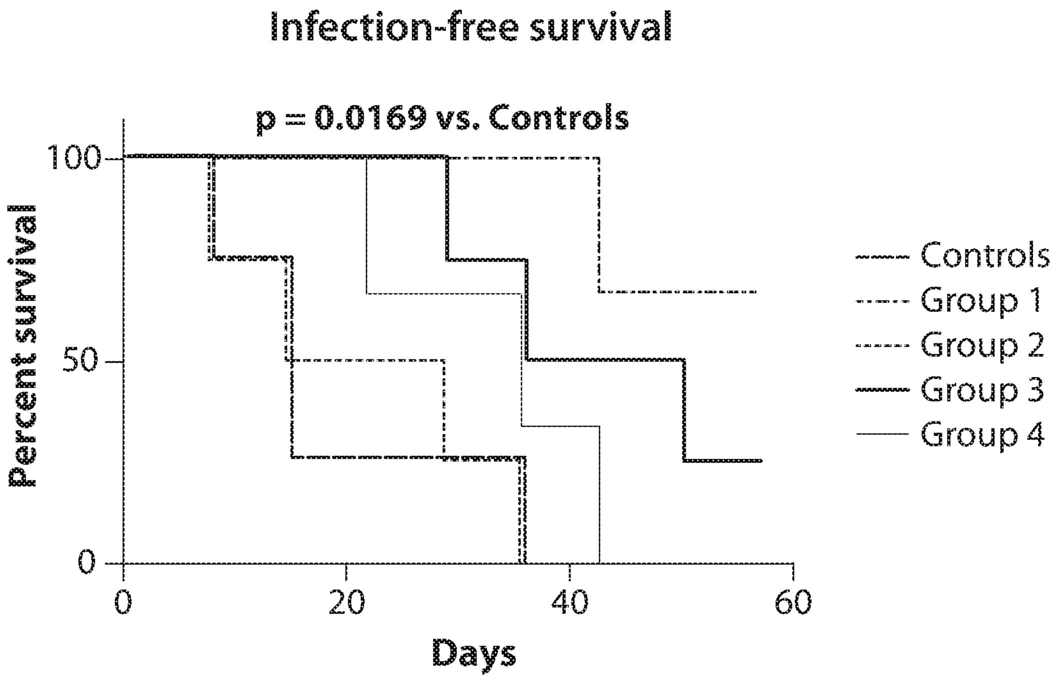
FIG. 4 shows the infection-free survival out to day 56 of dosed Rhesus macaques from Example 1 (contained herein below) after repeated low-dose intra-rectal inoculation of tier-2 heterologous SHIV virus (AD8). The percent survival is represented on the y-axis with the time elapsed in days on the x-axis.
Figure 5:
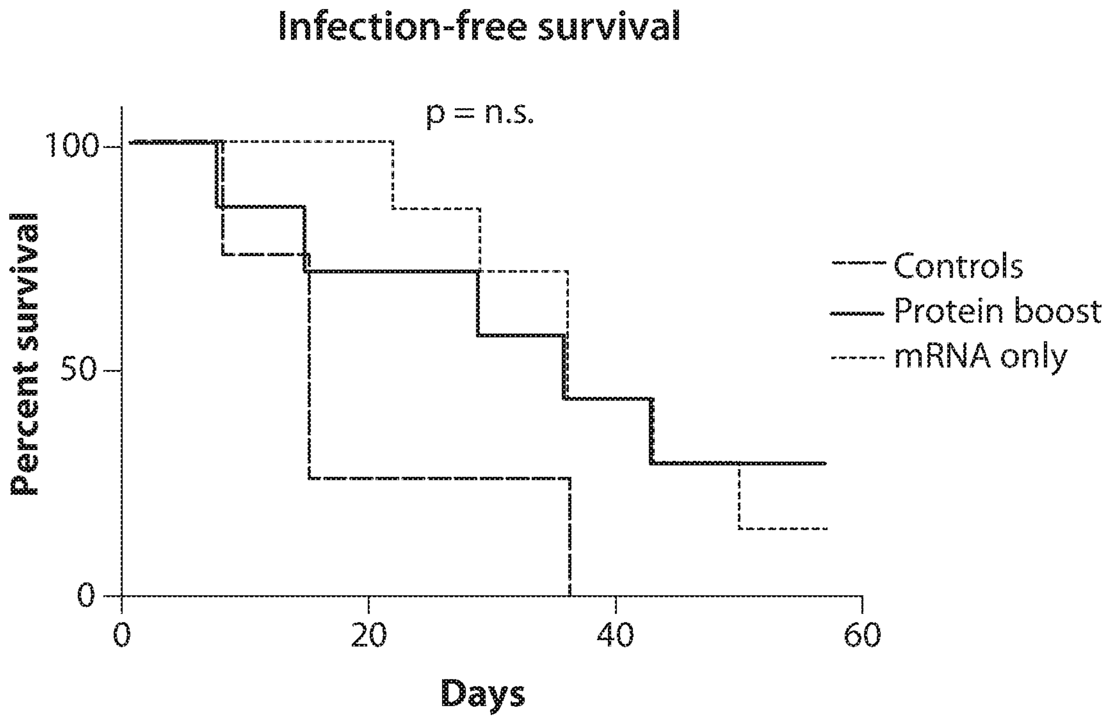
FIG. 5 shows the infection-free survival out to day 56 of dosed Rhesus macaques from Example 1 (contained herein below) after repeated low-dose intra-rectal inoculation of tier-2 heterologous SHIV virus (AD8). The percent survival is represented on the y-axis with the time elapsed in days on the x-axis.

Blood draws were taken and neutralization titers were performed against autologous HIV-1 strains starting at week 13 (after the second dose) as well as a broad-spectrum neutralization of heterologous HIV-1 strains at week 58 (Tables 2 and 3). As Table 2 shows, there is an increasing immunological response to the strain from Clade B, which response persists and increases beyond the administration of the doses containing the strain. This can also be seen in FIG. 3, where the $ID_{50}$ increases over time with respect to autologous HIV-1. Moreover, as Table 3 shows, the immunizations confer an immunological response against not only the strains administered, but against a global panel of strains, including strains from Clades outside of the immunization group. Finally, vaccinated macaques were challenged with live tier-2 heterologous virus (SHIV AD8) by repeated low-dose inoculations at weekly intervals (Table 4). An additional group of four naïve macaques were also infected as controls. Immunized animals showed a partial resistance to infection as they remained uninfected or showed a delayed infection relative to the control group (FIG. 4). Protection for animals who received mRNA followed by protein boosts (GRs. 1 and 2) did not statistically differ from protection observed in animals who received only mRNA (Grs. 3 and 4, FIGS. 4 and 5; p=ns)

TABLE 1

Study groups with immunization compositions

| | G<br>R | n | Env<br>Form | WITO (B)<br>Wk 0 | <br>Wk 11 | <br>Wk 19 | BG505 (A)/Du422 (C)<br>Wk 27 | <br>Wk 35 | <br>Wk 43 | <br>Wk 47 | JR-FL (B)<br>Wk 51 | WITO (B)<br>Wk 56 |
|---|---|---|---|---|---|---|---|---|---|---|---|---|
| mRNA prime + protein boost | 1 | n = 3 | WT | mRNA 400 ug WITO: Gag | mRNA 240 ug WITO: Gag | Protein 100 ug Soluble SOSIP + Adjv WITO | mRNA 225 ug BG505: Gag 225 ug DU422: Gag | mRNA 225 ug BG505: Gag 225 ug DU422: Gag | mRNA 225 ug BG505: Gag 225 ug DU422: Gag | Protein 200 ug Soluble SOSIP + Adjv DU422 BG505 | Protein 100 ug Soluble SOSIP + Adjv JRFL | Protein 50 ug Soluble SOSIP + Adjv WITO |
| | 2 | n = 4 | DS Locked | 400 ug mRNA WITO: Gag | 240 ug mRNA WITO: Gag | | mRNA 225 ug BG505: Gag 225 ug DU422: Gag | mRNA 225 ug BG505: Gag 225 ug DU422: Gag | mRNA 225 ug BG505: Gag 225 ug DU422: Gag | | | |
| mRNA prime + mRNA boost | 3 | n = 4 | WT | 400 ug mRNA WITO: Gag | 240 ug mRNA WITO: Gag | 240 ug mRNA WITO: Gag | mRNA 225 ug BG505: Gag 225 ug DU422: Gag | mRNA 225 ug BG505: Gag 250 ug DU422: Gag | mRNA 225 ug BG505: Gag 225 ug DU422: Gag | 225 ug mRNA BG505: Gag 225 ug mRNA DU422: Gag | Protein 100 ug Soluble SOSIP + Adjv JRFL | 35 ug mRNA WITO: Gag |
| | 4 | n = 4 | DS locked | 400 ug mRNA WITO: Gag | 240 ug mRNA WITO: Gag | | mRNA 225 ug BG505: Gag 225 ug DU422: Gag | mRNA 225 ug BG505: Gag 225 ug DU422: Gag | mRNA 225 ug BG505: Gag 225 ug DU422: Gag | | | |

TABLE 2

Neutralization Titers against the autologous HIV-1 Strain (WITO)

| Group | Animal ID | Week 0<br>WITO | <br>wk. 6 | Week 11<br>WITO<br>wk.11 | <br>wk. 13 | Immunizations:<br>wk. 15 | Week 19<br>WITO<br>wk. 19 | <br>wk. 21 | <br>wk. 25 | Week 27<br>BG + DU<br>wk. 27 | <br>wk. 29 | <br>wk. 33 |
|---|---|---|---|---|---|---|---|---|---|---|---|---|
| 1 | 1D2 | WT | <20 | <20 | 105 | 47 | <20 | 121 | 100 | 137 | 361 | 147 |
| | AZ71 | MRNA + | <20 | <20 | 151 | 101 | <20 | 265 | 162 | 154 | 558 | 160 |
| | BH80 | SOSIP | <20 | <20 | 245 | 134 | <20 | 317 | 179 | 107 | 1695 | 234 |
| 2 | 7G4 | Locked | <20 | <20 | 133 | 57 | <20 | 284 | 180 | 327 | 601 | 226 |
| | 8L4 | MRNA + | <20 | <20 | 188 | 70 | <20 | 1758 | 1442 | 1491 | 1705 | 537 |
| | AZ2S | SOSIP | <20 | <20 | 113 | 35 | <20 | 1017 | 509 | 457 | 1572 | 265 |
| | 37216 | | <20 | <20 | 57 | 45 | <20 | 118 | 156 | 82 | 398 | 95 |
| 3 | AZ97 | | <20 | <20 | 105 | 78 | <20 | 265 | 146 | 50 | 1227 | 169 |
| | BO23 | WT | <20 | <20 | 214 | 91 | <20 | 122 | 145 | 103 | 249 | 113 |
| | 37462 | mRNA | <20 | <20 | 134 | 65 | <20 | 90 | 23 | <20 | 753 | 140 |
| | 38730 | | <20 | <20 | 104 | 79 | <20 | 92 | 160 | 44 | 706 | 142 |
| 4 | AV55 | | <20 | <20 | 207 | 106 | 50 | 349 | 215 | 309 | 192 | 126 |
| | BA07 | Locked | <20 | <20 | 172 | 120 | <20 | 1523 | 677 | 226 | 1515 | 259 |
| | BV94 | MRNA | <20 | <20 | 145 | 78 | <20 | 385 | 220 | 152 | 667 | 105 |
| | 39267 | | <20 | <20 | 255 | 153 | 107 | 122 | 248 | 74 | 519 | 397 |

| Group | Animal ID | Week 35<br>BG + DU<br>wk. 35 | <br>wk. 37 | Week 43<br>BG + DU<br>wk. 43 | <br>wk. 45 | Week 47<br>Immunizations:<br>BG + DU<br>wk. 47 | <br>wk. 49 | Week 51<br>BG + DU<br>wk. 51 | <br>wk. 53 | Week 56<br>WITO<br>wk. 56 | <br>wk. 58 |
|---|---|---|---|---|---|---|---|---|---|---|---|
| 1 | 1D2 | <20 | 585 | 112 | 1148 | 371 | 837 | 730 | 623 | 214 | 489 |
| | AZ71 | <20 | 447 | 403 | 245 | 409 | 438 | 369 | 433 | 176 | 798 |
| | BH80 | 130 | 664 | 584 | 347 | 803 | 516 | 515 | 319 | 153 | 593 |

TABLE 2-continued

Neutralization Titers against the autologous HIV-1 Strain (WITO)

| | | | | | | | | | | | |
|---|---|---|---|---|---|---|---|---|---|---|---|
| 2 | 7G4 | 87 | 349 | 184 | 1189 | 1081 | 879 | 1411 | 644 | 387 | 480 |
| | 8L4 | 239 | 2439 | 865 | 2207 | 2126 | 2554 | 2026 | 1587 | 1164 | 2497 |
| | AZ2S | 245 | 1302 | 357 | 965 | 1078 | 578 | 410 | 417 | 198 | 1190 |
| | 37216 | 49 | 271 | 150 | 369 | 1389 | 769 | 1193 | 949 | 277 | 2144 |
| 3 | AZ97 | 74 | 1188 | 828 | 598 | 960 | 440 | 443 | 882 | 707 | 1216 |
| | BO23 | 82 | 186 | 338 | 247 | 373 | 164 | 290 | 432 | 291 | 603 |
| | 37462 | <20 | 1390 | 774 | 504 | 1504 | 202 | 555 | 645 | 173 | 530 |
| | 38730 | 76 | 388 | 439 | 521 | 1327 | 303 | 593 | 793 | 254 | 836 |
| 4 | AV55 | 60 | 454 | 109 | 353 | 309 | 149 | 231 | 425 | 137 | 362 |
| | BA07 | 42 | 929 | 749 | 398 | 836 | 130 | 278 | 406 | 244 | 564 |
| | BV94 | 27 | 462 | 282 | 593 | 766 | 220 | 304 | 1737 | 504 | 634 |
| | 39267 | 419 | 670 | 411 | 551 | 616 | 257 | 489 | 274 | 172 | 482 |

TABLE 3

Broad-Spectrum Neutralization of Heterologous Tier-2 HIV-1 Strains

| | | | Strain: | | | | | | | |
|---|---|---|---|---|---|---|---|---|---|---|
| | | | JRFL | WITO.33 | BG505 | AD8 | 398F1 | 246F3 | CNE8 | CNE55 |
| | | | Clade: | | | | | | | |
| PL No. | Group | Animal ID | B wk. 58 | B wk. 58 | A wk. 58 | B wk. 58 | A wk. 58 | AC wk. 58 | AE wk. 58 | AE wk. 58 |
| 1 | 1 | 1D2 | 44 | 9 | 18 | 8 | 89 | 44 | 35 | <10 |
| 6 | 1 | AZ71 | 40 | 11 | 9 | 33 | 63 | 20 | 24 | <10 |
| 9 | 1 | BH80 | 52 | 34 | 18 | 44 | 114 | 62 | 51 | <10 |
| 2 | 1 | 7G4 | 60 | 14 | 24 | 33 | 40 | 36 | 36 | <10 |
| 3 | 1 | 8L4 | 84 | 68 | 39 | 36 | 48 | 24 | 21 | <10 |
| 5 | 1 | AZ25 | 68 | 32 | 28 | 34 | 79 | 23 | 38 | <10 |
| 12 | 2 | 37216 | 64 | 20 | 20 | 86 | 74 | 60 | 41 | 17 |
| 7 | 1 | AZ97 | 48 | 28 | 35 | 84 | 126 | 56 | 44 | <10 |
| 10 | 1 | BO23 | 48 | 21 | 220 | 46 | 44 | 38 | 36 | <10 |
| 13 | 1 | 37462 | 58 | 8 | 8 | 47 | 77 | 37 | 44 | 13 |
| 14 | 3 | 38730 | 32 | 20 | 27 | 32 | 79 | 39 | 41 | <10 |
| 4 | 4 | AV55 | 80 | 36 | 16 | 84 | 61 | 28 | 41 | <10 |
| 8 | 4 | BA07 | 43 | 26 | 52 | 50 | 36 | 14 | 35 | <10 |
| 11 | 4 | BV94 | 40 | 24 | 28 | 40 | 59 | 47 | 59 | <10 |
| 15 | 4 | 39267 | 64 | 31 | 70 | 42 | 175 | 72 | 50 | 16 |

| | | | Strain: | | | | | | | |
|---|---|---|---|---|---|---|---|---|---|---|
| | | | TRO1I | X2278 | BJOXO | CH119 | 25710 | CE1176 | CE0217 | X1632 |
| | | | Clade: | | | | | | | |
| PL No. | Group | Animal ID | B wk. 58 | B wk. 58 | BC wk. 58 | BC wk. 58 | C wk. 58 | C wk. 58 | C wk. 58 | G wk. 58 |
| 1 | 1 | 1D2 | 36 | 42 | <10 | 33 | 35 | 31 | 15 | 16 |
| 6 | 1 | AZ71 | 46 | 38 | 20 | 20 | 31 | 22 | 12 | 9 |
| 9 | 1 | BH80 | 75 | 188 | 37 | 37 | 35 | 27 | 20 | 40 |
| 2 | 1 | 7G4 | 78 | <10 | <10 | 32 | 35 | 26 | 12 | <10 |
| 3 | 1 | 8L4 | 54 | 88 | 20 | 29 | 47 | 26 | 37 | 40 |
| 5 | 1 | AZ25 | 64 | <10 | <10 | 33 | 33 | 20 | 14 | 8 |
| 12 | 2 | 37216 | 61 | 112 | 56 | 56 | 53 | 34 | 36 | 20 |
| 7 | 1 | AZ97 | 80 | 44 | 40 | 43 | 61 | 29 | 20 | 12 |
| 10 | 1 | BO23 | 32 | <10 | 37 | 30 | 32 | 21 | 18 | 14 |
| 13 | 1 | 37462 | 48 | 80 | 76 | 56 | 46 | 33 | 75 | 42 |
| 14 | 3 | 38730 | 47 | 40 | 18 | 53 | 60 | 28 | 20 | 9 |
| 4 | 4 | AV55 | 80 | 28 | 21 | 41 | 45 | 35 | 40 | 68 |
| 8 | 4 | BA07 | 50 | 194 | 20 | 26 | 26 | 13 | 23 | <10 |
| 11 | 4 | BV94 | 58 | 160 | 28 | 35 | 33 | 32 | 29 | 17 |
| 15 | 4 | 39267 | 55 | 75 | 24 | 58 | 63 | 50 | 54 | 18 |

Materials and Methods

Monkeys

Fifteen female Rhesus macaques (*Macaca* mulatta), aged 6 to 12, were maintained in accordance with the guidelines of the Committee on Care and Use of Laboratory Animals (which is incorporated herein by reference) and housed in a biosafety level 2 facility at BIOQUAL, Inc. (Rockville, MD). The animals were grouped by carefully balancing age, weight, and complete blood count (CBC)/chemistry parameters. Four additional naïve macaques were included in the study during the challenge phase. All animals were negative for the major histocompatibility complex (MHC) class I Mamu-A*01 allele.

Proteins

Soluble stabilized envelope proteins (SOSIP trimers) were produced in 293 Freestyle cells by transient co-transfection of plasmids encoding Env DNA and the cellular protease Furin. Cell culture supernatants were harvested 5 or 6 days after transfection. After 0.22 um filtering, the supernatants were sequentially loaded on a *Galanthus nivalis* lectin column, followed by passage on a size-exclusion column and then on a mAb 446-52D negative selection column. Finally, the purified trimers were concentrated to 1-2 mg/ml in PBS and stored at −80° C. Site-directed mutagenesis was performed to introduce specific mutations. The N188 glycan was introduced in Clade B WITO.33 and WITO.33 113C-432GCG SOSIP. Other SOSIP proteins included BG505 (Clade A) containing the following mutations: T332N, 241N, 289N, 375Y or BG505 T332N, 241N, 289N, 375Y, D113C-R429C; JR-FL (Clade B) containing the following mutations: 375Y and JR-FL, D113C-R432GCG 375Y; and DU422 (Clade C) containing the following mutations: 295N, 386N, 375Y and Du422 295N, 386N, 375Y, 113C-432GCG.

mRNA Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

mRNA Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Viruses

In vivo-titrated $SHIV_{AD8\text{-}EO}$ virus stocks were provided by Dr. Malcolm A. Martin (LMM, NIAID). Virus stocks were prepared by transfecting 293T cells with SHIV AD8-CK15 molecular clones using Lipofectamine 2000. Culture supernatants were collected 48 hours later. The virus stock infectivity was measured by infecting Con A-stimulated rhesus PBMCs and aliquots were stored at −80° C. until use.

For in vitro neutralization assays, HIV-1 pseudoparticles expressing wide-type or mutated gp160 from BG505 and other isolates were produced in HEK 293T cells by co-transfecting Env-expressing plasmids with a backbone plasmid, $pSG3^{\Delta env}$, expressing a full-length HIV-1 clone with a defective env gene using Mirus293 Transfection Reagent. Culture supernatants were collected 48 hours later and aliquots were stored at −80° C. until use; virus stock infectivity titers were measured by using serial dilutions in TZM-b1 cells.

Experimental Replication, Randomization, and Blinding

For vaccination, 15 macaques were allocated to experimental groups in order to balance the average age, weight and peripheral WBC and CD4+ T-cell counts. Each in vitro experiment was independently performed at least twice in duplicate wells to ensure reproducibility.

Lipid Nanoparticle

An ionizable cationic lipid nanoparticle formulation, comprising a molar ratio of 20-60% ionizable cationic lipid (Compound 1), 5-25% non-cationic lipid, 25-55% sterol, and 0.5-15% PEG-modified lipid, was used for these experiments.

Dosing

All macaque immunizations were performed at BIOQUAL, Inc facility. All 15 macaques were immunized with 500 µl of the dosing material via the intramuscular route into the right posterior thigh of each animal. Injections included 500 µl of co-formulated Env+Gag mRNAs, or SOSIP.664 trimers (wild-type or interdomain-stabilized) pre-mixed with 100 µL of Adjuplex adjuvant (Sigma). Immunizations were performed at weeks 0, 11, 19, 27, 35, 43, 47, 51, 56, and 59.

Blood Draws

Animals were sedated and blood was drawn from a posterior leg vein generally at 2 weeks after each immunization, as well as every week during the virus challenge phase. Plasma and PBMC were collected and stored frozen. An aliquot of blood was regularly sent to an external laboratory for blood chemistry and CBC counts.

Virus Challenge

The $SHIV_{AD8-EO}$ is a CCR5-tropic tier 2 (neutralization-sensitivity phenotype) pathogenic strain that replicates to high levels in rhesus macaques. The virus stock was titrated in macaque PBMC and diluted in PBS to 10 $TCID_{50}$ at the time of challenge. All animals were inoculated intra-rectally with low-dose (10 tissue culture infectious doses per dose) $SHIV_{AD8-EO}$ at weekly intervals until infection became established. A 3 ml speculum was used to gently open the rectum, and a 1-ml suspension of virus in a tuberculin syringe was slowly infused into the rectal cavity.

Titers

Macaque plasma samples were collected from two weeks post-immunization and other interested time points (e.g., plasma samples were collected at weeks-2, 7, 19, 27, 31, 35, 43, 47, 53, and 60). The neutralization was performed by using single-cycle infection of TZM-b1 cells by ENV pseudoviruses. Serial dilutions of plasma samples were incubated with pseduotyped viruses for 30 minutes in 96 well plates and then 100 µl TZM-B1 cells that contain 10,000 cells were added. Reporter gene activation signal was detected at 48 hours later after removing 150 µl media and adding the 40 µl Luciferase Assay Reagent per well. Relative Light Unit were recorded and half-maximal inhibitory concentrations ($IC_{50}$) were performed using Graphpad Prism 7.

Example 2

Figure 6:
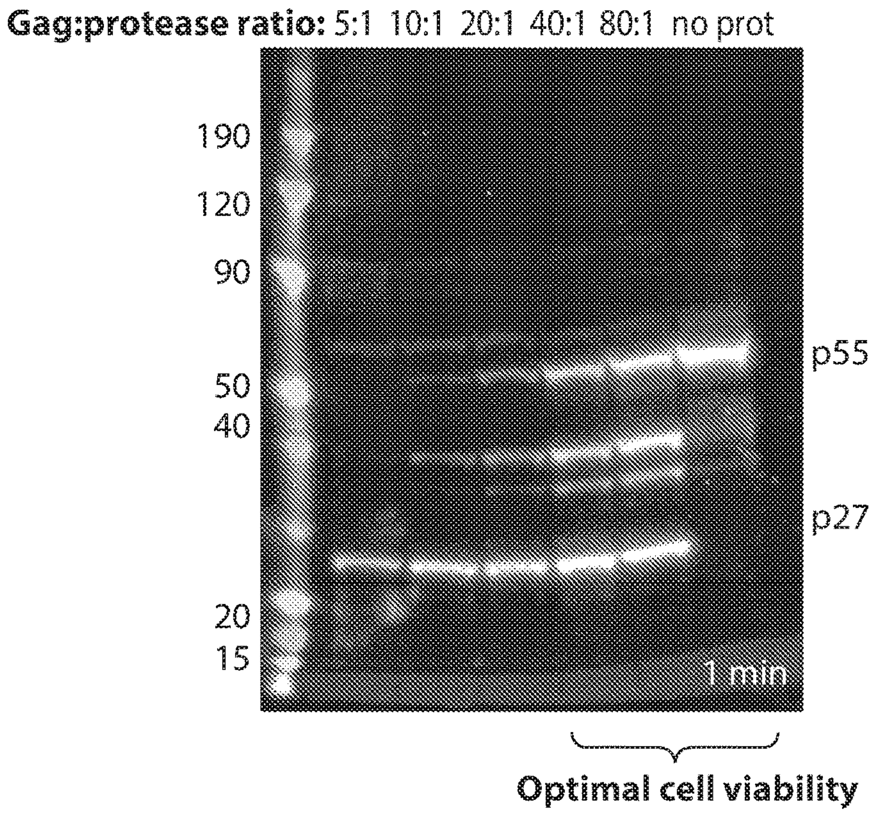
FIG. 6 shows that the SIV Gag polyprotein is efficiently processed to its final products, including the main core protein p27, in the presence of SIV protease.

The data in this set of experiments shows that the SIV Gag polyprotein is efficiently processed to its final products, including the main core protein p27, in the presence of SIV protease (FIG. 6). The image in FIG. 6 shows a Western blot analysis of cell lysates obtained from 293-T human embryonic kidney cells stably transduced to express HIV-1 WITO.153E Env using a retroviral vector. The cells were transfected with SIV Gag mRNA and SIV protease mRNA at different ratios (5:1, 10:1, 20:1, 40:1 and 80:1). The cells were harvested 48 hours later, lysed and analyzed by WB. Increasing levels of fully processed Gag p27 were detected using serial dilutions of protease with optimal balance between yield, processing and cell viability between 40:1 and 80:1 ratios. The presence of bands corresponding to incompletely processed or unprocessed Gag is expected in whole cell lysate because only a fraction of Gag is fully processed at any given time even in the presence of excess protease. The yield of Gag expression is lower at high protease concentrations due to poor cell viability. The WB was revealed using Rabbit anti-SIVp27 polyclonal antiserum at 1:2000 (SP1432-B) as a primary antibody and Donkey-anti-Rabbit antibodies, HRP-conjugated, at 1:5000 (R&D Systems) as a secondary antibody.

Figure 7:
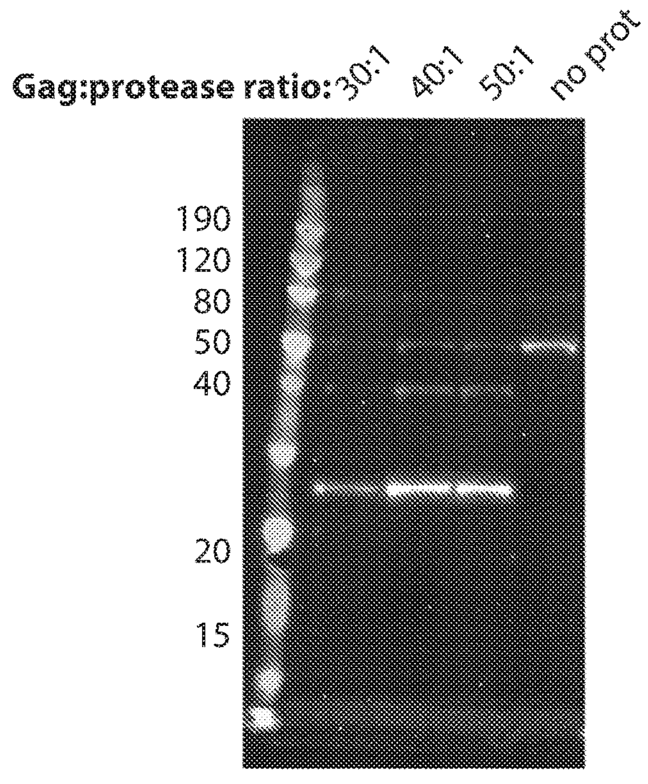
FIG. 7 shows that fully processed SIV core protein p27 is efficiently and selectively incorporated into virus-like particles (VLPs) in the presence of SIV protease.

The data in this set of experiments shows that fully processed SIV core protein p27 is efficiently and selectively incorporated into virus-like particles (VLPs) in the presence of SIV protease (FIG. 7). The image in FIG. 7 shows a Western blot analysis of concentrated SHIV VLPs produced by 293-T human embryonic kidney cells stably transduced with HIV-1 WITO.153E Env and transfected with SIV Gag mRNA and SIV protease mRNA at different ratios (30:1, 40:1, 50:1). The culture supernatants were harvested 48 hours later, ultracentrifuged on a sucrose cushion to concentrate VLPs, and the pellets were analyzed by WB. Purified VLPs contain almost exclusively fully processed Gag. The WB was revealed using Rabbit anti-SIVp27 polyclonal antiserum at 1:2000 (SP1432-B) as a primary antibody and Donkey-anti-Rabbit antibodies, HRP-conjugated, at 1:5000 (R&D Systems) as a secondary antibody.

Figure 8:
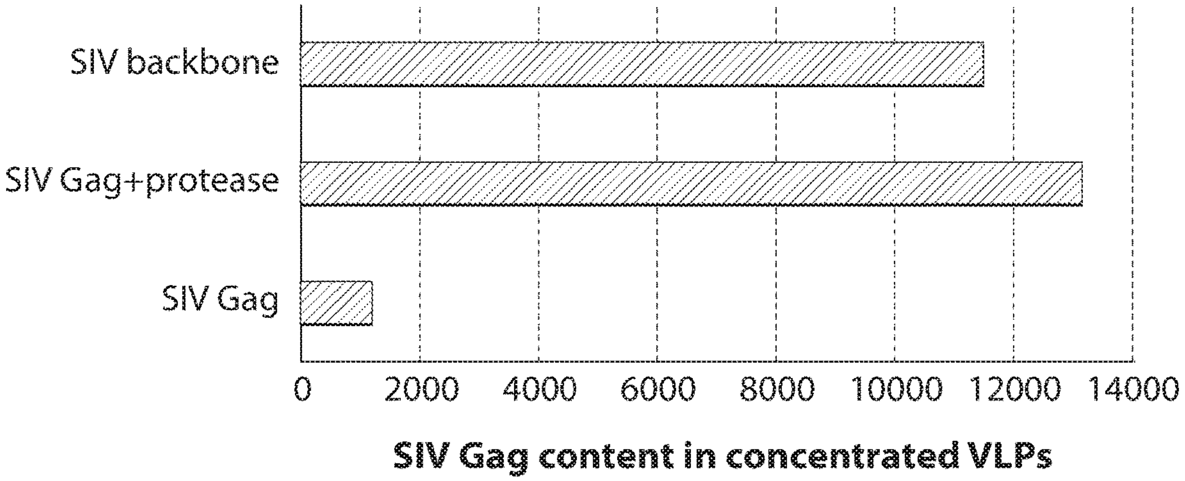
FIG. 8 shows that the production of extracellular SHIV VLPs is markedly increased in the presence of SIV protease.

The data in this set of experiments shows that the production of extracellular SHIV VLPs is markedly increased in the presence of SIV protease (FIG. 8). The chart in FIG. 8 shows the results of quantitative ELISA measurements in concentrated VLPs obtained from 293-T cells stably expressing HIV-1 WITO.153E Env transfected with DNA plasmids expressing either SIV Gag alone, SIV-Gag+SIV protease or SIV full-length backbone (Env-deleted but containing protease). Culture supernatants were harvested 48 hours later, ultracentrifuged on a sucrose cushion to concentrate VLPs, and the pellets were analyzed by ELISA for SIV Gag p27 content.

Figure 9A:
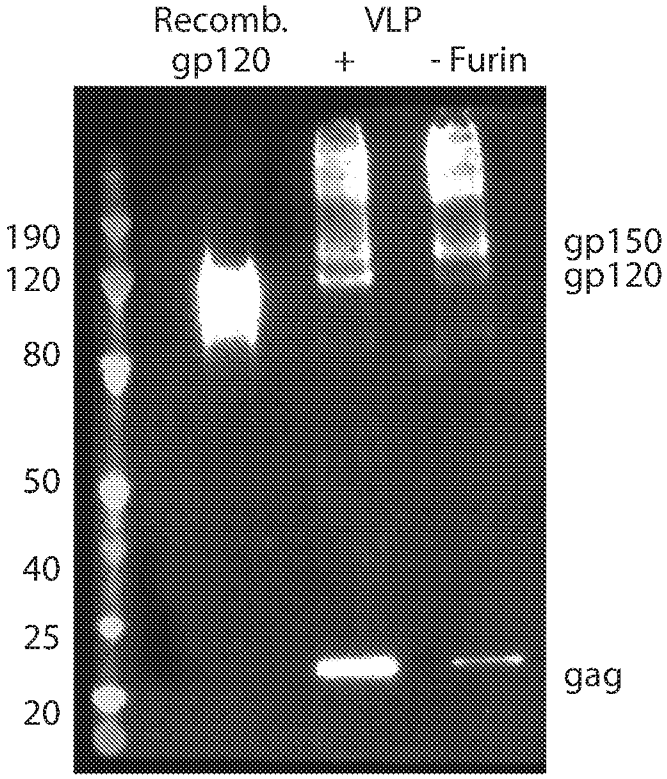
FIGS. 9A-9B show that the efficiency of Env processing to gp120 (FIG. 9A) and the production of extracellular VLPs (FIG. 9B) are markedly increased in the presence of furin.
Figure 9B:
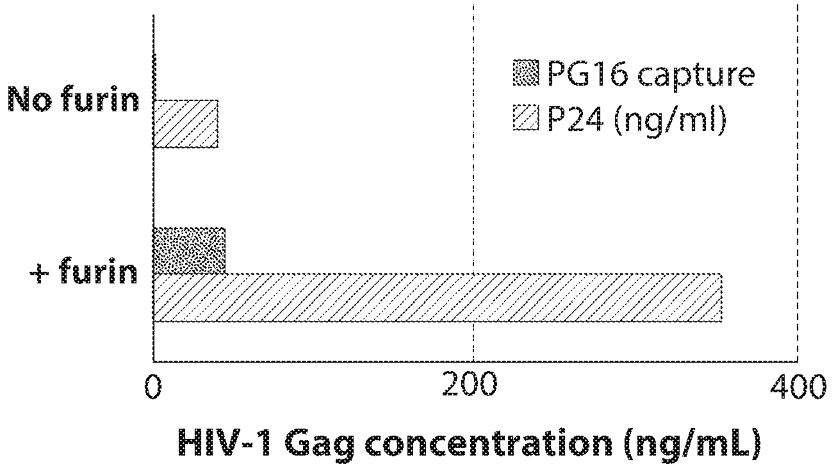

The data in this set of experiments shows that the efficiency of Env processing to gp120 (FIG. 9A) and the production of extracellular VLPs (FIG. 9B) are markedly increased in the presence of furin. FIG. 9A includes a Western blot showing the increased processing of the Env precursor gp150 to gp120 in the presence of furin. 293T cells were transfected with HIV-1 Env DNA and HIV Gag-Pol DNA with or without furin DNA. Culture supernatants were harvested 48 hours later, ultracentrifuged to concentrate VLPs, and pellets were lysed and analyzed by WB. The WB was revealed using Rabbit anti-HIV-1 Env polyclonal antibody at 1:200 (home made) as a primary antibody and Donkey-anti-Rabbit antibodies, HRP-conjugated, at 1:5000 (R&D Systems) as a secondary antibody. FIG. 9B includes a chart showing the results of quantitative ELISA measurements in concentrated VLPs obtained from 293T cells transfected with HIV-1 Env DNA and HIV Gag-Pol DNA with or without furin DNA. Culture supernatants were harvested 48 hours later and tested for total p24 content (green bars) or used for virion capture using mAb PG16 immobilized on magnetic beads (red bars). Captured virions were lysed and analyzed by ELISA for p24 content. The efficiency of PG16-mediated capture is typically low (between 10% and 20% of the total p24 content) even on infectious viral stocks, presumably due to the low density of Env on the virion surface and/or epitope masking by serum proteins.

Figure 10:
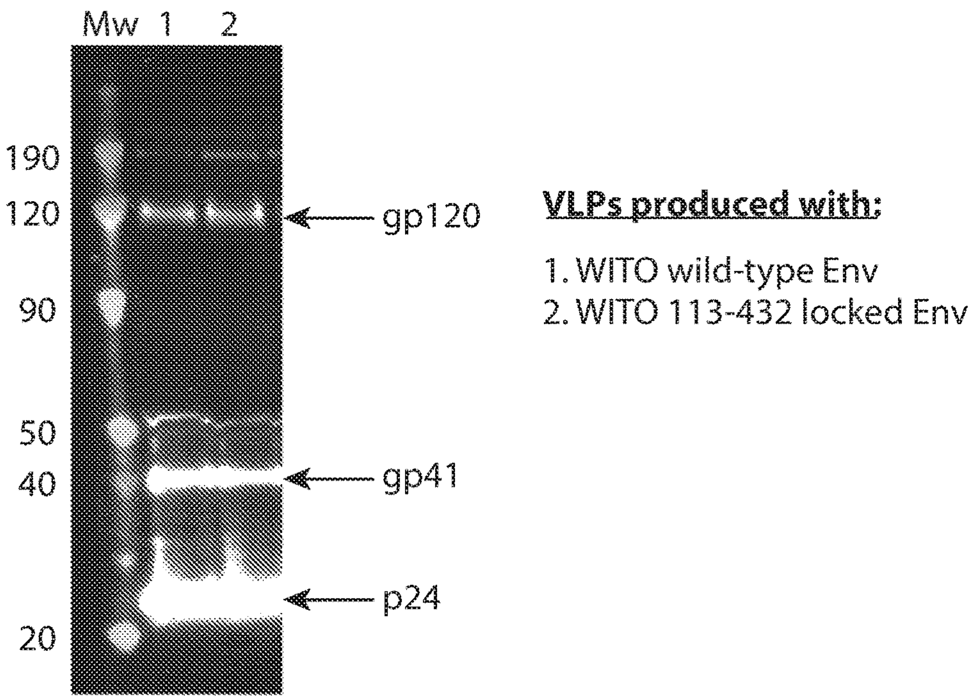
FIG. 10 shows that both HIV-1 Env and Gag are fully processed in virus-like particles (VLPs) produced using Gag-Pol (which expresses also the viral protease).

The data in this set of experiments shows that both HIV-1 Env and Gag are fully processed in virus-like particles (VLPs) produced using Gag-Pol (which expresses also the viral protease) (FIG. 10). The image in FIG. 10 shows a Western blot analysis of concentrated HIV-1 VLPs produced by 293-T human embryonic kidney cells stably transduced with HIV-1 WITO.153E wild-type or interdomain-locked (113-432) Env and transfected with HIV-1 Gag-Pol plasmid. The culture supernatants were harvested 48 hours later and VLPs were purified using magnetic beads coated with anti-Env mAb PG16. This selection enriches for VLPs with high Env content. Antibody-captured VLPs were then lysed and analyzed by WB using a polyclonal human HIV-positive serum as a primary antibody and human IgG antibodies, HRP-conjugated, as a secondary antibody.

Figure 11:
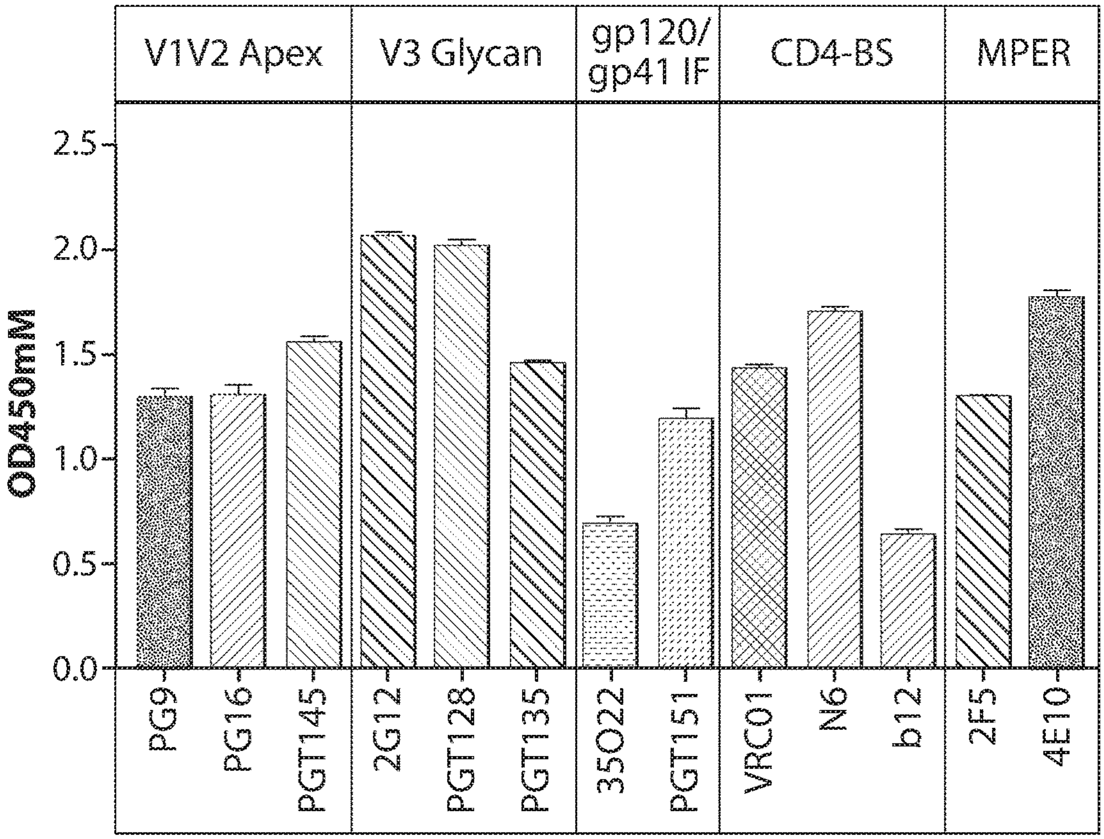
FIG. 11 shows that VLPs produced using Gag-Pol display a desired vaccine-relevant antigenic profile, with high expression of epitopes recognized by broadly neutralizing antibodies (bNAbs).
Figure 12:
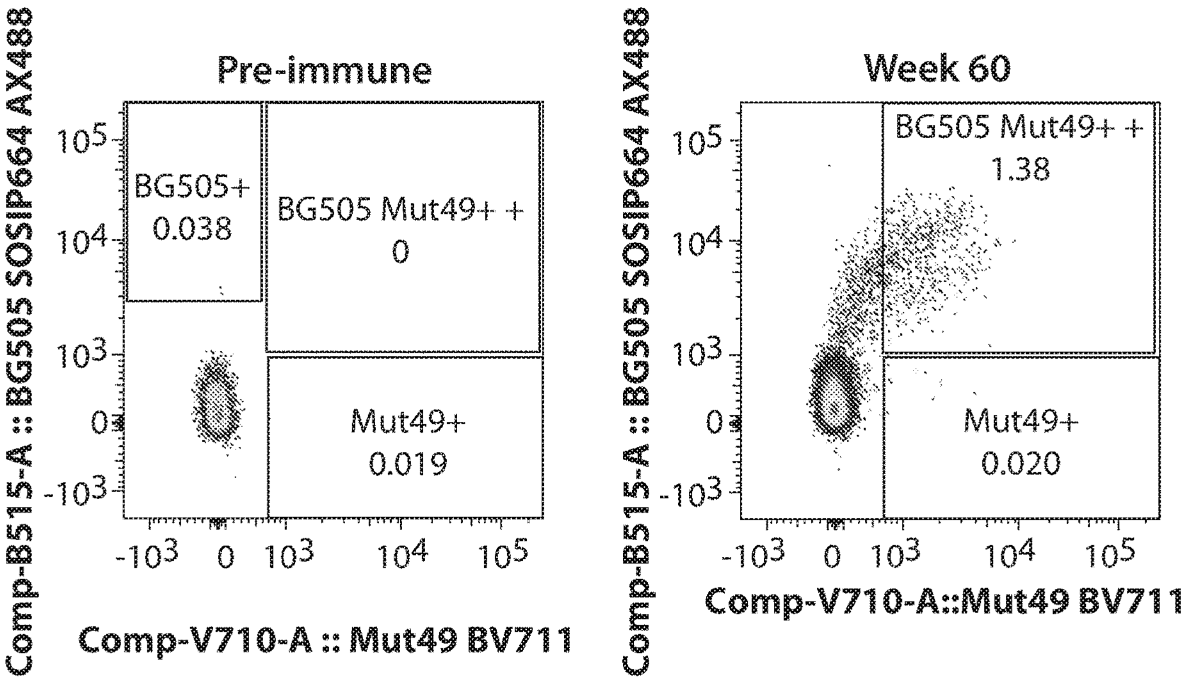
FIG. 12 shows detection and sorting of single B cells producing antibodies to the CD4-binding site from the peripheral blood of a representative macaque that was completely protected from SHIV-AD8 infection. B cells double-positive for labelled BG505 trimer (y-axis) and eODGT8.M49 (x-axis) probes were individually sorted by FACS. Antibody cloning and expression of paired heavy and light chains are in progress.
Figure 13:
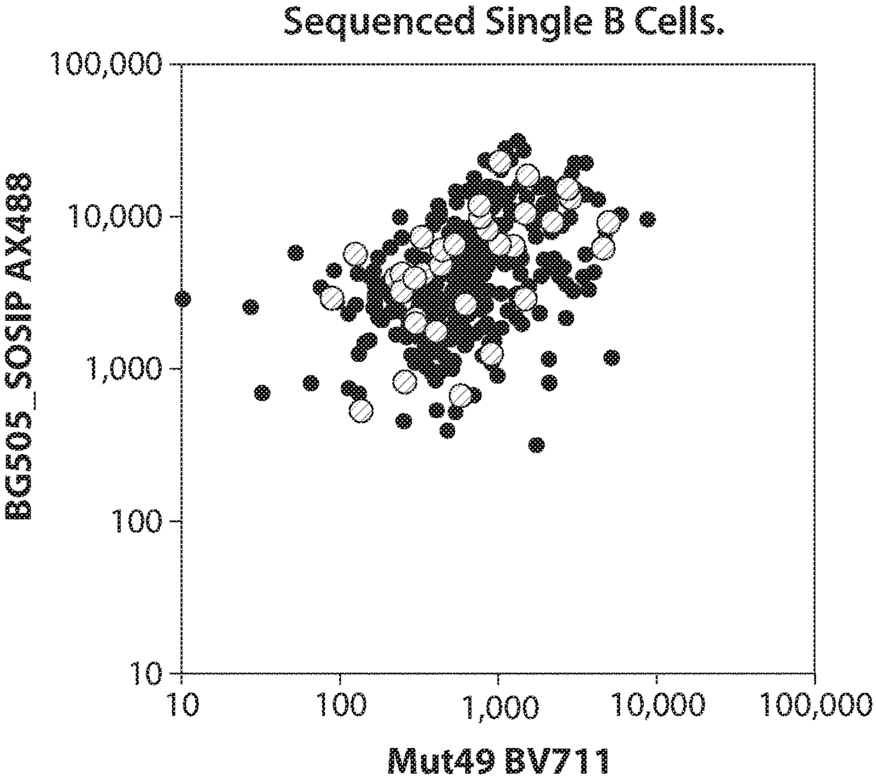
FIG. 13 shows FACS-sorted CD4-BS-specific B cells from which productive antibodies were cloned.
Figure 14:
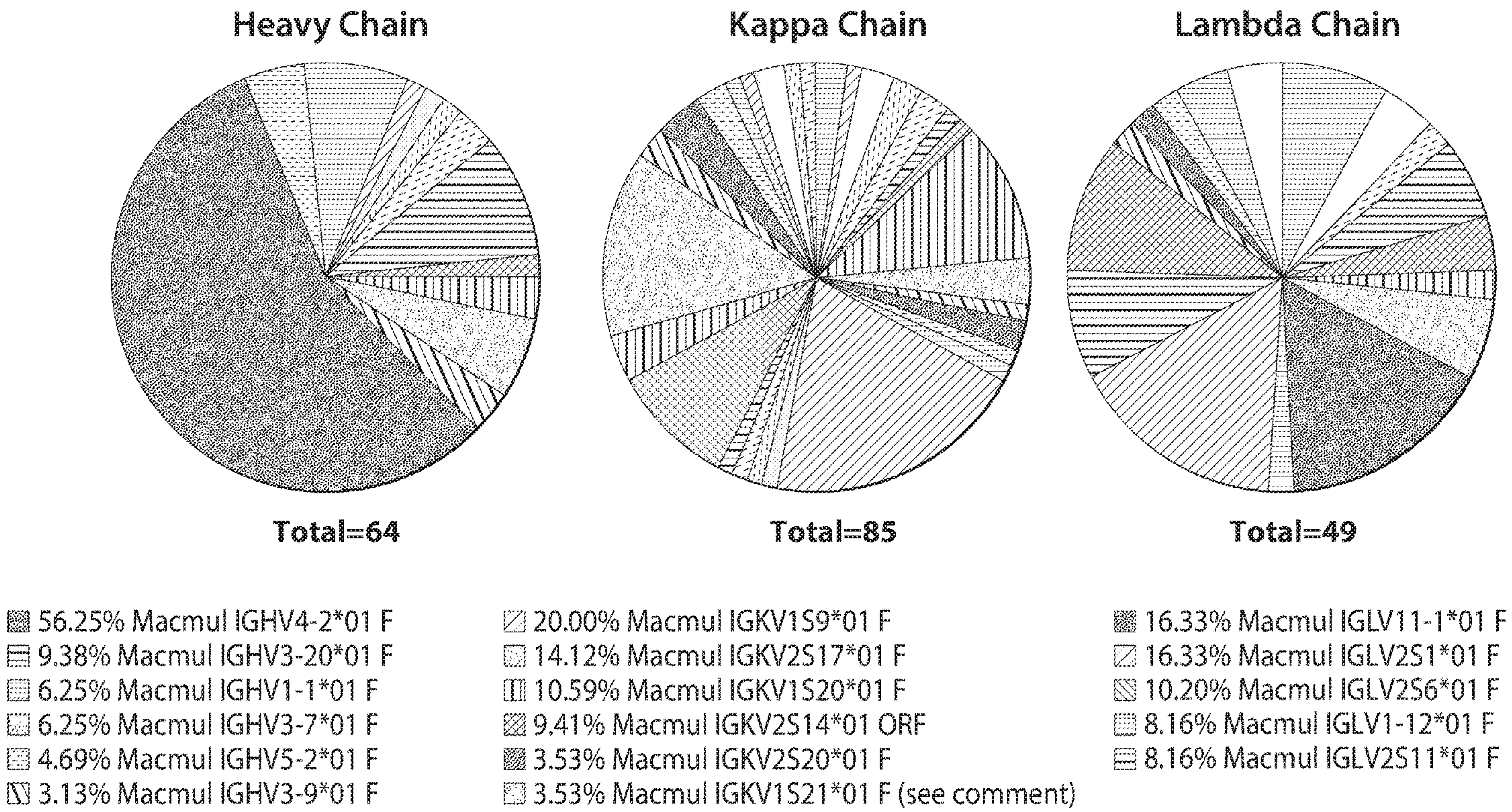
FIG. 14 shows prevalence of heavy chain variable gene (VH) usage among CD4-BS-specific B cells from a protected macaque.
Figure 15:
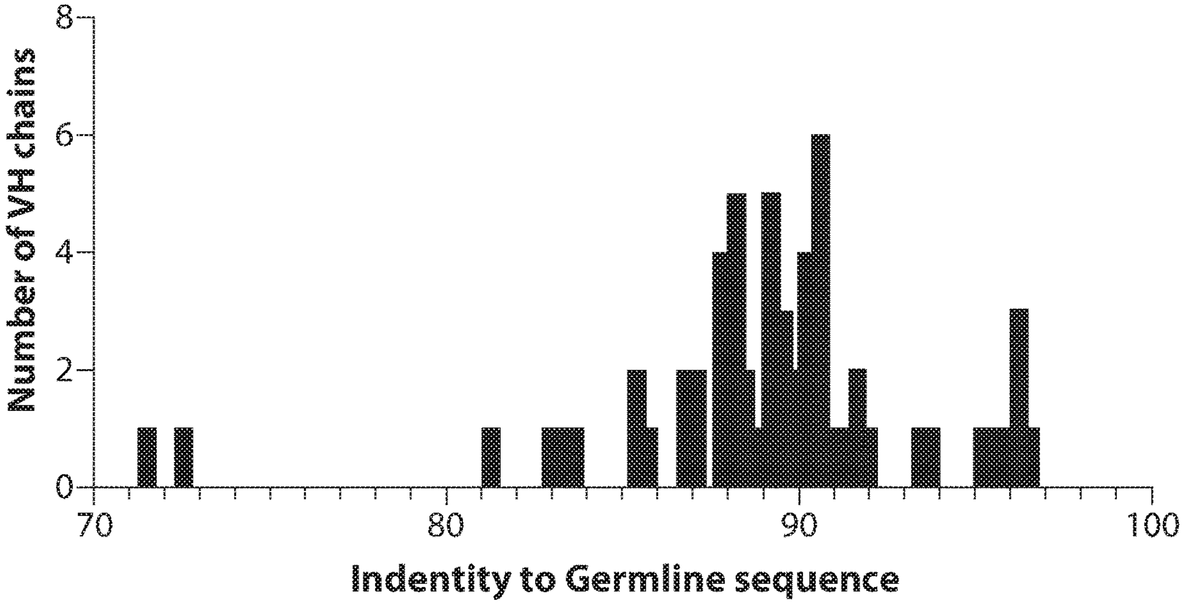
FIG. 15 shows variation from germline sequence in heavy chain variable genes (VH) among CD4-BS-specific B cells.

The data in this set of experiments shows that VLPs produced using Gag-Pol display a desired vaccine-relevant antigenic profile, with high expression of epitopes recognized by broadly neutralizing antibodies (bNAbs) (FIG. 11). 293T cells stably expressing HIV-1 WITO.153E Env were transfected with HIV-1 Gag-Pol, which contains the viral protease gene. Culture supernatants were collected at 48 hrs., ultracentrifuged on a sucrose cushion to concentrate VLPs, and washed once with phosphate buffer saline. The expression of epitopes recognized by bNAbs was tested by VLP ELISA: briefly, the pelleted material was captured on ELISA plates using *Galanthus nivalis* lectin; after washing and blocking with 0.05% casein, different human bNAbs were added for 45 min at room temperature, washed and revealed using a goat-anti-human HRP-conjugated secondary antibody. The antigenic supersites recognized by the different groups of bNAbs are indicated at the top. IF=gp120/gp41 interface–CD4-BS=CD4 binding site–MPER=Membrane-proximal extracellular region of gp41.

Example 3

In this example, we cloned a significant number of diverse antibodies specific for the CD4-binding site. A majority of them use VH4, which is the heavy chain used by all but 2 of the anti-CD4-binding site neutralizing antibodies cloned from macaques in another study (Mason et al. *PLOS Pathogen,* 2016, DOI:10.1371/journal.ppat.1005537).

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method of inducing in a subject an immune response to human immunodeficiency virus (HIV), the method comprising:

(a) during a first period of time, administering to a subject an initial dose and multiple autologous boost doses of a first composition comprising a messenger RNA (mRNA) encoding an HIV envelope (Env) protein and an mRNA encoding a lentivirus group-specific antigen (Gag) protein formulated in a lipid nanoparticle;

(b) during a second period of time, administering to the subject multiple heterologous boost doses of a second composition comprising an mRNA encoding an HIV Env protein and an mRNA encoding a lentivirus Gag protein formulated in a lipid nanoparticle; and (c) producing in the subject a broadly neutralizing antibody response against multiple strains of HIV.

2. The method of claim 1, wherein the broadly neutralizing antibody response comprises a production of neutralizing antibodies that bind to shared epitopes on proteins from the multiple strains of HIV.

3. The method of claim 2, wherein the broadly neutralizing antibody response comprises an $ID_{50}$ titer of greater than 20 or greater than 50.

4. The method of claim 1, wherein (i) the first period of time is 1-30 weeks following administration of the initial dose of the first composition and/or (ii) the second period of time is 8-60 weeks following administration of the initial dose of the first composition.

5. The method of claim 1, wherein the time between any two doses of the first composition of (a) and/or the second composition of (b) is at least 1 week, is at least 4 weeks, or is 4-12 weeks.

6. The method of claim 1, wherein the HIV is HIV type-1 (HIV-1).

7. The method of claim 1, wherein the ratio of the mRNA encoding an HIV Env protein to the mRNA encoding an HIV Gag protein of in the first composition of (a) and/or in the second composition of (b) is 2:1 or 3:2.

8. The method of claim 1, wherein the first composition and/or the second composition further comprises an mRNA encoding an HIV protease.

9. The method of claim 8, wherein the ratio of the mRNA encoding an HIV Gag protein to the mRNA encoding an HIV protease to is at least 1:5, at least 1:10, at least 1:20, at least 1:40, at least 1:60, or at least 1:80.

10. The method of claim 1, wherein the first and/or second composition further comprises an mRNA encoding furin.

11. The method of claim 10, wherein the ratio of the mRNA encoding furin to the mRNA encoding an HIV Env protein is at least 1:5.

12. The method of claim 1, wherein the HIV Env protein of the first composition of (a) is selected from an HIV Env protein of Group M Clade A-K, wherein the HIV Env protein of the second composition of (b) is selected from an HIV Env protein of Group M Clade A-K, and wherein the Clade(s) of the HIV Env protein of the first composition of (a) is different from the Clade(s) of the HIV Env protein of the second composition of (b).

13. The method of claim 1, wherein the HIV Env protein of the first composition of (a) and/or the second composition of (b) comprises HIV Env SOSIP.664 mutations or is a membrane-bound HIV Env protein.

14. The method of claim 1, wherein the cytosolic portion of the HIV Env protein of the first composition of (a) and/or the second composition of (b) is partially truncated.

15. The method of claim 13, wherein the membrane-bound HIV Env protein is gp150 or gp160.

16. The method of claim 1, wherein the HIV Env protein of the first composition of (a) and/or the second composition of (b) comprises a sequence of an Env protein, or a consensus sequence of variants an Env protein, of an HIV strain obtained from an infected subject who has broadly neutralizing antibodies to HIV Env protein, or comprises a sequence of a variant Env protein of an HIV strain that engages one or multiple unmutated common ancestor (UCA) antibodies to HIV Env protein from the lineages of known broadly neutralizing antibodies.

17. The method of claim 1, wherein the HIV Env protein of the first composition of (a) and/or the second composition of (b) comprises:

(i) a mutation selected from 153E, 190G and N276D, relative to the amino acid sequence of HIV Env protein (SEQ ID NO: 2), or other mutations suitable to remove the glycans at positions 188 and 276;

(ii) a mutation selected from N460D and N463D relative to the amino acid sequence of HIV Env protein (SEQ ID NO: 4), or other suitable mutations to remove the glycans at positions 460 and 463;

(iii) a mutation selected from K295N, D386N, and 375Y, relative to the amino acid sequence of HIV Env protein (SEQ ID NO: 3); or (iv) a mutation selected from T322N and S375Y, relative to the amino acid sequence of HIV Env protein (SEQ ID NO: 2).

18. The method of claim 1, wherein the HIV Env protein of the first composition of (a) and/or the second composition of (b) is a tier-2 Env with all the major glycan holes filled in by insertion of the missing glycans.

19. The method of claim 1, wherein the lentivirus is selected from human immunodeficiency virus (HIV), simian immunodeficiency virus (SIV), and murine leukemia virus (muLV).

20. The method of claim 1, wherein the lentivirus-derived Gag is replaced by VSV-AG or VSV core protein.

21. The method of claim 17, wherein:

the HIV Env protein (SEQ ID NO: 2) of the first composition of (a) and/or the second composition of (b) further comprises a disulfide bridge at 113C-432GCG;

the HIV Env protein (SEQ ID NO: 3) of the first composition of (a) and/or the second composition of (b) further comprises a disulfide bridge at 133C-432GCG; or the HIV Env protein (SEQ ID NO: 2) of the first composition of (a) and/or the second composition of (b) further comprises a disulfide bridge at 113C-429GCG.

* * * * *

```
                        SEQUENCE LISTING

<160> NUMBER OF SEQ ID NOS: 13

<210> SEQ ID NO 1
<211> LENGTH: 856
<212> TYPE: PRT
<213> ORGANISM: Artificial Sequence
<220> FEATURE:
<223> OTHER INFORMATION: Synthetic Polypeptide

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
```

-continued

```
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540
```

-continued

Leu Ser Gly Ile Val Gln Gln Gln Asn Asn Leu Leu Arg Ala Ile Glu
545 550 555 560

Ala Gln Gln His Leu Leu Gln Leu Thr Val Trp Gly Ile Lys Gln Leu
565 570 575

Gln Ala Arg Ile Leu Ala Val Glu Arg Tyr Leu Lys Asp Gln Gln Leu
580 585 590

Leu Gly Ile Trp Gly Cys Ser Gly Lys Leu Ile Cys Thr Thr Ala Val
595 600 605

Pro Trp Asn Ala Ser Trp Ser Asn Lys Ser Leu Glu Gln Ile Trp Asn
610 615 620

His Thr Thr Trp Met Glu Trp Asp Arg Glu Ile Asn Asn Tyr Thr Ser
625 630 635 640

Leu Ile His Ser Leu Ile Glu Glu Ser Gln Asn Gln Gln Glu Lys Asn
645 650 655

Glu Gln Glu Leu Leu Glu Leu Asp Lys Trp Ala Ser Leu Trp Asn Trp
660 665 670

Phe Asn Ile Thr Asn Trp Leu Trp Tyr Ile Lys Leu Phe Ile Met Ile
675 680 685

Val Gly Gly Leu Val Gly Leu Arg Ile Val Phe Ala Val Leu Ser Ile
690 695 700

Val Asn Arg Val Arg Gln Gly Tyr Ser Pro Leu Ser Phe Gln Thr His
705 710 715 720

Leu Pro Thr Pro Arg Gly Pro Asp Arg Pro Glu Gly Ile Glu Glu Glu
725 730 735

Gly Gly Glu Arg Asp Arg Asp Arg Ser Ile Arg Leu Val Asn Gly Ser
740 745 750

Leu Ala Leu Ile Trp Asp Asp Leu Arg Ser Leu Cys Leu Phe Ser Tyr
755 760 765

His Arg Leu Arg Asp Leu Leu Leu Ile Val Thr Arg Ile Val Glu Leu
770 775 780

Leu Gly Arg Arg Gly Trp Glu Ala Leu Lys Tyr Trp Trp Asn Leu Leu
785 790 795 800

Gln Tyr Trp Ser Gln Glu Leu Lys Asn Ser Ala Val Ser Leu Leu Asn
805 810 815

Ala Thr Ala Ile Ala Val Ala Glu Gly Thr Asp Arg Val Ile Glu Val
820 825 830

Val Gln Gly Ala Cys Arg Ala Ile Arg His Ile Pro Arg Arg Ile Arg
835 840 845

Gln Gly Leu Glu Arg Ile Leu Leu
850 855

<210> SEQ ID NO 2
<211> LENGTH: 849
<212> TYPE: PRT
<213> ORGANISM: Artificial Sequence
<220> FEATURE:
<223> OTHER INFORMATION: Synthetic Polypeptide

<400> SEQUENCE: 2

Met Lys Val Met Gly Thr Lys Lys Asn Tyr Gln His Leu Trp Arg Trp
1 5 10 15

Gly Ile Met Leu Leu Gly Met Leu Met Met Ser Ser Ala Ala Glu Gln
20 25 30

Leu Trp Val Thr Val Tyr Tyr Gly Val Pro Val Trp Arg Glu Ala Asn
35 40 45

-continued

```
Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Met Gly Asn Val Thr Glu Asp Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

His Cys Thr Asn Val Thr Ile Ser Ser Thr Asn Gly Ser Thr Ala Asn
    130                 135                 140

Val Thr Met Arg Glu Gly Met Lys Asn Cys Ser Phe Asn Thr Thr Thr
145                 150                 155                 160

Val Ile Arg Asp Lys Ile Gln Lys Glu Tyr Ala Leu Phe Tyr Lys Leu
                165                 170                 175

Asp Ile Val Pro Ile Glu Gly Lys Asn Thr Asn Thr Ser Tyr Arg Leu
            180                 185                 190

Ile Asn Cys Asn Thr Ser Val Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Asn Asn Lys Thr Phe Asn Gly Lys Gly Pro Cys Arg Asn
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Asp Ile Ile Ile Arg
            260                 265                 270

Ser Glu Asn Phe Thr Asn Asn Gly Lys Asn Ile Ile Val Gln Leu Lys
        275                 280                 285

Glu Pro Val Lys Ile Asn Cys Thr Arg Pro Gly Asn Asn Thr Arg Arg
    290                 295                 300

Ser Ile Asn Ile Gly Pro Gly Arg Ala Phe Tyr Ala Thr Gly Ala Ile
305                 310                 315                 320

Ile Gly Asp Ile Arg Lys Ala His Cys Asn Ile Ser Thr Glu Gln Trp
                325                 330                 335

Asn Asn Thr Leu Thr Gln Ile Val Asp Lys Leu Arg Glu Gln Phe Gly
            340                 345                 350

Asn Lys Thr Ile Ile Phe Asn Gln Ser Ser Gly Gly Asp Pro Glu Val
        355                 360                 365

Val Met His Thr Phe Asn Cys Gly Gly Glu Phe Phe Tyr Cys Asn Ser
    370                 375                 380

Thr Gln Leu Phe Asn Ser Thr Trp Phe Asn Asn Gly Thr Ser Thr Trp
385                 390                 395                 400

Asn Ser Thr Ala Asp Asn Ile Thr Leu Pro Cys Arg Ile Lys Gln Val
                405                 410                 415

Ile Asn Met Trp Gln Glu Val Gly Lys Ala Met Tyr Ala Pro Pro Ile
            420                 425                 430

Arg Gly Gln Ile Asp Cys Ser Ser Asn Ile Thr Gly Leu Ile Leu Thr
        435                 440                 445

Arg Asp Gly Gly Ser Asn Ser Ser Gln Asn Glu Thr Phe Arg Pro Gly
    450                 455                 460
```

-continued

```
Gly Gly Asn Met Lys Asp Asn Trp Arg Ser Glu Leu Tyr Lys Tyr Lys
465                 470                 475                 480

Val Val Lys Ile Glu Pro Leu Gly Ile Ala Pro Thr Arg Ala Lys Arg
                485                 490                 495

Arg Val Val Gln Arg Glu Lys Arg Ala Val Thr Leu Gly Ala Val Phe
            500                 505                 510

Leu Gly Phe Leu Gly Ala Ala Gly Ser Thr Met Gly Ala Ala Ser Leu
        515                 520                 525

Thr Leu Thr Val Gln Ala Arg Leu Leu Leu Ser Gly Ile Val Gln Gln
    530                 535                 540

Gln Ser Asn Leu Leu Arg Ala Ile Glu Ala Gln Gln His Met Leu Gln
545                 550                 555                 560

Leu Thr Val Trp Gly Ile Lys Gln Leu Gln Ala Arg Val Leu Ala Ile
                565                 570                 575

Glu Arg Tyr Leu Lys Asp Gln Gln Leu Leu Gly Ile Trp Gly Cys Ser
            580                 585                 590

Gly Lys Leu Ile Cys Thr Thr Thr Val Pro Trp Asn Thr Ser Trp Ser
        595                 600                 605

Asn Lys Ser Tyr Asp Tyr Ile Trp Asn Asn Met Thr Trp Met Gln Trp
    610                 615                 620

Glu Arg Glu Ile Asp Asn Tyr Thr Gly Phe Ile Tyr Thr Leu Ile Glu
625                 630                 635                 640

Glu Ser Gln Asn Gln Gln Glu Lys Asn Glu Leu Glu Leu Leu Glu Leu
                645                 650                 655

Asp Lys Trp Ala Ser Leu Trp Asn Trp Phe Asn Ile Thr Asn Trp Leu
            660                 665                 670

Trp Tyr Ile Lys Leu Phe Ile Met Ile Ile Gly Gly Leu Val Gly Leu
        675                 680                 685

Arg Thr Val Cys Ala Val Leu Ser Ile Val Asn Arg Val Arg Gln Gly
    690                 695                 700

Tyr Ser Pro Leu Ser Phe Gln Thr Arg Leu Pro Asn Pro Arg Gly Pro
705                 710                 715                 720

Gly Arg Pro Glu Glu Thr Glu Gly Glu Gly Gly Glu Arg Asp Arg Asp
                725                 730                 735

Arg Ser Ala Arg Leu Val Asn Gly Phe Leu Ala Ile Ile Trp Asp Asp
            740                 745                 750

Leu Arg Ser Leu Cys Leu Phe Ser Tyr His Arg Leu Arg Asp Leu Leu
        755                 760                 765

Leu Ile Val Ala Arg Val Val Glu Ile Leu Gly Arg Arg Gly Trp Glu
    770                 775                 780

Ile Leu Lys Tyr Trp Trp Asn Leu Leu Lys Tyr Trp Ser Gln Glu Leu
785                 790                 795                 800

Lys Asn Ser Ala Val Ser Leu Leu Asn Val Thr Ala Ile Ala Val Ala
                805                 810                 815

Glu Gly Thr Asp Arg Val Ile Glu Ile Val Gln Arg Ala Val Arg Ala
            820                 825                 830

Ile Leu His Ile Pro Thr Arg Ile Arg Gln Gly Phe Glu Arg Ala Leu
        835                 840                 845

Leu

<210> SEQ ID NO 3
<211> LENGTH: 858
<212> TYPE: PRT
<213> ORGANISM: Artificial Sequence
```

-continued

<220> FEATURE:
<223> OTHER INFORMATION: Synthetic Polypeptide

<400> SEQUENCE: 3

```
Met Arg Val Arg Gly Ile Pro Arg Asn Trp Pro Gln Trp Trp Ile Trp
1               5                   10                  15

Gly Ile Leu Gly Phe Trp Met Ile Ile Ile Cys Arg Val Val Gly Asn
            20                  25                  30

Leu Asp Leu Trp Val Thr Val Tyr Tyr Gly Val Pro Val Trp Lys Glu
        35                  40                  45

Ala Lys Thr Thr Leu Phe Cys Ala Ser Asp Ala Lys Ala Tyr Asp Lys
    50                  55                  60

Glu Val His Asn Val Trp Ala Thr His Ala Cys Val Pro Thr Asp Pro
65                  70                  75                  80

Asn Pro Gln Glu Ile Val Leu Glu Asn Val Thr Glu Asn Phe Asn Met
                85                  90                  95

Trp Lys Asn Asp Met Val Asp Gln Met His Glu Asp Ile Ile Ser Leu
            100                 105                 110

Trp Asp Gln Ser Leu Lys Pro Cys Val Lys Leu Thr Pro Leu Cys Val
        115                 120                 125

Thr Leu Asn Cys Lys Asn Val Asn Ile Ser Ala Asn Ala Asn Ala Thr
    130                 135                 140

Ala Thr Leu Asn Ser Ser Met Asn Gly Glu Ile Lys Asn Cys Ser Phe
145                 150                 155                 160

Asn Thr Thr Thr Glu Leu Arg Asp Lys Lys Gln Lys Val Tyr Ala Leu
                165                 170                 175

Phe Tyr Lys Pro Asp Val Val Pro Leu Asn Gly Gly Glu His Asn Glu
            180                 185                 190

Thr Gly Glu Tyr Ile Leu Ile Asn Cys Asn Ser Ser Thr Ile Thr Gln
        195                 200                 205

Ala Cys Pro Lys Val Ser Phe Asp Pro Ile Pro Ile His Tyr Cys Ala
    210                 215                 220

Pro Ala Gly Tyr Ala Ile Leu Lys Cys Asn Asn Lys Thr Phe Asn Gly
225                 230                 235                 240

Thr Gly Pro Cys Asn Asn Val Ser Thr Val Gln Cys Thr His Gly Ile
                245                 250                 255

Lys Pro Val Val Ser Thr Gln Leu Leu Leu Asn Gly Ser Leu Ala Glu
            260                 265                 270

Glu Glu Ile Ile Val Arg Ser Glu Asn Leu Thr Asn Asn Ile Lys Thr
        275                 280                 285

Ile Ile Val His Leu Asn Lys Ser Val Glu Ile Lys Cys Thr Arg Pro
    290                 295                 300

Asn Asn Asn Thr Arg Lys Ser Val Arg Ile Gly Pro Gly Gln Thr Phe
305                 310                 315                 320

Tyr Ala Thr Gly Glu Ile Ile Gly Asp Ile Arg Glu Ala His Cys Asn
                325                 330                 335

Ile Ser Arg Glu Thr Trp Asn Ser Thr Leu Ile Gln Val Lys Glu Lys
            340                 345                 350

Leu Arg Glu His Tyr Asn Lys Thr Ile Lys Phe Glu Pro Ser Ser Gly
        355                 360                 365

Gly Asp Leu Glu Val Thr Thr His Ser Phe Asn Cys Arg Gly Glu Phe
    370                 375                 380

Phe Tyr Cys Asp Thr Thr Lys Leu Phe Asn Glu Thr Lys Leu Phe Asn
385                 390                 395                 400
```

-continued

```
Glu Ser Glu Tyr Val Asp Asn Lys Thr Ile Ile Leu Pro Cys Arg Ile
                405                 410                 415

Lys Gln Ile Ile Asn Met Trp Gln Glu Val Gly Arg Ala Met Tyr Ala
            420                 425                 430

Pro Pro Ile Glu Gly Asn Ile Thr Cys Lys Ser Asn Ile Thr Gly Leu
        435                 440                 445

Leu Leu Thr Trp Asp Gly Gly Glu Asn Ser Thr Glu Gly Val Phe Arg
    450                 455                 460

Pro Gly Gly Gly Asn Met Lys Asp Asn Trp Arg Ser Glu Leu Tyr Lys
465                 470                 475                 480

Tyr Lys Val Val Glu Ile Lys Pro Leu Gly Val Ala Pro Thr Lys Ser
                485                 490                 495

Lys Arg Lys Val Val Gly Arg Glu Lys Arg Ala Val Gly Leu Gly Ala
            500                 505                 510

Val Leu Leu Gly Phe Leu Gly Ala Ala Gly Ser Thr Met Gly Ala Ala
        515                 520                 525

Ser Ile Thr Leu Thr Val Gln Ala Arg Gln Leu Leu Ser Gly Ile Val
    530                 535                 540

Gln Gln Gln Ser Asn Leu Leu Arg Ala Ile Glu Ala Gln Gln His Leu
545                 550                 555                 560

Leu Gln Leu Thr Val Trp Gly Ile Lys Gln Leu Gln Thr Arg Val Leu
                565                 570                 575

Ala Ile Glu Arg Tyr Leu Lys Asp Gln Gln Leu Leu Gly Leu Trp Gly
            580                 585                 590

Cys Ser Gly Lys Leu Ile Cys Ala Thr Ala Val Pro Trp Asn Ser Ser
        595                 600                 605

Trp Ser Asn Lys Ser Leu Gly Asp Ile Trp Asp Asn Met Thr Trp Met
    610                 615                 620

Gln Trp Asp Arg Glu Ile Ser Asn Tyr Thr Asn Thr Ile Phe Arg Leu
625                 630                 635                 640

Leu Glu Asp Ser Gln Asn Gln Gln Glu Lys Asn Glu Lys Asp Leu Leu
                645                 650                 655

Ala Leu Asp Ser Trp Lys Asn Leu Trp Asn Trp Phe Asp Ile Thr Asn
            660                 665                 670

Trp Leu Trp Tyr Ile Lys Ile Phe Ile Met Ile Val Gly Gly Leu Ile
        675                 680                 685

Gly Leu Arg Ile Ile Phe Gly Val Leu Ala Ile Val Lys Arg Val Arg
    690                 695                 700

Gln Gly Tyr Ser Pro Leu Ser Phe Gln Thr Leu Ile Pro Asn Pro Arg
705                 710                 715                 720

Gly Pro Asp Arg Leu Gly Arg Ile Glu Glu Glu Gly Gly Glu Gln Asp
                725                 730                 735

Lys Asp Arg Ser Ile Arg Leu Val Ser Gly Phe Leu Ala Leu Ala Trp
            740                 745                 750

Asp Asp Leu Arg Ser Leu Cys Leu Phe Ser Tyr His Gln Leu Arg Asp
        755                 760                 765

Phe Ile Leu Thr Ala Ala Arg Ala Ala Glu Leu Leu Gly Arg Ser Ser
    770                 775                 780

Leu Arg Gly Leu Gln Arg Gly Trp Glu Val Leu Lys Tyr Leu Gly Asn
785                 790                 795                 800

Leu Val Gln Tyr Trp Gly Leu Glu Leu Lys Arg Ser Ala Ile Asn Leu
                805                 810                 815
```

```
Phe Asp Thr Ile Ala Ile Ala Val Ala Glu Gly Thr Asp Arg Ile Ile
            820                 825                 830

Glu Val Ile Gln Arg Ile Cys Arg Ala Ile Arg Tyr Ile Pro Thr Arg
        835                 840                 845

Ile Arg Gln Gly Phe Glu Ala Ala Leu Leu
    850                 855


<210> SEQ ID NO 4
<211> LENGTH: 860
<212> TYPE: PRT
<213> ORGANISM: Artificial Sequence
<220> FEATURE:
<223> OTHER INFORMATION: Synthetic Polypeptide

<400> SEQUENCE: 4

Met Arg Val Met Gly Ile Gln Arg Asn Cys Gln His Leu Phe Arg Trp
1               5                   10                  15

Gly Thr Met Ile Leu Gly Met Ile Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Lys
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Gln Cys Thr Asn Val Thr Asn Asn Ile Thr Asp Asp Met Arg Gly Glu
    130                 135                 140

Leu Lys Asn Cys Ser Phe Asn Met Thr Thr Glu Leu Arg Asp Lys Lys
145                 150                 155                 160

Gln Lys Val Tyr Ser Leu Phe Tyr Arg Leu Asp Val Val Gln Ile Asn
                165                 170                 175

Glu Asn Gln Gly Asn Arg Ser Asn Asn Ser Asn Lys Glu Tyr Arg Leu
            180                 185                 190

Ile Asn Cys Asn Thr Ser Ala Ile Thr Gln Ala Cys Pro Lys Val Ser
        195                 200                 205

Phe Glu Pro Ile Pro Ile His Tyr Cys Ala Pro Ala Gly Phe Ala Ile
    210                 215                 220

Leu Lys Cys Lys Asp Lys Lys Phe Asn Gly Thr Gly Pro Cys Pro Ser
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Glu Val Met Ile Arg
            260                 265                 270

Ser Glu Asn Ile Thr Asn Asn Ala Lys Asn Ile Leu Val Gln Phe Asn
        275                 280                 285

Thr Pro Val Gln Ile Asn Cys Thr Arg Pro Asn Asn Asn Thr Arg Lys
    290                 295                 300

Ser Ile Arg Ile Gly Pro Gly Gln Ala Phe Tyr Ala Thr Gly Asp Ile
305                 310                 315                 320
```

```
Ile Gly Asp Ile Arg Gln Ala His Cys Thr Val Ser Lys Ala Thr Trp
                325                 330                 335

Asn Glu Thr Leu Gly Lys Val Val Lys Gln Leu Arg Lys His Phe Gly
            340                 345                 350

Asn Asn Thr Ile Ile Arg Phe Ala Asn Ser Ser Gly Gly Asp Leu Glu
        355                 360                 365

Val Thr Thr His Ser Phe Asn Cys Gly Gly Glu Phe Phe Tyr Cys Asn
    370                 375                 380

Thr Ser Gly Leu Phe Asn Ser Thr Trp Ile Ser Asn Thr Ser Val Gln
385                 390                 395                 400

Gly Ser Asn Ser Thr Gly Ser Asn Asp Ser Ile Thr Leu Pro Cys Arg
                405                 410                 415

Ile Lys Gln Ile Ile Asn Met Trp Gln Arg Ile Gly Gln Ala Met Tyr
            420                 425                 430

Ala Pro Pro Ile Gln Gly Val Ile Arg Cys Val Ser Asn Ile Thr Gly
        435                 440                 445

Leu Ile Leu Thr Arg Asp Gly Gly Ser Thr Asn Ser Thr Thr Glu Thr
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Arg Ala Lys Arg Arg Val Val Gly Arg Glu Lys Arg Ala Val Gly Ile
            500                 505                 510

Gly Ala Val Phe Leu Gly Phe Leu Gly Ala Ala Gly Ser Thr Met Gly
        515                 520                 525

Ala Ala Ser Met Thr Leu Thr Val Gln Ala Arg Asn Leu Leu Ser Gly
    530                 535                 540

Ile Val Gln Gln Gln Ser Asn Leu Leu Arg Ala Ile Glu Ala Gln Gln
545                 550                 555                 560

His Leu Leu Lys Leu Thr Val Trp Gly Ile Lys Gln Leu Gln Ala Arg
                565                 570                 575

Val Leu Ala Val Glu Arg Tyr Leu Arg Asp Gln Gln Leu Leu Gly Ile
            580                 585                 590

Trp Gly Cys Ser Gly Lys Leu Ile Cys Thr Thr Asn Val Pro Trp Asn
        595                 600                 605

Ser Ser Trp Ser Asn Arg Asn Leu Ser Glu Ile Trp Asp Asn Met Thr
    610                 615                 620

Trp Leu Gln Trp Asp Lys Glu Ile Ser Asn Tyr Thr Gln Ile Ile Tyr
625                 630                 635                 640

Gly Leu Leu Glu Glu Ser Gln Asn Gln Gln Glu Lys Asn Glu Gln Asp
                645                 650                 655

Leu Leu Ala Leu Asp Lys Trp Ala Ser Leu Trp Asn Trp Phe Asp Ile
            660                 665                 670

Ser Asn Trp Leu Trp Tyr Ile Lys Ile Phe Ile Met Ile Val Gly Gly
        675                 680                 685

Leu Ile Gly Leu Arg Ile Val Phe Ala Val Leu Ser Val Ile His Arg
    690                 695                 700

Val Arg Gln Gly Tyr Ser Pro Leu Ser Phe Gln Thr His Thr Pro Asn
705                 710                 715                 720

Pro Arg Gly Leu Asp Arg Pro Glu Arg Ile Glu Glu Glu Asp Gly Glu
                725                 730                 735

Gln Asp Arg Gly Arg Ser Thr Arg Leu Val Ser Gly Phe Leu Ala Leu
```

```
            740                 745                 750

Ala Trp Asp Asp Leu Arg Ser Leu Cys Leu Phe Cys Tyr His Arg Leu
        755                 760                 765

Arg Asp Phe Ile Leu Ile Ala Ala Arg Ile Val Glu Leu Leu Gly His
    770                 775                 780

Ser Ser Leu Lys Gly Leu Arg Leu Gly Trp Glu Gly Leu Lys Tyr Leu
785                 790                 795                 800

Trp Asn Leu Leu Ala Tyr Trp Gly Arg Glu Leu Lys Ile Ser Ala Ile
                805                 810                 815

Asn Leu Phe Asp Thr Ile Ala Ile Ala Val Ala Glu Trp Thr Asp Arg
            820                 825                 830

Val Ile Glu Ile Gly Gln Arg Leu Cys Arg Ala Phe Leu His Ile Pro
        835                 840                 845

Arg Arg Ile Arg Gln Gly Leu Glu Arg Ala Leu Leu
    850                 855                 860


<210> SEQ ID NO 5
<211> LENGTH: 500
<212> TYPE: PRT
<213> ORGANISM: Artificial Sequence
<220> FEATURE:
<223> OTHER INFORMATION: Synthetic Polypeptide

<400> SEQUENCE: 5

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
```

-continued

```
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Ile Val Lys Cys Phe Asn Cys Gly Lys Glu Gly His
385                 390                 395                 400

Thr Ala Arg Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Tyr Lys Gly Arg Pro Gly Asn Phe
        435                 440                 445

Leu Gln Ser Arg Pro Glu Pro Thr Ala Pro Pro Glu Glu Ser Phe Arg
    450                 455                 460

Ser Gly Val Glu Thr Thr Thr Pro Pro Gln Lys Gln Glu Pro Ile Asp
465                 470                 475                 480

Lys Glu Leu Tyr Pro Leu Thr Ser Leu Arg Ser Leu Phe Gly Asn Asp
                485                 490                 495

Pro Ser Ser Gln
            500
```

<210> SEQ ID NO 6
<211> LENGTH: 4307
<212> TYPE: DNA
<213> ORGANISM: Artificial Sequence
<220> FEATURE:
<223> OTHER INFORMATION: Synthetic Polynucleotide

<400> SEQUENCE: 6

```
atgggtgcga gagcgtcagt attaagcggg ggagaattag atcgatggga aaaaattcgg     60

ttaaggccag ggggaaagaa aaaatataaa ttaaaacata tagtatgggc aagcagggag    120

ctagaacgat tcgcagttaa tcctggcctg ttagaaacat cagaaggctg tagacaaata    180

ctgggacagc tacaaccatc ccttcagaca ggatcagaag aacttagatc attatataat    240

acagtagcaa ccctctattg tgtgcatcaa aggatagaga taaaagacac caaggaagct    300

ttagacaaga tagaggaaga gcaaaacaaa agtaagaaaa aagcacagca agcagcagct    360

gacacaggac acagcaatca ggtcagccaa aattacccta tagtgcagaa catccagggg    420

caaatggtac atcaggccat atcacctaga actttaaatg catgggtaaa agtagtagaa    480

gagaaggctt tcagcccaga agtgataccc atgttttcag cattatcaga aggagccacc    540

ccacaagatt taaacaccat gctaaacaca gtgggggga atcaagcagc catgcaaatg    600
```

-continued

```
ttaaaagaga ccatcaatga ggaagctgca gaatgggata gagtgcatcc agtgcatgca    660
gggcctattg caccaggcca gatgagagaa ccaaggggaa gtgacatagc aggaactact    720
agtacccttc aggaacaaat aggatggatg acacataatc cacctatccc agtaggagaa    780
atctataaaa gatggataat cctgggatta aataaaatag taagaatgta tagccctacc    840
agcattctgg acataagaca aggaccaaag gaacccttta gagactatgt agaccgattc    900
tataaaactc taagagccga gcaagcttca caagaggtaa aaaattggat gacagaaacc    960
ttgttggtcc aaaatgcgaa cccagattgt aagactattt taaaagcatt gggaccagga   1020
gcgacactag aagaaatgat gacagcatgt cagggagtgg ggggacccgg ccataaagca   1080
agagttttgg ctgaagcaat gagccaagta acaaatccag ctaccataat gatacagaaa   1140
ggcaatttta ggaaccaaag aaagactgtt aagtgtttca attgtggcaa agaagggcac   1200
atagccaaaa attgcagggc ccctaggaaa aagggctgtt ggaaatgtgg aaaggaagga   1260
caccaaatga aagattgtac tgagagacag gctaattttt tagggaagat ctggccttcc   1320
cacaagggaa ggccagggaa ttttcttcag agcagaccag agccaacagc cccaccagaa   1380
gagagcttca ggtttgggga agagacaaca actccctctc agaagcagga gccgatagac   1440
aaggaactgt atcctttagc ttccctcaga tcactctttg gcagcgaccc ctcgtcacaa   1500
taaagatagg ggggcaatta aaggaagctc tattagatac aggagcagat gatacagtat   1560
tagaagaaat gaatttgcca ggaagatgga aaccaaaaat gataggggga attggaggtt   1620
ttatcaaagt aagacagtat gatcagatac tcatagaaat ctgcggacat aaagctatag   1680
gtacagtatt agtaggacct acacctgtca acataattgg aagaaatctg ttgactcaga   1740
ttggctgcac tttaaatttt cccattagtc ctattgagac tgtaccagta aaattaaagc   1800
caggaatgga tggcccaaaa gttaaacaat ggccattgac agaagaaaaa ataaaagcat   1860
tagtagaaat ttgtacagaa atggaaaagg aaggaaaaat ttcaaaaatt gggcctgaaa   1920
atccatacaa tactccagta tttgccataa agaaaaaaga cagtactaaa tggagaaaat   1980
tagtagattt cagagaactt aataagagaa ctcaagattt ctgggaagtt caattaggaa   2040
taccacatcc tgcagggtta aaacagaaaa aatcagtaac agtactggat gtgggcgatg   2100
catatttttc agttccctta gataaagact tcaggaagta tactgcattt accataccta   2160
gtataaacaa tgagacacca gggattagat atcagtacaa tgtgcttcca cagggatgga   2220
aaggatcacc agcaatattc cagtgtagca tgacaaaaat cttagagcct tttagaaaac   2280
aaaatccaga catagtcatc tatcaataca tggatgattt gtatgtagga tctgacttag   2340
aaatagggca gcatagaaca aaaatagagg aactgagaca acatctgttg aggtggggat   2400
ttaccacacc agacaaaaaa catcagaaag aacctccatt cctttggatg ggttatgaac   2460
tccatcctga taaatggaca gtacagccta tagtgctgcc agaaaaggac agctggactg   2520
tcaatgacat acagaaatta gtgggaaaat tgaattgggc aagtcagatt tatgcaggga   2580
ttaaagtaag gcaattatgt aaacttctta ggggaaccaa agcactaaca gaagtagtac   2640
cactaacaga agaagcagag ctagaactgg cagaaaacag ggagattcta aaagaaccgg   2700
tacatggagt gtattatgac ccatcaaaag acttaatagc agaaatacag aagcaggggc   2760
aaggccaatg gacatatcaa atttatcaag agccatttaa aaatctgaaa acaggaaagt   2820
atgcaagaat gaagggtgcc cacactaatg atgtgaaaca attaacagag gcagtacaaa   2880
aaatagccac agaaagcata gtaatatggg gaaagactcc taaatttaaa ttacccatac   2940
```

-continued

```
aaaaggaaac atgggaagca tggtggacag agtattggca agccacctgg attcctgagt   3000
gggagtttgt caatacccct cccttagtga agttatggta ccagttagag aaagaaccca   3060
taataggagc agaaactttc tatgtagatg ggcagccaa tagggaaact aaattaggaa    3120
aagcaggata tgtaactgac agaggaagac aaaaagttgt cccccctaacg gacacaacaa   3180 atcagaagac tgagttacaa gcaattcatc tagctttgca ggattcggga ttagaagtaa   3240
acatagtgac agactcacaa tatgcattgg gaatcattca agcacaacca gataagagtg   3300
aatcagagtt agtcagtcaa ataatagagc agttaataaa aaaggaaaaa gtctacctgg   3360
catgggtacc agcacacaaa ggaattggag gaaatgaaca agtagataaa ttggtcagtg   3420
ctggaatcag gaaagtacta tttttagatg gaatagataa ggcccaagaa gaacatgaga   3480
aatatcacag taattggaga gcaatggcta gtgattttaa cctaccacct gtagtagcaa   3540
aagaaatagt agccagctgt gataaatgtc agctaaaagg ggaagccatg catggacaag   3600
tagactgtag cccaggaata tggcagctag attgtacaca tttagaagga aaagttatct   3660
tggtagcagt tcatgtagcc agtggatata tagaagcaga agtaattcca gcagagacag   3720
ggcaagaaac agcatacttc ctcttaaaat tagcaggaag atggccagta aaaacagtac   3780
atacagacaa tggcagcaat ttcaccagta ctacagttaa ggccgcctgt tggtgggcgg   3840
ggatcaagca ggaatttggc attccctaca atccccaaag tcaaggagta atagaatcta   3900
tgaataaaga attaaagaaa attataggac aggtaagaga tcaggctgaa catcttaaga   3960
cagcagtaca aatggcagta ttcatccaca attttaaaag aaaagggggg attgggggt   4020 acagtgcagg ggaaagaata gtagacataa tagcaacaga catacaaact aaagaattac   4080
aaaaacaaat tacaaaaatt caaaattttc gggtttatta cagggacagc agagatccag   4140
tttggaaagg accagcaaag ctcctctgga aaggtgaagg ggcagtagta atacaagata   4200
atagtgacat aaaagtagtg ccaagaagaa aagcaaagat catcagggat tatggaaaac   4260
agatggcagg tgatgattgt gtggcaagta gacaggatga ggattaa                 4307
```

```
<210> SEQ ID NO 7
<211> LENGTH: 99
<212> TYPE: PRT
<213> ORGANISM: Artificial Sequence
<220> FEATURE:
<223> OTHER INFORMATION: Synthetic Polypeptide

<400> SEQUENCE: 7

Pro Gln Ile Thr Leu Trp Lys Arg Pro Leu Val Thr Ile Lys Ile Gly
1               5                   10                  15

Gly Gln Leu Lys Glu Ala Leu Leu Asp Thr Gly Ala Asp Asp Thr Val
            20                  25                  30

Leu Glu Glu Met Asn Leu Pro Gly Arg Trp Lys Pro Lys Met Ile Gly
        35                  40                  45

Gly Ile Gly Gly Phe Ile Lys Val Arg Gln Tyr Asp Gln Ile Leu Ile
    50                  55                  60

Glu Ile Cys Gly His Lys Ala Ile Gly Thr Val Leu Val Gly Pro Thr
65                  70                  75                  80

Pro Val Asn Ile Ile Gly Arg Asn Leu Leu Thr Gln Ile Gly Cys Thr
                85                  90                  95

Leu Asn Phe

<210> SEQ ID NO 8
<211> LENGTH: 794
```

<212> TYPE: PRT
<213> ORGANISM: Artificial Sequence
<220> FEATURE:
<223> OTHER INFORMATION: Synthetic Polypeptide

<400> SEQUENCE: 8

```
Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
    370                 375                 380
```

-continued

```
Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
            420                 425                 430

Ala Met Val Ala Leu Ala Gln Asn Trp Thr Thr Val Ala Pro Gln Arg
        435                 440                 445

Lys Cys Ile Ile Asp Ile Leu Thr Glu Pro Lys Asp Ile Gly Lys Arg
    450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Met Thr Thr His Ser Trp Asp Glu Asp Pro Ser
    530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
    610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

Arg Ala Gly Leu Leu Pro Ser His Leu Pro Glu Val Val Ala Gly Leu
705                 710                 715                 720

Ser Cys Ala Phe Ile Val Leu Val Phe Val Thr Val Phe Leu Val Leu
                725                 730                 735

Gln Leu Arg Ser Gly Phe Ser Phe Arg Gly Val Lys Val Tyr Thr Met
            740                 745                 750

Asp Arg Gly Leu Ile Ser Tyr Lys Gly Leu Pro Pro Glu Ala Trp Gln
        755                 760                 765

Glu Glu Cys Pro Ser Asp Ser Glu Glu Asp Glu Gly Arg Gly Glu Arg
    770                 775                 780

Thr Ala Phe Ile Lys Asp Gln Ser Ala Leu
785                 790
```

<210> SEQ ID NO 9
<211> LENGTH: 668
<212> TYPE: PRT
<213> ORGANISM: Artificial Sequence
<220> FEATURE:
<223> OTHER INFORMATION: Synthetic Polypeptide

<400> SEQUENCE: 9

```
Met Asp Ala Met Lys Arg Gly Leu Cys Cys Val Leu Leu Leu Cys Gly
1               5                   10                  15

Ala Val Phe Val Ser Pro Ser Gln Glu Ile His Ala Arg Phe Arg Arg
            20                  25                  30

Gly Ala Arg Ala Glu Asn Leu Trp Val Thr Val Tyr Tyr Gly Val Pro
        35                  40                  45

Val Trp Lys Asp Ala Glu Thr Thr Leu Phe Cys Ala Ser Asp Ala Lys
    50                  55                  60

Ala Tyr Glu Thr Glu Lys His Asn Val Trp Ala Thr His Ala Cys Val
65                  70                  75                  80

Pro Thr Asp Pro Asn Pro Gln Glu Ile His Leu Glu Asn Val Thr Glu
                85                  90                  95

Glu Phe Asn Met Trp Lys Asn Asn Met Val Glu Gln Met His Thr Asp
            100                 105                 110

Ile Ile Ser Leu Trp Asp Gln Ser Leu Lys Pro Cys Val Lys Leu Thr
        115                 120                 125

Pro Leu Cys Val Thr Leu Gln Cys Thr Asn Val Thr Asn Asn Ile Thr
    130                 135                 140

Asp Asp Met Arg Gly Glu Leu Lys Asn Cys Ser Phe Asn Met Thr Thr
145                 150                 155                 160

Glu Leu Arg Asp Lys Lys Gln Lys Val Tyr Ser Leu Phe Tyr Arg Leu
                165                 170                 175

Asp Val Val Gln Ile Asn Glu Asn Gln Gly Asn Arg Ser Asn Asn Ser
            180                 185                 190

Asn Lys Glu Tyr Arg Leu Ile Cys Asn Thr Ser Ala Ile Thr Gln Ala
        195                 200                 205

Cys Pro Lys Val Ser Phe Glu Pro Ile Pro Ile His Tyr Cys Ala Pro
    210                 215                 220

Ala Gly Phe Ala Ile Leu Lys Cys Lys Asp Lys Lys Phe Asn Gly Thr
225                 230                 235                 240

Gly Pro Cys Pro Ser Val Ser Thr Val Gln Cys Thr His Gly Ile Lys
                245                 250                 255

Pro Val Val Ser Thr Gln Leu Leu Leu Asn Gly Ser Leu Ala Glu Glu
            260                 265                 270

Glu Val Met Ile Arg Ser Glu Asn Ile Thr Asn Asn Ala Lys Asn Ile
        275                 280                 285

Leu Val Gln Phe Asn Thr Pro Val Gln Ile Asn Cys Thr Arg Pro Asn
    290                 295                 300

Asn Asn Thr Arg Lys Ser Ile Arg Ile Gly Pro Gly Gln Ala Phe Tyr
305                 310                 315                 320

Ala Thr Gly Asp Ile Ile Gly Asp Ile Arg Gln Ala His Cys Asn Val
                325                 330                 335

Ser Lys Ala Thr Trp Asn Glu Thr Leu Gly Lys Val Val Lys Gln Leu
            340                 345                 350

Arg Lys His Phe Gly Asn Asn Thr Ile Ile Arg Phe Ala Asn Ser Ser
        355                 360                 365

Gly Gly Asp Leu Glu Val Thr Thr His Ser Phe Asn Cys Gly Gly Glu
```

-continued

```
    370                 375                 380

Phe Phe Tyr Cys Asn Thr Ser Gly Leu Phe Asn Ser Thr Trp Ile Ser
385                 390                 395                 400

Asn Thr Ser Val Gln Gly Ser Asn Ser Thr Gly Ser Asn Asp Ser Ile
                405                 410                 415

Thr Leu Pro Cys Arg Ile Lys Gln Ile Ile Asn Met Trp Gln Arg Ile
            420                 425                 430

Gly Gln Ala Met Tyr Ala Pro Pro Ile Gln Gly Val Ile Arg Cys Val
        435                 440                 445

Ser Asn Ile Thr Gly Leu Ile Leu Thr Arg Asp Gly Gly Ser Thr Asn
    450                 455                 460

Ser Thr Thr Glu Thr Phe Arg Pro Gly Gly Gly Asp Met Arg Asp Asn
465                 470                 475                 480

Trp Arg Ser Glu Leu Tyr Lys Tyr Lys Val Val Lys Ile Glu Pro Leu
                485                 490                 495

Gly Val Ala Pro Thr Arg Cys Lys Arg Arg Val Val Gly Arg Arg Arg
            500                 505                 510

Arg Arg Arg Ala Val Gly Ile Gly Ala Val Phe Leu Gly Phe Leu Gly
        515                 520                 525

Ala Ala Gly Ser Thr Met Gly Ala Ala Ser Met Thr Leu Thr Val Gln
    530                 535                 540

Ala Arg Asn Leu Leu Ser Gly Ile Val Gln Gln Gln Ser Asn Leu Leu
545                 550                 555                 560

Arg Ala Pro Glu Ala Gln Gln His Leu Leu Lys Leu Thr Val Trp Gly
                565                 570                 575

Ile Lys Gln Leu Gln Ala Arg Val Leu Ala Val Glu Arg Tyr Leu Arg
            580                 585                 590

Asp Gln Gln Leu Leu Gly Ile Trp Gly Cys Ser Gly Lys Leu Ile Cys
        595                 600                 605

Cys Thr Asn Val Pro Trp Asn Ser Ser Trp Ser Asn Arg Asn Leu Ser
    610                 615                 620

Glu Ile Trp Asp Asn Met Thr Trp Leu Gln Trp Asp Lys Glu Ile Ser
625                 630                 635                 640

Asn Tyr Thr Gln Ile Ile Tyr Gly Leu Leu Glu Glu Ser Gln Asn Gln
                645                 650                 655

Gln Glu Lys Asn Glu Gln Asp Leu Leu Ala Leu Asp
            660                 665


<210> SEQ ID NO 10
<211> LENGTH: 47
<212> TYPE: RNA
<213> ORGANISM: Artificial Sequence
<220> FEATURE:
<223> OTHER INFORMATION: Synthetic Polynucleotide

<400> SEQUENCE: 10

gggaaauaag agagaaaaga agaguaagaa gaaauauaag agccacc                   47


<210> SEQ ID NO 11
<211> LENGTH: 57
<212> TYPE: RNA
<213> ORGANISM: Artificial Sequence
<220> FEATURE:
<223> OTHER INFORMATION: Synthetic Polynucleotide

<400> SEQUENCE: 11

gggaaauaag agagaaaaga agaguaagaa gaaauauaag accccggcgc cgccacc        57
```

-continued

```
<210> SEQ ID NO 12
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 12

ugauaauagg cuggagccuc gguggccaug cuucuugccc cuugggccuc cccccagccc      60

cuccuccccu uccugcaccc guacccccgu ggucuuugaa uaaagucuga gugggcggc      119


<210> SEQ ID NO 13
<211> LENGTH: 119
<212> TYPE: RNA
<213> ORGANISM: Artificial Sequence
<220> FEATURE:
<223> OTHER INFORMATION: Synthetic Polynucleotide

<400> SEQUENCE: 13

ugauaauagg cuggagccuc gguggccuag cuucuugccc cuugggccuc cccccagccc      60

cuccuccccu uccugcaccc guacccccgu ggucuuugaa uaaagucuga gugggcggc      119
```

UNITED STATES PATENT AND TRADEMARK OFFICE
CERTIFICATE OF CORRECTION

| | | |
|---|---|---|
| PATENT NO. | : 12,070,495 B2 | Page 1 of 1 |
| APPLICATION NO. | : 17/439198 | |
| DATED | : August 27, 2024 | |
| INVENTOR(S) | : Paolo Lusso et al. | |

It is certified that error appears in the above-identified patent and that said Letters Patent is hereby corrected as shown below:

In the Specification

At item (57), in the Abstract, Line 2 "in a subject abroad neutralizing antibody response to human" should read --in a subject a broad neutralizing antibody response to human--.

In the Claims

At Column 96, Line 8, "VSV-AG" should read --VSV-ΔG--.

Signed and Sealed this
Twelfth Day of November, 2024

Katherine Kelly Vidal
*Director of the United States Patent and Trademark Office*